United States Patent
Beaumont et al.

(10) Patent No.: US 10,705,082 B2
(45) Date of Patent: Jul. 7, 2020

(54) IN SITU-GENERATED MICROFLUIDIC ASSAY STRUCTURES, RELATED KITS, AND METHODS OF USE THEREOF

(71) Applicant: Berkeley Lights, Inc., Emeryville, CA (US)

(72) Inventors: Kristin G. Beaumont, New York City, NY (US); Peter J. Beemiller, Emeryville, CA (US); Volker L. S. Kurz, Oakland, CA (US); Gregory G. Lavieu, Emeryville, CA (US); Xiaohua Wang, Albany, CA (US); Aathavan Karunakaran, Berkeley, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 182 days.

(21) Appl. No.: 15/372,094

(22) Filed: Dec. 7, 2016

(65) Prior Publication Data
US 2017/0184583 A1    Jun. 29, 2017

Related U.S. Application Data

(60) Provisional application No. 62/264,665, filed on Dec. 8, 2015, provisional application No. 62/333,821, filed
(Continued)

(51) Int. Cl.
*B01L 3/00* (2006.01)
*G01N 33/543* (2006.01)
(Continued)

(52) U.S. Cl.
CPC .. *G01N 33/54386* (2013.01); *B01L 3/502707* (2013.01); *B01L 3/502792* (2013.01);
(Continued)

(58) Field of Classification Search
CPC ........... B01L 3/5027; B01L 3/502; B01L 3/50
(Continued)

(56) References Cited

U.S. PATENT DOCUMENTS

| 6,294,063 B1 | 9/2001 | Becker |
| 6,387,707 B1 | 5/2002 | Seul et al. |

(Continued)

FOREIGN PATENT DOCUMENTS

| EP | 1065378 A2 | 1/2001 |
| WO | 00/46595 A1 | 8/2000 |

(Continued)

OTHER PUBLICATIONS

Peter R. C. Gascoyne et al., "Dielectrophoretic Separation of Cancer Cells from Blood", IEEE Trans Ind Appl. 1997, vol. 33(3), pp. 67-678, Dec. 2009.

(Continued)

*Primary Examiner* — Christine T Mui
(74) *Attorney, Agent, or Firm* — McDermott Will & Emery LLP

(57) ABSTRACT

In situ-generated microfluidic capture structures incorporating a solidified polymer network, methods of preparation and use, compositions and kits therefor are described. Microfluidic capture structures may be advantageously used for assays performed within the microfluidic environment, providing flexibility in assaying micro-objects such as biological cells. Assay reagents and analytes may be incorporated within the microfluidic capture structures.

29 Claims, 17 Drawing Sheets

Related U.S. Application Data on May 9, 2016, provisional application No. 62/418,625, filed on Nov. 7, 2016.

(51) Int. Cl.
  *G01N 33/545* (2006.01)
  *G01N 33/58* (2006.01)

(52) U.S. Cl.
  CPC ..... *G01N 33/545* (2013.01); *G01N 33/54366* (2013.01); *G01N 33/582* (2013.01); *B01L 3/502761* (2013.01); *B01L 2200/0668* (2013.01); *B01L 2300/0681* (2013.01); *B01L 2300/0816* (2013.01); *B01L 2300/0864* (2013.01); *B01L 2400/0424* (2013.01); *B01L 2400/0427* (2013.01)

(58) Field of Classification Search
  USPC ........................................ 422/502, 500, 50
  See application file for complete search history.

(56) References Cited

U.S. PATENT DOCUMENTS

| | | |
|---|---|---|
| 6,408,878 B2 | 6/2002 | Unger et al. |
| 6,488,872 B1 | 12/2002 | Beebe et al. |
| 6,942,776 B2 | 9/2005 | Medoro |
| 7,090,759 B1 | 8/2006 | Seul |
| 7,790,631 B2 | 9/2010 | Sharma |
| 8,685,344 B2 | 4/2014 | Sudarsan et al. |
| 2003/0008364 A1 | 1/2003 | Wang |
| 2003/0224528 A1 | 12/2003 | Chiou |
| 2004/0072278 A1 | 4/2004 | Chou |
| 2004/0115838 A1* | 6/2004 | Quake .................. B01D 57/02 436/538 |
| 2004/0191789 A1 | 9/2004 | Manaresi et al. |
| 2005/0112548 A1 | 5/2005 | Segawa |
| 2005/0129581 A1 | 6/2005 | McBride et al. |
| 2005/0175702 A1 | 8/2005 | Muller-Schulte |
| 2005/0175981 A1 | 8/2005 | Voldman |
| 2005/0208465 A1* | 9/2005 | Arai .................. B01L 3/502753 435/4 |
| 2006/0091015 A1 | 5/2006 | Lau |
| 2006/0154361 A1 | 7/2006 | Wikswo et al. |
| 2006/0240548 A1 | 10/2006 | Deutsch et al. |
| 2007/0095669 A1 | 5/2007 | Lau |
| 2007/0183934 A1 | 8/2007 | Diercks et al. |
| 2007/0242105 A1 | 10/2007 | Srinivasan et al. |
| 2008/0014575 A1 | 1/2008 | Nelson |
| 2008/0153134 A1 | 6/2008 | Wiyatno |
| 2008/0302732 A1 | 12/2008 | Soh |
| 2009/0023608 A1 | 1/2009 | Hung et al. |
| 2009/0170186 A1 | 7/2009 | Wu |
| 2010/0003666 A1 | 1/2010 | Lee |
| 2010/0101960 A1 | 4/2010 | Ohta |
| 2010/0263599 A1 | 10/2010 | Yanik |
| 2010/0273681 A1 | 10/2010 | Cerrina et al. |
| 2010/0285490 A1 | 11/2010 | Dees et al. |
| 2011/0117634 A1 | 5/2011 | Halamish |
| 2011/0143964 A1 | 6/2011 | Zhou |
| 2011/0186165 A1 | 8/2011 | Borenstein et al. |
| 2011/0195527 A1 | 8/2011 | O'Neill et al. |
| 2011/0262906 A1 | 10/2011 | Dimov et al. |
| 2012/0009671 A1 | 1/2012 | Hansen et al. |
| 2012/0015347 A1 | 1/2012 | Singhal et al. |
| 2012/0024708 A1 | 2/2012 | Chiou et al. |
| 2012/0118740 A1 | 5/2012 | Garcia |
| 2012/0156675 A1 | 6/2012 | Lueerssen et al. |
| 2012/0208266 A1 | 8/2012 | Bookbinder et al. |
| 2012/0325665 A1 | 12/2012 | Chiou et al. |
| 2013/0118905 A1 | 5/2013 | Morimoto |
| 2013/0171628 A1 | 7/2013 | DiCarlo |
| 2013/0190212 A1 | 7/2013 | Handique |
| 2013/0204076 A1 | 8/2013 | Han |
| 2013/0261021 A1 | 10/2013 | Bocchi et al. |
| 2013/0277218 A1 | 10/2013 | Mudrick |
| 2014/0057311 A1 | 2/2014 | Kamm et al. |
| 2014/0116881 A1 | 5/2014 | Chapman |
| 2014/0124370 A1 | 5/2014 | Short |
| 2015/0018226 A1 | 1/2015 | Hansen et al. |
| 2015/0151298 A1 | 4/2015 | Hobbs |
| 2015/0151307 A1 | 4/2015 | Breinlinger |
| 2015/0165436 A1 | 4/2015 | Chapman |
| 2015/0148264 A1 | 5/2015 | Esfandyarpour et al. |
| 2015/0167043 A1 | 6/2015 | Goluch et al. |
| 2015/0306598 A1 | 10/2015 | Khandros et al. |
| 2015/0306599 A1 | 10/2015 | Khandros et al. |
| 2016/0252495 A1 | 9/2016 | Ricicova et al. |
| 2016/0312165 A1 | 10/2016 | Lowe |

FOREIGN PATENT DOCUMENTS

| | | | |
|---|---|---|---|
| WO | 2005/007796 A2 | 1/2005 | |
| WO | 2008/131048 A2 | 10/2008 | |
| WO | 2009061392 A1 | 5/2009 | |
| WO | 2010/147078 A1 | 12/2010 | |
| WO | WO 2015/061462 A1 * | 4/2015 | .............. C12M 1/24 |
| WO | WO 2015/061497 A1 * | 4/2015 | .............. C12M 1/24 |
| WO | WO 2015/061506 A1 * | 4/2015 | .............. C12M 1/24 |
| WO | 2015/164847 A1 | 10/2015 | |

OTHER PUBLICATIONS

Paul H. Hung et al., "Continuous Perfusion Microfluidic Cell Culture Array for High-Throughput Cell-Based Assays", Wiley Interscience, www.interscience.wiley.com, Dec. 3, 2004.

Pei Yu Chiou et al., "Massively parallel manipulation of single cells and microparticles using optical images", Nature, vol. 436, Jul. 21, 2005, pp. 370-372.

Changqing Yi et al., "Microfluidics technology for manipulation and analysis of biological cells", Analytica Chimica ACTA, vol. 560 (2006), pp. 1-23.

P. Sajeesh et al., "Particle separation and sorting in microfluidic devices: a review", Microfluid Nanofluid (2014) vol. 17, pp. 1-52.

Himali Somaweera et al., "Generation of a Chemical Gradient Across an Array of 256 Cell Cultures in a Single Chip", Analyst, Oct. 7, 2013, vol. 138, pp. 1-14.

International Search Report and Written Opinion issued in International Application No. PCT/US2016/065452 dated Feb. 16, 2017.

Beebe et al., Functional Hydrogel Structures for Autonomous Flow Control inside Microfluidic Channels, Nature 404:588-90 (2000).

Betre et al., Characterization of a Genetically Engineered Polypeptide for Cartilaginous Tissue Repair, Biomacromolecules 3:910-16 (2002).

Chiou et al., Massively parallel manipulation of single cells and microparticles using optical images, Nature 436:370-73 (2005).

Fuchs, Lab on a Chip 6:121-26 (2006).

Nevill et al., Integrated microfluidic cell culture and lysis on a chip, Lab on a Chip 7:1689-95 (2007).

Jongpaiboonkit et al., An adaptable hydrogel array format for 3-dimensional cell culture and analysis, Biomaterials 29:3346-3356 (2008).

Chow et al., Peptide-based polymers in biomedicine and biotechnology, Materials Science and Engineering 62:125-155 (2008).

Valley et al., Optoelectronic Tweezers as a Tool for Parallel Single-Cell Manipulation and Stimulation, IEEE Transactions on Biomedical Circuits and Systems 3(6):424-30 (2009).

Fairbanks et al., Photoinitiated Polymerization of PEG-diacrylate with lithium phenyl-2,4,6-trimethylbenzoylphosphinate: polymerization rate and cytocompatibility, Biomaterials, 30(35): 6702-6707 (2009).

Lee et al., Development of Macroporous PEG Hydrogel Arrays within Microfluidic Channels, Biomacromolecules 13:11(12): 3316-3324 (2010).

Chung et al., Imaging single-cell signaling dynamics with a deterministic high-density single-cell trap array, Anal. Chem.83(18):7044-7052 (2011).

(56) References Cited

OTHER PUBLICATIONS

Vats et al., Dynamic Manipulation of Hydrogels to Control Cell Behavior: A Review, Tissue Engineering: Part B 19(6): 455-469 (2013).
International Search Report and Written Opinion dated Feb. 16, 2017 in International Application No. PCT/US2016/065426 (14 pages).
International Preliminary Report on Patentability dated Jun. 21, 2018 in International Application No. PCT/US2016/065426 (12 pages).
Singapore Office Action dated Aug. 7, 2019 in Singapore Patent Application No. 11201804275T (8 pages).
Folk, Chris, et al. "Hydrogel microvalves with short response time." In 226th American Chemical Society National Meeting, New York, 2003.
Meng, H. And Li, G., "A review of stimuli-responsive shape memory polymer composites" Polymer, vol. 54, No. 9, pp.2199-2221, 2013.

* cited by examiner

IN SITU-GENERATED MICROFLUIDIC ASSAY STRUCTURES, RELATED KITS, AND METHODS OF USE THEREOF

This application is a non-provisional application claiming the benefit under 35 U.S.C. 119(e) of U.S. Provisional Application No. 62/264,665, filed on Dec. 8, 2015, U.S. Provisional Application No. 62/333,821, filed on May 9, 2016, and of U.S. Provisional Application No. 62/418,625, filed on Nov. 7, 2016, each of which disclosures is herein incorporated by reference in its entirety.

BACKGROUND OF THE INVENTION

In biosciences and related fields, it can be useful to have the ability to assay micro-objects within a microfluidic device. Some embodiments of the present disclosure include apparatuses and processes for in-situ generation of microfluidic capture structures.

SUMMARY OF THE INVENTION

In one aspect, a microfluidic device for assaying micro-objects is provided, including an enclosure having a substrate and microfluidic circuit material, the enclosure defining a flow region located within the enclosure; and at least one capture structure disposed within the enclosure, where the at least one capture structure includes a solidified polymer network, and wherein the solidified polymer network includes an assay reagent and/or assay analyte. In various embodiments, the enclosure of the microfluidic device may include at least one sequestration pen, and the at least one capture structure may be disposed within the at least one sequestration pen. The at least one sequestration pen may have an isolation region and a connection region, where the connection region may have a proximal opening to the flow region and a distal opening to the isolation region. In some embodiments, a plurality of capture structures (e.g., 2, 3, 4, etc.) are disposed within the isolation region of the sequestration pen. In various embodiment, the microfluidic device may include a cover.

In another aspect, a method is provided for assaying a micro-object in a microfluidic device having at least a first in situ-generated capture structure, the method including: disposing a micro-object within the microfluidic device in a region proximal to the first in situ-generated capture structure, where the in situ-generated capture structure includes a solidified polymer network, and further where the solidified polymer network includes an assay reagent. The micro-object, such as a biological cell, is allowed to release or produce an analyte; and the analyte and the assay reagent are allowed to interact. The interaction of the analyte and the assay reagent is detected.

In another aspect, a method is provided for preparing a microfluidic device including at least a first in situ-generated capture structure, the method including: providing the microfluidic device, where the microfluidic device comprises an enclosure including a substrate, microfluidic circuit material, and, optionally, a cover, the enclosure defining a flow region; introducing a first flowable functionalized pre-polymer into the flow region; and activating solidification of the first flowable functionalized pre-polymer at at least one selected area within the enclosure, thereby forming the at least a first in situ-generated capture structure therein. The in situ-generated capture structure can be formed in the flow region. Alternatively, or in addition, the enclosure can include at least one sequestration pen fluidically connected to the flow region, and the in situ-generated capture structure can be formed in the sequestration pen (e.g., an isolation region within the sequestration pen). The step of activating solidification of the first flowable functionalized pre-polymer can be performed at a plurality of selected areas within the enclosure, including within a plurality of sequestration pens and/or at a plurality of selected areas within each of one or more sequestration pens.

In yet another aspect, a kit is provided, including: a microfluidic device having an enclosure including a substrate, microfluidic circuit material, and, optionally, a cover, where the enclosure defines a flow region; and a functionalized pre-polymer that can be controllably activated to form a solidified polymer network. The kit can further include an assay reagent, which may be part of the functionalized pre-polymer, mixed with the functionalized pre-polymer, or provided separately from the functionalized pre-polymer (e.g., in a separate vial, tube, etc.). Alternatively, a kit is provided including: a microfluidic device having an enclosure including a substrate, microfluidic circuit material, and, optionally, a cover, where the enclosure defines a flow region; and at least one in situ-generated capture structure disposed within the enclosure, wherein the at least one in situ-generated capture structure includes a solidified polymer network. The kit can further include an assay reagent, which may be integral to or associated with the in situ-generated capture structure or which may be provided separately (e.g., in a vial, tube, etc.). The microfluidic device in either kit can include at least one sequestration pen within the enclosure. For kits in which the in situ-generated capture structure is already disposed within the microfluidic device, the in situ-generated capture structure can be located within the flow region, a sequestration pen of the microfluidic device (e.g., an isolation region within the sequestration pen), or both.

DETAILED DESCRIPTION OF THE INVENTION

Figure 1A:
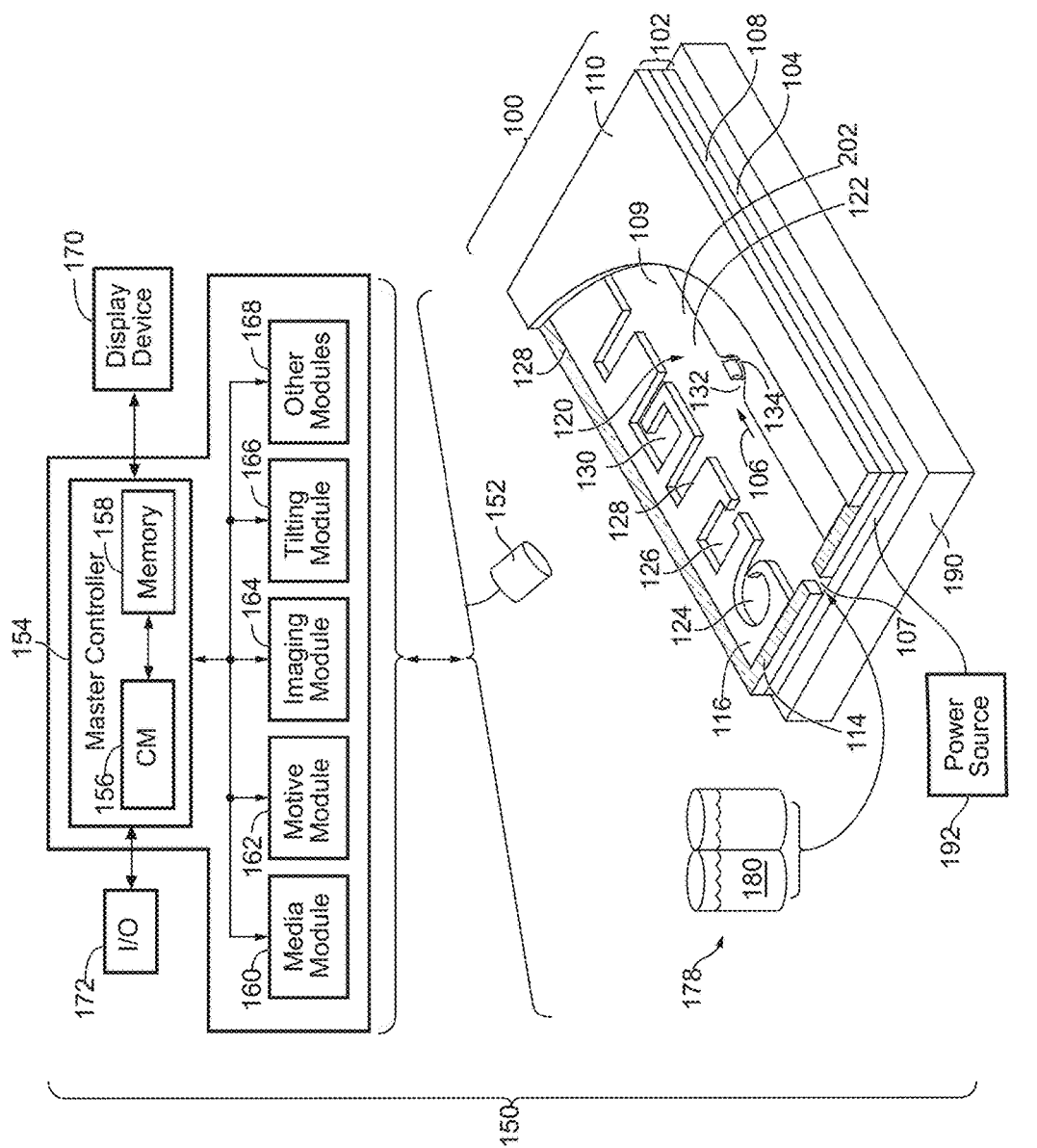
FIG. 1A illustrates an example of a system for use with a microfluidic device and associated control equipment according to some embodiments of the disclosure.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 μL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 μL. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 μL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/ circuit elements can be, for example, the connection region and the isolation region of a microfluidic sequestration pen.

As used herein, the term "constriction" refers generally to a narrowing of a width of a circuit element (or an interface between two circuit elements) in a microfluidic device. The constriction can be located, for example, at the interface between the isolation region and the connection region of a microfluidic sequestration pen of the instant disclosure.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein, "capture moiety" is a chemical or biological species, functionality, or motif that provides a recognition site for a micro-object. A selected class of micro-objects may recognize the in situ-generated capture moiety and may bind or have an affinity for the in situ-generated capture moiety. Non-limiting examples include antigens, antibodies, and cell surface binding motifs.

As used herein, "flowable polymer" is a polymer monomer or macromer that is soluble or dispersible within a fluidic medium (e.g., a pre-polymer solution). The flowable polymer may be input into a microfluidic flow region and flow with other components of a fluidic medium therein.

As used herein, "photoinitiated polymer" refers to a polymer (or a monomeric molecule that can be used to generate the polymer) that upon exposure to light, is capable of crosslinking covalently, forming specific covalent bonds, changing regiochemistry around a rigidified chemical motif, or forming ion pairs which cause a change in physical state, and thereby forming a polymer network. In some instances, a photoinitiated polymer may include a polymer segment bound to one or more chemical moieties capable of crosslinking covalently, forming specific covalent bonds, changing regiochemistry around a rigidified chemical motif, or forming ion pairs which cause a change in physical state. In some instances, a photoinitiated polymer may require a photoactivatable radical initiator to initiate formation of the polymer network (e.g., via polymerization of the polymer).

As used herein, "antibody" refers to an immunoglobulin (Ig) and includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device. The micro-object may still be capable of motion within an in situ-generated capture structure.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices with In Situ-Generated Capture Structures.

It can be advantageous when performing assays upon a micro-object within a microfluidic device that such assays may incorporate an assay analyte or assay reagent that is affixed (e.g. by adhering the assay analyte or assay reagent, or limiting the motion and/or diffusion of the assay analyte or assay reagent) to a specific area and/or feature of the microfluidic circuit, such as a sequestration pen, a trap, or a portion of a flow region, including but not limited to a microfluidic channel. In some instances, the assay analyte or assay reagent may be affixed to a specific portion of the microfluidic device (e.g., a portion of a sequestration pen) using a polymer network. The solidified polymer network may be generated in situ at a selected location. For example, structured light may be used to generate a solidified network of polymers through a light-induced polymerization/cross-linking reaction that solidifies the polymers by cross linking the polymers into a network. The solidified polymer network can be reacted with (either during or after formation of the solidified polymer network) an assay reagent or assay analyte, thereby forming an in situ-generated capture structure comprising the assay reagent or assay analyte. The assay reagent or assay analyte can, in this manner, be maintained within, or at least in close proximity to the surface of, the solidified polymer network, thereby optimizing the assay (e.g., by concentrating the assay signal in one or more pre-defined locations).

It has been surprisingly discovered that a wide variety of capture structures can be generated in-situ within a microfluidic (or nanofluidic) device as described herein. Microfluidic devices, compositions and methods of use for these classes of devices having in situ-generated capture structures are described herein.

A microfluidic device 400 may be provided, including an enclosure comprising a substrate, and microfluidic circuit material 260, the enclosure defining a flow region (e.g., flow channel 410) and at least one sequestration pen 430, each located within the enclosure (not shown); and at least one in situ-generated capture structure 404 disposed within the enclosure, wherein the at least one capture structure 404 comprises a solidified polymer network. The microfluidic circuit material 260 may define the walls of the flow region, and may define other microfluidic circuit elements within the enclosure. In some embodiments, the microfluidic device 400 may include a cover (not shown). In various embodiments, the microfluidic device may include at least one sequestration pen 430, which may also be formed of microfluidic circuit material 260. In some embodiments, the at least one in situ-generated capture structure 404 may be disposed within the at least one sequestration pen 430. The microfluidic device may further include a plurality of sequestration pens within the enclosure. The at least one in situ-generated capture structure is configured to be capable of capturing a biological product of a micro-object and/or be acted upon by the micro-object or a biological product of the micro-object. The at least one in situ-generated capture structure may include an assay reagent or assay analyte, or may be configured to accept an assay reagent or assay analyte (e.g., may include functionalized sites configured to react with a functionalized assay reagent or assay analyte). An assay reagent may be configured to capture a biological product of the micro-object. An assay analyte may be configured to capture a biological product of a micro-object or to be acted upon by a micro-object or a biological product of the micro-object.

Figure 4A:
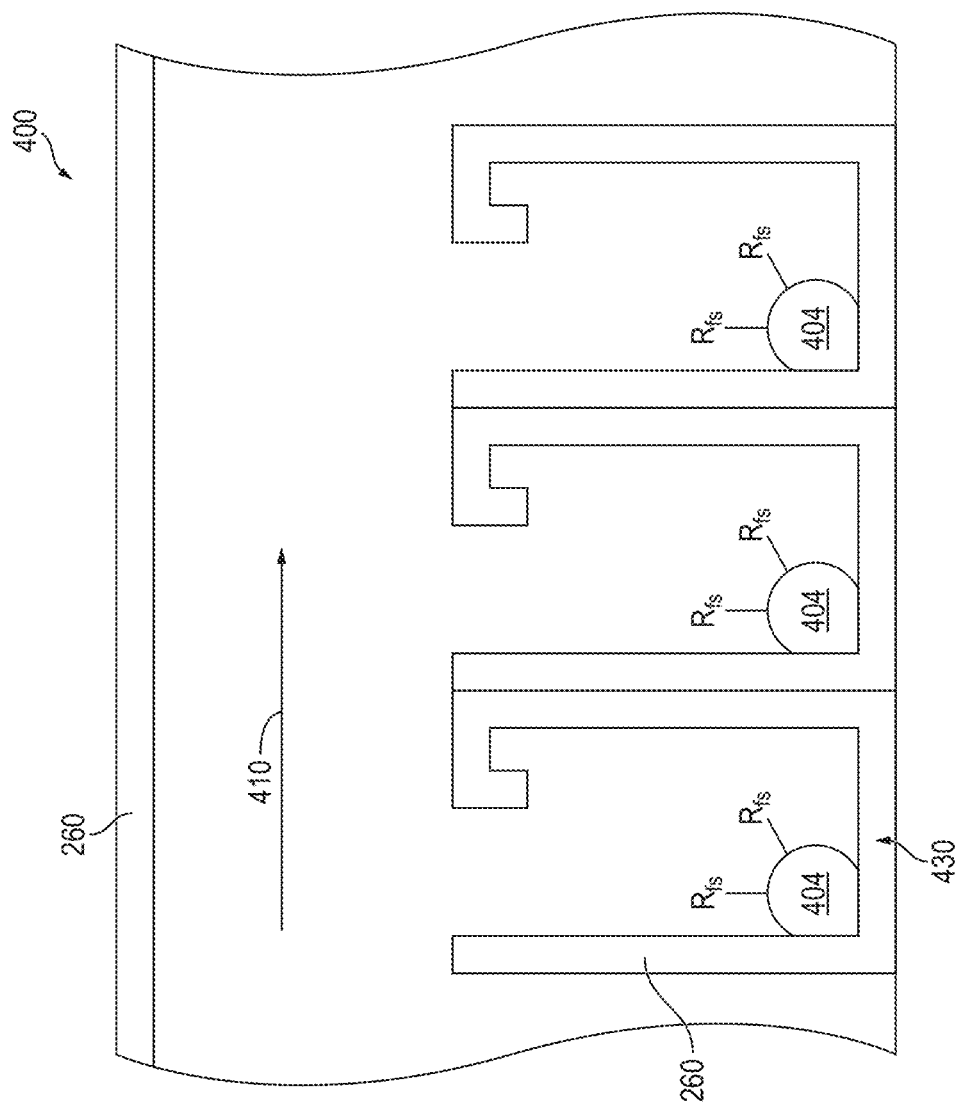
FIGS. 4A-4B are graphical representations of embodiments of in situ-generated assay structures.

A portion of microfluidic device 400 is shown in FIG. 4A. The at least one sequestration pen 430 may be fluidically connected to the flow region (e.g., flow channel 410). The at least one sequestration pen 430 may include an isolation region and a connection region, and have any set of dimensions as described above for any sequestration pen 124, 126, 128, 130, 224, 226, 228, 266 where the connection region has a proximal opening to the flow region flow channel 410) and a distal opening to the isolation region. The flow region (e.g., flow channel 410) of the microfluidic device may include a microfluidic channel 410. The proximal opening of the sequestration pen to the flow region (e.g., flow channel 410) may be oriented substantially parallel to a flow of fluidic medium in the flow region (not shown). Exchange of components of between fluidic media in the flow region and fluidic media within the isolation region of the sequestration pen may occur substantially only by diffusion. The at least one in situ-generated capture structure 404 may be disposed within the isolation region of the sequestration pen 430.

The at least one in situ-generated capture structure 404 may be located within a connection region or an isolation region of a sequestration pen. The in situ-generated capture structure 404 may further be selectively formed to be in a location of the isolation region of the sequestration pen such that cells may be imported into the isolation region without hindrance. The at least one in situ-generated capture structure 404 may be located within the isolation region such that cells may be exported out of the isolation region without hindrance from the in situ-generated capture structure 404. The microfluidic device may include a plurality of sequestration pens 430, which may be configured in any suitable arrangement as described herein, in any combination. When a microfluidic channel and a plurality of sequestration pens are present, the plurality of sequestration pens may be aligned in a row, with each sequestration pen of the plurality opening off of one side of the microfluidic channel 410. The proximal openings of each sequestration pen of the plurality may open to the microfluidic channel 410 in a common direction.

Figure 4B:
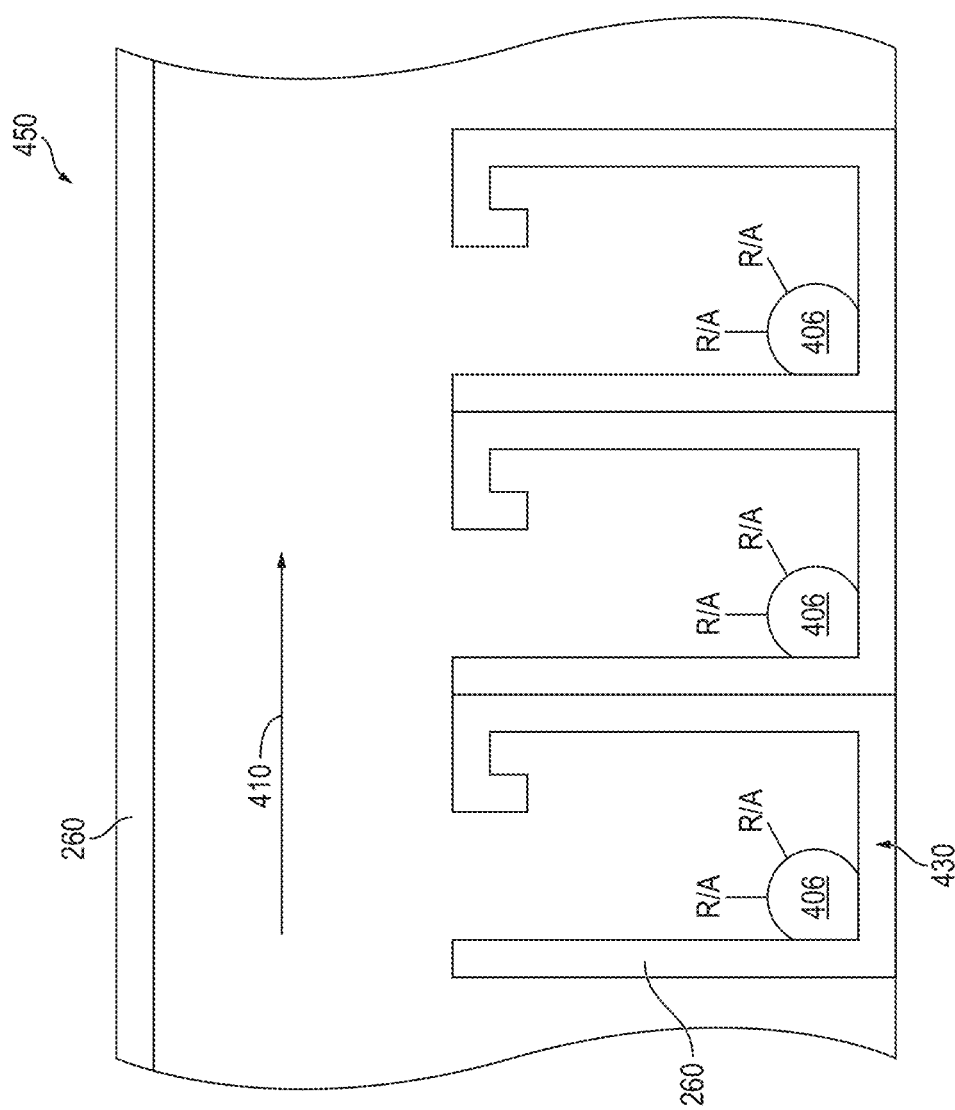
Figure 4C:
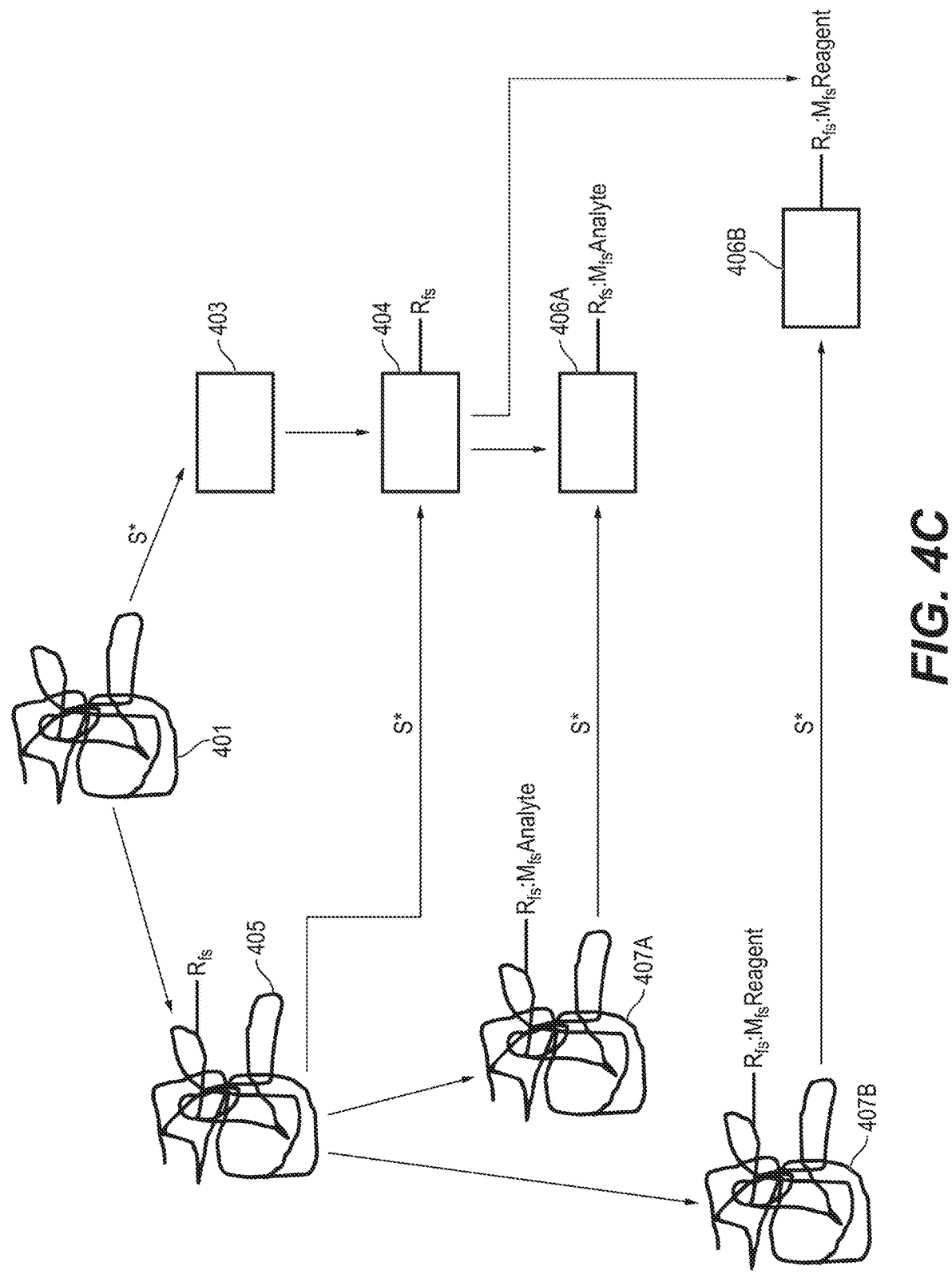
FIGS. 4C and 4D are schematic representations of processes for generating an assay structure in situ.
Figure 4D:
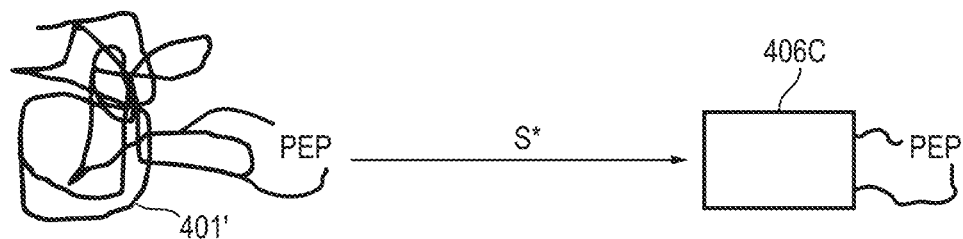

In another embodiment, a microfluidic device 450 is provided, a portion of which is as shown in FIG. 4B, including an enclosure comprising a substrate and a cover, the enclosure defining a flow region (e.g., flow channel 410) and at least one sequestration pen 430, each located within the enclosure (not shown); and at least one in situ-generated capture structure 406 disposed within the at least one sequestration pen 430, wherein the at least one in situ-generated capture structure 406 comprises a solidified polymer network which further comprises an assay reagent or assay analyte (R/A, e.g., 406B or 406A of FIGS. 4C and 4D).

Substrate.

The substrate of the microfluidic device 400, 450 may further include a configuration for generating dielectrophoresis (DEP) forces within the enclosure (not shown). The microfluidic device substrate having a DEP configuration may include any DEP configuration as described herein. The DEP forces may be optically actuated. In other embodiments, the substrate of the microfluidic device 400, 450 may be configured to include an opto-electrowetting configuration (not shown). In some embodiments, the opto-electrowetting substrate may be optically actuated. In yet other embodiments, the microfluidic device 400, 450 may include a combination of a substrate configured to generate DEP forces and a substrate configured to generate electrowetting forces, each of which are optically actuated.

In some embodiments, the cover of the microfluidic device 400, 450 may be substantially transparent to a fluorescent, colorimetric, or luminescent signal from the one or more in situ-generated capture structures.

In various embodiments, the microfluidic device having at least one capture structure 400, 450 may have a dynamic coating or a conditioned surface which enhances cell growth, viability, portability and any combination thereof, as described above. Any suitable dynamic coating or conditioned surface may be used. In some embodiments, a conditioned surface may include a covalently modified surface, which may be any suitable covalently modified surface as described herein. A covalently modified surface may be present before solidifying the polymer network of the in situ-generated capture structure. If a dynamic coating is used, it may be introduced before or after solidifying the polymer network of the in situ-generated capture structure.

Microfluidic device 400, 450 may have any other components, features or configurations as described for microfluidic devices 100, 200, 230, 250, 280, 290, 320, 500, 700 described herein, in any combination.

In Situ-Generated Capture Structure Including a Solidified Polymer Network.

The solidified polymer network of the in situ-generated capture structures 404, 406 (FIGS. 4A, 4B) may include a photoinitiated polymer, and may be solidified in situ. In some embodiments, the solidified polymer network does not include a silicone polymer. In some embodiments, the solidified polymer network does not include silicon. The solidified polymer network may be made from any suitable polymer and may be any polymer as described herein.

Functionalized Sites.

The solidified polymer network of the at least one in situ-generated capture structure 404 of microfluidic device 400 may include one or more functionalized sites. In some embodiments, the solidified polymer network of the in situ-generated capture structure may include two or more functionalized sites. The functionalized sites may be adhered (which may include non-specific non-covalent binding or may include non-covalent binding via a specific binding pair or motif) to the solidified polymer network. In other embodiments, the functionalized sites of the solidified polymer network may be covalently bound to the polymer(s) of the solidified polymer network.

The functionalized sites may include a reactive moiety $R_{fs}$ permitting an assay reagent or assay analyte to be introduced thereto. The reactive moiety $R_{fs}$ may provide a covalent or non-covalent mode of reaction, including association (e.g., chelation, for one non-limiting example), binding (e.g., non-covalent binding such as between biotin and streptavidin or an antibody/antigen binding pair), or reaction (e.g., forming a covalent bond such as between Click reaction pairs). For simplicity, the term binding may be used to encompass all three types of interactions, but one or more of these interactions may be preferred in specific embodiments. In some embodiments, the reactive moiety $R_{fs}$ of the one or more functionalized sites may be biotin, avidin or streptavidin. In other embodiments, the reactive moiety $R_{fs}$ of the one or more functionalized sites may include a chelating moiety or an oligonucleotide hybridization sequence. In some embodiments, the one or more functionalized sites of the solidified polymer network may be introduced after solidification of the polymer network (e.g., a non-specifically adhered species containing a reactive moiety $R_{fs}$ may be flowed into the sequestration pen and permitted to contact the solidified polymer network for a period of time to adhere sufficient numbers of the species containing reactive moiety $R_{fs}$ for suitable assay conditions) as shown schematically for the conversion of in situ-generated capture structure 403 including a solidified polymer network, to in situ-generated capture structure 404 including a solidified polymer network having at least one functionalized site. In other embodiments, the one or more functionalized sites including a reactive moiety $R_{fs}$ are introduced to the prepolymer 401 prior to solidification of the polymer network, as shown schematically in FIGS. 4C and 4D.

Microfluidic device 450, having at least in situ-generated one capture structure 406 which includes an assay reagent or assay analyte (e.g., R/A of 406 of FIG. 4B), may contain one or more functionalized sites each having a reactive moiety $R_{fs}$ already associated, bound or reacted with an assay reagent or assay analyte. The reactive moiety $R_{fs}$ may be selected from any reactive moiety as described above for microfluidic device 400 and respective in situ-generated capture structure 404. As above, the term binding may be used to encompass all three types of interactions, but one or more of these interactions may be preferred in specific embodiments. Binding of the assay reagent or assay analyte may be conducted either prior to solidifying the polymer network or subsequent to solidification, as described below and shown in FIG. 4C.

In some embodiments, the one or more functionalized sites of a solidified polymer network of an in situ-generated capture structure 404, 406 may all include the same reactive moiety $R_{fs}$. In other embodiments, the one or more functionalized sites of a solidified polymer network of an in situ-generated capture structure 404, 406 may include different $R_{fs}$. In some other embodiments, more than one type of polymer may be used to form the solidified polymer network and each polymer may have the same or different functionalized sites (e.g., reactive moieties $R_{fs}$ attached or adhered thereto).

Assay Reagent or Assay Analyte.

The solidified polymer network of the at least one in situ-generated capture structure 406 may further include an assay reagent and/or assay analyte (FIGS. 4B, 4C, 4D). The in situ-generated capture structure 406 of the microfluidic device 450 may be provided already including an assay reagent or an assay analyte bound to the solidified polymer network. Alternatively, the microfluidic device 400 may have an in situ-generated capture structure 404 (FIG. 4A) configured to associate, bind or react with the assay reagent or assay analyte to provide an in situ-generated capture structure 406 including an assay reagent or assay analyte (R/A of FIG. 4B), and shown in more schematic detail in FIG. 4C. In yet another alternative, the solidified polymer network and its associated assay reagent or assay analyte may be introduced before the start of the assay experiment itself. The assay reagent or assay analyte may be configured to be covalently or non-covalently bound to the one or more functionalized sites of the solidified polymer network. The assay reagent or assay analyte may be introduced during the initial formation of the in situ-generated capture structure, for example, by being covalently bound to the flowable polymer solution (e.g., already incorporated within the pre-polymer). One non-limiting example may be incorporation of recognition motifs such as an RGD motif, which may be recognized by integrins on a target biological cell.

Alternatively, the assay reagent or assay analyte may be flowed into the microfluidic device 400 having an in situ-generated capture structure 404 including one or more functionalized sites (e.g., at some time after the solidified polymer network has been solidified). The assay reagent or assay analyte may include a functional moiety $M_{fs}$ configured to associate, bind or react with $R_{fs}$ of the functionalized sites of the solidified polymer network of the at least one in situ-generated capture structure 404 to generate the at least one in situ-generated capture structure 406. As above, the term binding may be used to encompass all three types of interactions, but one or more of these interactions may be preferred in specific embodiments. Any suitable functional moiety $M_{fs}$ may be used. For example, a chelating substrate $M_{fs}$ of an assay reagent or assay analyte may be chelated by a chelating ligand $R_{fs}$ of the functionalized sites of the solidified polymer network of capture structure 404. A functional moiety $M_{fs}$ may include biotin or streptavidin, to bind non-covalently with a respective avidin, streptavidin or biotin $R_{fs}$ of the functionalized sites of capture structure 404. Alternatively, a functional moiety $M_{fs}$ may be configured to react covalently with the $R_{fs}$ of the functionalized sites of the solidified polymer network. For example, a functional moiety $M_{fs}$ may be an azide and may react covalently with an alkynyl functionality of a corresponding Click reaction pair of a functionalized site of an in situ-generated capture structure 404.

In some embodiments of the microfluidic device including at least one in situ-generated capture structure, the assay reagent or assay analyte may include a detectable label. The detectable label of the assay reagent or assay analyte may be a fluorescent, colorimetric, or luminescent label. In some embodiments, the detectable label may be a fluorescent label. In some embodiments, when the assay reagent or assay analyte includes a detectable label, the label is not detectable until the assay is proceeding, and the detectable label is generated or liberated from the assay reagent or assay analyte.

Methods of Introducing Solidified Polymer Networks which May Include a Reactive Moiety and/or Assay Reagent or Assay Analyte.

Preparation of the solidified polymer network of the at least one in situ-generated capture structure may be performed variously, as shown schematically in FIGS. 4C and 4D. In one route shown in FIG. 4C, one or more prepolymers 401 may be modified to provide a prepolymer 405 containing at least one functionalized site including a reactive moiety $R_{fs}$. This unsolidified prepolymer 405 may subsequently be flowed into the enclosure of the microfluidic device, and solidified in-situ to provide an in situ-generated capture structure 404, which may optionally include introducing the flowable pre-polymer into a sequestration pen. Alternatively, the prepolymer 405 having at least one functionalized site including a reactive moiety $R_{fs}$, may be reacted with an assay analyte having a functional moiety $M_{fs}$ to provide a prepolymer 407A already containing an assay analyte. This prepolymer 407A, already incorporating an assay analyte, may subsequently be flowed into the microfluidic device, and optionally to the sequestration pen, and may be solidified in situ to provide an in situ-generated capture structure 406A having an assay analyte.

In another embodiment, the prepolymer 405 having at least one functional site including a reactive moiety $R_{fs}$ is reacted with an assay reagent having a functional moiety $M_{fs}$ to provide a prepolymer 407B already containing an assay reagent. The prepolymer 407B may subsequently be flowed into the enclosure of the microfluidic device, and optionally introduced to the sequestration pen, and solidified in situ to provide an in situ-generated capture structure 406B including an assay reagent.

In yet another embodiment, prepolymer 401 itself may be flowed into the enclosure of the microfluidic device, and optionally to the sequestration pen, and may be solidified in situ to provide the solidified polymer network 403 forming part of the in situ-generated capture structure. The solidified polymer network may be modified to introduce at least one functional site having a reactive group $R_{fs}$ by flowing in a material to adhere or bond to the solidified polymer network, thereby providing a solidified polymer network including at least one reactive group $R_{fs}$ (e.g., in situ-generated capture structure 404). In situ-generated capture structure 404 may be further modified by flowing in an assay analyte having a functional moiety $M_{fs}$, which reacts with the $R_{fs}$ of capture structure 404 to provide an in situ-generated capture structure 406A containing an assay analyte. Alternatively, in situ-generated capture structure 404 may be further modified by flowing in an assay reagent having a functional moiety $M_{fs}$, which reacts with the $R_{fs}$ of capture structure 404 to provide an in situ-generated capture structure 406B containing an assay reagent.

In yet another embodiment, shown in FIG. 4D, prepolymer 401' is prepared having an assay analyte or assay reagent already incorporated into the prepolymer, such as, for example, a peptide segment including an RGD or a proteinase substrate (e.g., PEP in FIG. 4D) motif. Prepolymer 401' may be flowed into the enclosure of the microfluidic device, and optionally to the sequestration pen, and solidified in situ to provide an in situ-generated capture structure 406C, having an assay reagent or assay analyte incorporated within the solidified polymer network.

Methods of introducing the in situ-generated capture structures are described in fuller detail below.

Assay Reagent of the In Situ-Generated Capture Structure.

The assay reagent may include a protein, a nucleic acid, an organic molecule, and/or a saccharide. The assay reagent may include an in situ-generated capture oligonucleotide, which can hybridize to a nucleic acid of interest. The oligonucleotide may be synthetically produced or may be produced by a biological cell. The oligonucleotide may be further processed after biological production for size or to introduce other functionality. A protein assay reagent may include, but is not limited to an antibody, a structural protein, a cell surface marker, or a cytokine. An organic molecule assay reagent may include a synthetic, semi-synthetic or biologically produced organic molecule having a molecular weight of about 2000 Da or less. An organic molecule may include a chelation substrate, a chelation ligand, a peptide, or a non-peptidic organic molecule. In some embodiments, the assay reagent may include a combination of two or more of a protein, nucleic acid, an organic molecule, or a saccharide. In some embodiments, the assay reagent may include an antibody or a fragment thereof. In other embodiments, the assay reagent may include an antigen. In some embodiments, the antigen assay reagent may be a cytokine, including but not limited to tumor necrosis factor alpha (TNF alpha), interferon alpha (IFN-alpha), Interleukin 2 (IL-2) or IFN gamma.

In some embodiments, when the assay reagent includes an antibody, the assay reagent antibody may specifically bind to a tumor antigen, which may be any tumor antigen as described herein. In other embodiments, the assay reagent antibody may specifically bind to a cytokine, which may be any suitable cytokine, including but not limited to tumor necrosis factor alpha (TNF alpha), interferon alpha (IFN-alpha), Interleukin 2 (IL-2) or IFN gamma.

In some embodiments, when the assay reagent includes an antigen, the antigen reagent may be a tumor antigen. The tumor antigen reagent may be a tumor specific antigen or a tumor associated antigen. A non-limiting list of tumor antigens that may be used as an assay reagent include WT1, MUC1, LMP2, HPV E6 E7, EGFRvIII, HER-2/neu, MAGE A3, p53 nonmutant, NY-ESO-1, PSMA, GD2, CEA, MelanA/MART1, Ras mutant, gp100, p53 mutant, Proteinase 3 (PR1), bcr-able. Tyrosinase, Survivin, PSA, hTERT, EphA2, PEP, ML-IAP, AFP, EpCAM, ERG (TMPRSS2 ETS fusion gene, NA17, PAX3, ALK, Androgen receptor, cyclin B1, polysialic acid, MYCN, RhoC, TRP-2, GD3, fucosyl GM1, Mesothelin, or PSCA.

Figure 5A:
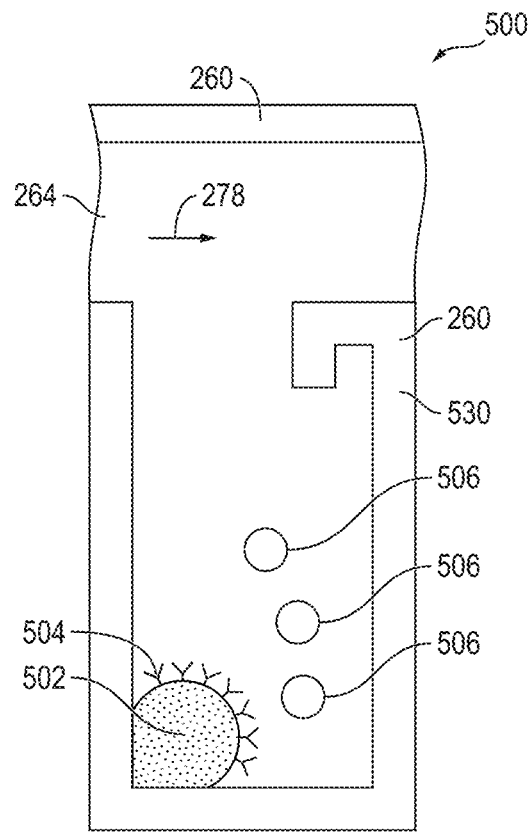
FIGS. 5A to 5E are graphical representations of an embodiment of an in situ-generated assay structure of the disclosure, and its use in an assay detecting cytokine secreted by a biological micro-object.

FIG. 5A shows one example of a microfluidic device 500, having at least one sequestration pen 530 opening to microfluidic channel 264. The sequestration pen 530 has one in situ generated capture structure 502 having a solidified polymer network which includes an assay reagent 504, shown here as an antibody.

These examples of an assay reagent are in no way limiting, and may be any suitable assay reagent as one of skill may select.

Assay Analyte of the In Situ-Generated Capture Structure.

An assay analyte may bind to the solidified polymer network of the in situ-generated capture structure via a covalent or non-covalent binding interaction with the assay reagent. In some of the embodiments when an assay analyte is bound to/incorporated within the in situ-generated capture structure, the assay analyte also includes a detectable label such as a fluorescent, luminescent or visibly colored dye label. The assay analyte may include a protein, a nucleic acid, an organic molecule (as described above), and/or a saccharide. In some embodiments, the assay analyte may include a combination of two or more of a protein, nucleic acid, an organic molecule, or a saccharide. A protein assay analyte may include, but is not limited to an antibody, a structural protein, a cell surface marker, or a cytokine.

In some embodiments, the assay analyte may include an antibody or a fragment thereof. In one non-limiting example, it is not uncommon when studying antibodies to screen for an "anti-idiotype" antibody that binds the binding site of a first antibody. The anti-idiotype antibody can mimic the antigen bound by the first antibody, and thereby can be used to (1) model the antigen bound by the first antibody, or (2) vaccinate an animal (thus creating new antibodies that are similar to the first antibody). The anti-idiotype antibody can therefore be viewed as an assay analyte in this context, or may alternatively be considered an assay reagent and used accordingly.

In other embodiments, the protein assay analyte may be an antigen non-covalently bound to the in situ-generated capture structure. An organic molecule assay analyte may include a peptide, or a non-peptidic organic molecule. One non-limiting example of an assay analyte is a substrate for a proteinase. The substrate may be a peptidic or a non-peptidic organic molecule. The assay may identify a cell that effectively produces a proteinase of interest, which may be of use for commercial production. Alternatively, the substrate may be the target of a pathogenic proteinase expression and can be used to identify cells having the pathogenic activity.

For example, a matrix metalloproteinase (MMP) substrate (such as, for example, MMP-2, which may have a substrate sequence of Gly-Pro-Gln-Gly-Trp-Gly-Gln, (e.g., PEP)) may be incorporated into an in situ-generated capture structure by any suitable manner such as incorporation within the pre-polymer (e.g, 401') or introduced into a functionalized site of an in situ-generated capture structure (e.g., via a crosslinker, yielding a prepolymer 407A, and/or in situ-generated capture structure 406A). Expression of certain metalloproteinases is associated with metastatic potential and cancer progression. An in situ-generated capture structure incorporating an MMP substrate motif may be used to identify cells expressing the MMP. If the MMP substrate is part of the solidified polymer network of the in situ-generated capture structure 406C (See FIG. 4D), the solidified polymer network may be eroded and loss of the network may be monitored. For example, the solidified polymer network incorporating a MMP substrate motif may further include a fluorescent label that is liberated as the proteinase activity continues. Loss of signal within the solidified polymer network may be monitored or gain of signal within the liquid medium within the sequestration pen may be monitored. Substrates that may be bound or incorporated within the solidified polymer network of the in situ-generated capture structure are not limited to any specific type of substrates but may be any suitable substrate for which assay may be desired.

Another protease substrate that may be a useful assay analyte to be bound or incorporated within an in situ-generated capture structure may be a furin substrate. Furin (proprotein convertase having serine endoprotease activity) may be involved in differentiation of T cells to a Th1 phenotype. The assay may be performed in various ways using the in situ-generated capture structure as described herein, but in one embodiment, a peptide may incorporate a cleavage motif for Furin, a functional moiety $M_{fs}$, such as biotin, which permits attachment to functional sites within the solidified polymer network of the in situ-generated capture structure, and a fluorophore attached to a location within the peptide which will be released upon cleavage by furin. Cells expressing furin activity would release fluorescence from the in situ-generated capture structure, and the loss of signal may be detected and may further be quantitated.

In yet another embodiment, a fluorescently labeled antigen may be embedded, either by adhesion or possibly by another non-covalent mode, within the solidified polymer network of the in situ-generated capture structure 406. An assay may be performed to measure antigen extraction by B cells. As the B cells associate or bind with the solidified polymer network, if the B cell expresses an antibody specific for the antigen, the antigen may be extracted from the solidified polymer network. Higher affinity antibodies may exhibit higher levels of antigen extraction, and hence loss of fluorescent signal from the solidified polymer network of the in situ-generated capture structure.

These examples of an assay analyte are in no way limiting, and the assay analyte may be any suitable assay analyte as one of skill may select Detection Reagent(s).

The result of the interaction between the assay reagent (or analyte) and its intended target may be detected by a detection reagent. The detection reagent may include a detectable label. The detectable label of the detection reagent may include a fluorescent, colorimetric, or luminescent label. In some embodiments, the detection reagent may include at least a first antibody. A detection reagent may include a first antibody that is detectably labelled. In some embodiments, the detection reagent may include a second antibody, where the second antibody may incorporate the detectable label. In some embodiments, where the labeled second antibody is a secondary antibody and binds to the at least first antibody. The first and/or the second antibody may be an IgG antibody. The first and/or the second antibody may be a fragment of an antibody. In other embodiments, the detection reagent may include an intercalating dye. In yet other embodiments, the detection reagent may include a FRET labeled oligonucleotide, which may include but is not limited to a molecular beacon, dual hybridization probe, Scorpion®, or Eclipse® probe. A FRET labeled oligonucleotide probe or probe pair may include fluorescent labels that do not fluoresce until a hybridization event takes place. The detection reagent may be an intercalating dye, including but not limited to phenanthridine or acridine dyes.

Microfluidic Devices Having One or More In Situ-Generated Capture Structures for Multiplexed Assays.

The at least one in situ-generated capture structure in the enclosure, and optionally where the at least one in situ-generated capture structure may be disposed within at least one sequestration pen, of the microfluidic device 400, 450, may be configured to detect more than one interaction (e.g., may have two, three or more different assay reagents or analytes bound to the in situ-generated capture structure), thus providing one mode of conducting multiplexed assays. In some embodiments, a single in situ-generated capture structure, of the enclosure or the at least one sequestration pen, is configured to contain two assay reagents that detect two different analytes (e.g., biological products of a cell).

In other embodiments, the enclosure of the microfluidic device 400, 450 may include two or more in situ-generated capture structures disposed therein. In some embodiments, the at least one sequestration pen of the microfluidic device 400, 450 may include the two or more in situ-generated capture structures disposed therein. The two or more in situ-generated capture structures may be disposed within the isolation region of the sequestration pen. For a microfluidic device 450, a first solidified polymer network of a first in situ-generated capture structure may include a first assay reagent or assay analyte and a second solidified polymer network of a second in situ-generated capture structure may include a second assay reagent or assay analyte, and so on for each additional in situ-generated capture structure in the at least one sequestration pen. For microfluidic device 400, a first solidified polymer network of a first in situ-generated capture structure may include a first type of functionalized sites and a second solidified polymer network of a second in situ-generated capture structure may include a second type of functionalized sites, which can each accept a different kind of assay reagent or assay analyte. In the embodiments of microfluidic devices 400, 450, having multiple in situ-generated capture structures within the enclosure or within the at least one sequestration pen, the first assay reagent or assay analyte may be different from the second assay reagent or assay analyte, and so on for each additional assay reagent or assay analyte. The first in situ-generated capture structure and the second in situ-generated capture structure may be disposed in different locations within the enclosure or, alternatively, within at least one sequestration pen of the microfluidic device. The first in situ-generated capture structure and the in situ-generated second capture structure may be disposed on a first wall and a second wall, respectively of the enclosure or may be located adjacent to one another on the same wall. The first in situ-generated capture structure and the in situ-generated second capture structure may be disposed on a first wall and a second wall, respectively of the sequestration pen, or may be disposed adjacent to each other on a first wall of the sequestration pen.

Figure 7:
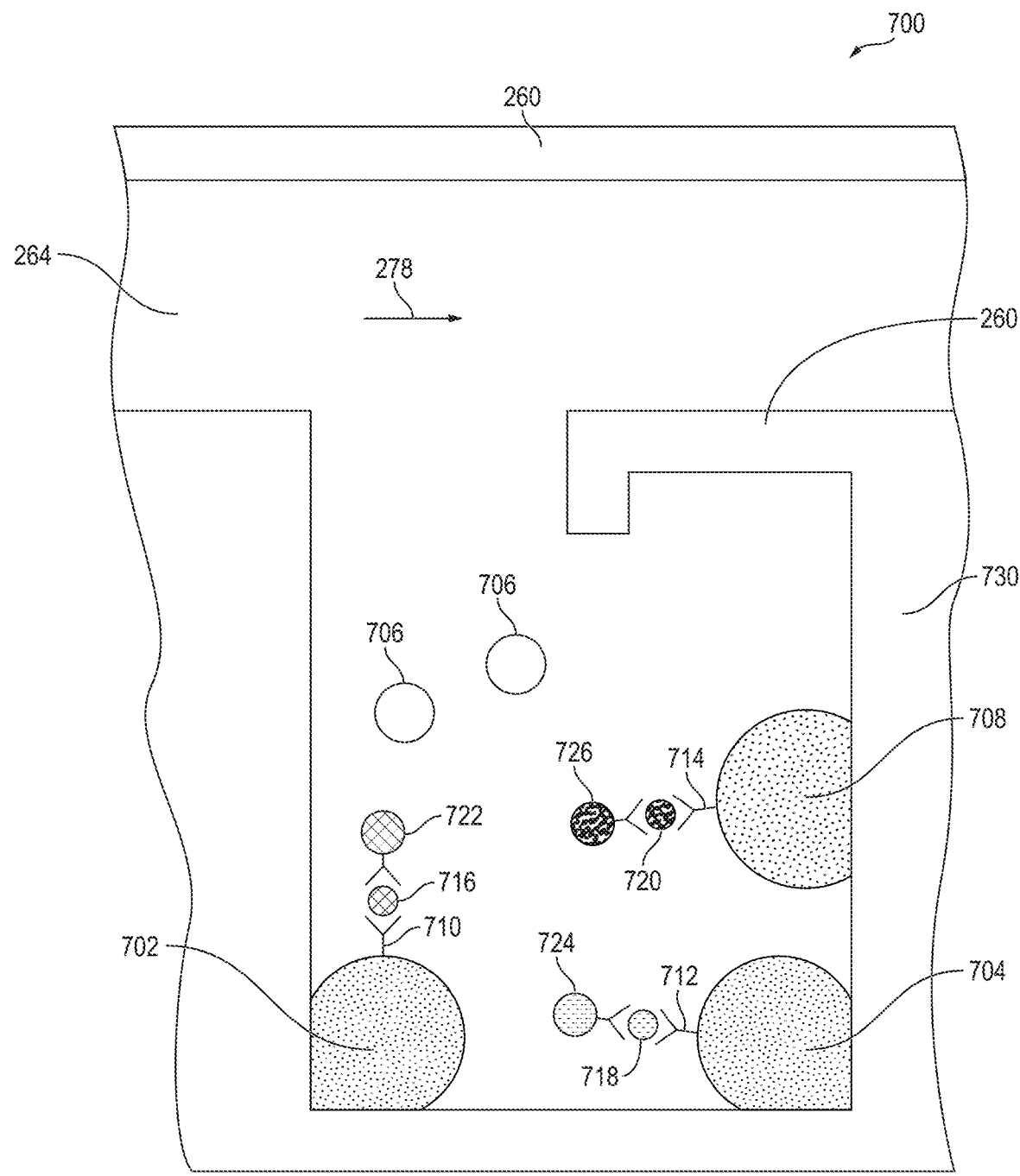
FIG. 7 is a graphical representation of an embodiment of a sequestration pen including multiple in-situ generated assay structures for multiplex assay of a biological cell.

An example of a microfluidic device including at least one sequestration pen, where the sequestration pen includes more than one in situ-generated capture structure is shown in FIG. 7. One portion of microfluidic device 700 is shown, displaying one sequestration pen 730. Microfluidic device 700 may have any combination of components and features of any of the microfluidic devices 100, 200, 230. 250, 280, 290, 400, 450, 500, in any suitable combination as may be selected by one of skill. The sequestration pen 730 may be constructed of the same microfluidic circuit material 260, which also defines channel 264. A first fluidic medium (not shown) may flow with flow 278 in the microfluidic channel 264. Sequestration pen 730 has three capture structures 702, 704, 708 disposed in three physically distinguishable locations within the pen 730. There are two micro-objects 706 loaded into the pen 730, which, in this embodiment, are producing biological products 716, 718, and 720. As few as one micro-object 706 may be present, or there may be a plurality of micro-objects 706, as may be suitable for a selected assay. The biological products 716, 718, 720 may be all different or may be the same biological product which is assayed for three different characteristics by the assay reagents 710, 712, 714 (which alternatively can be any selection of assay reagent and/or assay analyte) which are included respectively within and/or on capture structures 702, 704, 708, forming in situ capture structures (702 plus 710), (704 plus 712), and (708 plus 714), which are equivalent to in situ-generated capture structure 406 of FIG. 4B, or in situ-generated capture structures 406A and/or 406B of FIG. 4C. The assay reagents 710, 712, 714 are each different from each other and test for either a different biological product or a different characteristic of a biological product. As shown in FIG. 7, the assay reagents 710, 712, 714 are shown as antibodies for ease of viewing, but the multiplexed in situ-generated capture structures are not limited to including only antibody assay reagents, but may be any suitable combination of assay reagents (or assay analytes) as described herein.

Other Properties of the at Least One Capture Structure.

When the in situ-generated capture structure is located within the enclosure, and optionally within the flow region, a size of the in situ-generated capture structure may have any suitable size that may permit flow of the fluidic medium through the flow region. In some embodiments, the in situ-generated capture structure may have a dimension across the flow region (which may be a microfluidic channel) that is less than 80%, 70%, 60%, 50% 40%, 30% 20%, 10%, 5%, 1%, or less of a width of the flow region. The isolation region of the sequestration pen of the microfluidic device may have a width of about 50 microns to about 250 microns, and a width of the in situ-generated capture structure generated therein may be in a range from about ⅛ to about ¾ of the width of the isolation region, or any value therebetween. A width of the in situ-generated capture structure across the isolation region may be in a range of about 5 microns to about 35 microns (or any value therebetween) in an isolation region having a width of about 50 microns or in a range of about 60 microns to about 190 microns (or any value therebetween) in an isolation region having a width of about 250 microns. In various embodiments, the in situ-generated capture structure may be configured to permit exit of a micro-object, including but not limited to a biological micro-object (e.g., a biological cell or embryo) or microbead, from the sequestration pen.

In some embodiments, the in situ-generated capture structure may be porous to a flow of fluidic medium. The solidified polymer network may not be porous to at least a subset of a plurality of micro-objects. In some embodiments, the solidified polymer network is substantially non-porous to micro-object having a diameter of greater than about 1 nm, 2 nm, 10 nm, 100 nm, 250 nm, 500 nm, 600 nm, 700 nm, 800 nm, 900 nm, 1 micron, 2 microns, 3 microns, 4 microns, 5 microns, 6 microns, 7 microns, 8 microns, 9 microns, 10 microns, 11 microns, 12 microns, 13 microns, 14 microns, 15 microns, or more.

In some embodiments, at least a portion of the in situ-generated capture structure may be removable. The in situ-generated capture structure may be at least partially removable by hydrolysis, proteolysis, osmotic change, temperature change, or optical illumination, as discussed below.

Other Features of the Microfluidic Device Having at Least One In Situ-Generated Capture Structure.

The microfluidic device may be any microfluidic device described herein and may include any components, features or dimensions described below in any combination.

In some embodiments, the enclosure of the microfluidic device may further include a selection sector. The selection region may contain the at least one in situ-generated capture structure and at least part of the flow region. The selection sector may be a distinct region of the enclosure of the microfluidic device where assays are performed as described herein.

In some embodiments, the enclosure of the microfluidic device may further include an isolation sector. The isolation sector may be used to maintain, grow and/or expand selected micro-objects, based on the assay results obtained in the assay sector. The isolation sector may include at least one sequestration pen which may be configured like the sequestration pens of the selection sector as described above, but may not have any capture structures located within the sequestration pen. The isolation sector may include a plurality of sequestration pens. The isolation sector may be a distinct region in the enclosure of the microfluidic device that is fluidically connected to the selection sector. The isolation sector may further include a microfluidic channel which is part of the flow region, and wherein each of the at least one sequestration pens opens off of the microfluidic channel. The opening of the at least one sequestration pen of the isolation sector may open laterally from the microfluidic channel.

Polymers for Use in the Solidified Polymer Network of the In Situ-Generated Capture Structure.

In various embodiments of the solidified polymer network of an in situ-generated capture structure, the solidified polymer network may be a synthetic polymer, a modified synthetic polymer, or a light or temperature activatable biological polymer. The functionalized pre-polymer used to form the solidified polymer network may be any of the polymers described herein for use within the solidified polymer network. The biological polymer may be configured to be temperature or light activatable to form a solidified polymer network. In some embodiments, the biological polymer may be modified to incorporate moieties providing the ability to be temperature or light activatable. The synthetic polymer modifications may include size modification motifs, cleavage motifs, reactive terminal moieties, and/or cell recognition motifs.

In some embodiments of the solidified polymer network of an in situ-generated capture structure, the solidified polymer network may include at least one of a polyethylene glycol, modified polyethylene glycol, polylactic acid (PLA), modified polylactic acid, polyglycolic acid (PGA), modified polyglycolic acid, polyacrylamide (PAM), modified polyacrylamide, poly-N-isopropylacrylamide (PNIPAm), modified poly-N-isopropylacrylamide, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, gelatin, modified gelatin, laminin, modified laminin, polysaccharide, modified polysaccharide, or a co-polymer in any combination. In other embodiments, the polymer may include at least one of a polyethylene glycol, modified polyethylene glycol, polylactic acid (PLA), modified polylactic acid, polyglycolic acid (PGA), modified polyglycolic acid, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, laminin, modified laminin, polysaccharide, modified polysaccharide, or a co-polymer in any combination. In yet other embodiments, the polymer may include at least one of a polyethylene glycol, modified polyethylene glycol, polylactic acid (PLA), modified polylactic acid, polyglycolic acid (PGA), modified polyglycolic acid, polyvinyl alcohol (PVA), modified polyvinyl alcohol, polyacrylic acid (PAA), modified polyacrylic acid, fibronectin, modified fibronectin, collagen, modified collagen, laminin, modified laminin, or a co-polymer in any combination. In some embodiments, the solidified polymer network does not include a silicone polymer. In some embodiments, the solidified polymer network may not include a polylactic acid (PLA) or a modified polylactic acid polymer. In other embodiments, the solidified polymer network may not include a polyglycolic acid (PGA) or a modified polyglycolic polymer. In some embodiments, the solidified polymer network may not include a polyacrylamide or a modified polyacrylamide polymer. In yet other embodiments, the solidified polymer network may not include a polyvinyl alcohol (PVA) or a modified polyvinyl alcohol polymer. In some embodiments, the solidified polymer network may not include a polyacrylic (PAA) or modified PAA polymer. In some other embodiments, the solidified polymer network may not include a polycaprolactone (PCL) or a modified polycaprolactone polymer. In other embodiments, the solidified polymer network may not be formed from a fibronectin or a modified fibronectin polymer. In some other embodiments, the solidified polymer network may not be formed from a collagen or a modified collagen polymer. In some other embodiments, the solidified polymer network may not be formed from a laminin or a modified laminin polymer. In some embodiments, the solidified polymer network may include only one kind of polymer. In various embodiments, the solidified polymer network including only one kind of polymer includes modified polyethylene glycol polymer.

Physical and chemical characteristics determining suitability of a polymer for use in the solidified polymer network may include molecular weight, hydrophobicity, solubility, rate of diffusion, viscosity (e.g., of the medium), excitation and/or emission range (e.g., of fluorescent reagents immobilized therein), known background fluorescence, characteristics influencing polymerization, and pore size of a solidified polymer network. The solidified polymer network is formed upon polymerization or thermal gelling of a flowable polymer (e.g., a pre-polymer solution,)

One type of polymer, amongst the many polymers that may be used, is polyethylene glycol diacrylate (PEGDA), which is a member of the group of modified polyethylene glycol polymers. The mechanism of light initiated polymerization is shown in Equation 1. The free radical initiator Igracure® 2959 (BASF), a highly efficient, non-yellowing radical, alpha hydroxy ketone photoinitiator, is typically used for initiation at wavelengths in the UV region (e.g., 365 nm), but other initiators may be used. An example of another useful photoinitiator class for polymerization reactions is the group of lithium acyl phosphinate salts, of which lithium phenyl 2, 4, 6,-trimethylbenzolylphosphinate has particular utility due to its more efficient absorption at longer wavelengths (e.g., 405 nm) than that of the alpha hydroxy ketone class.

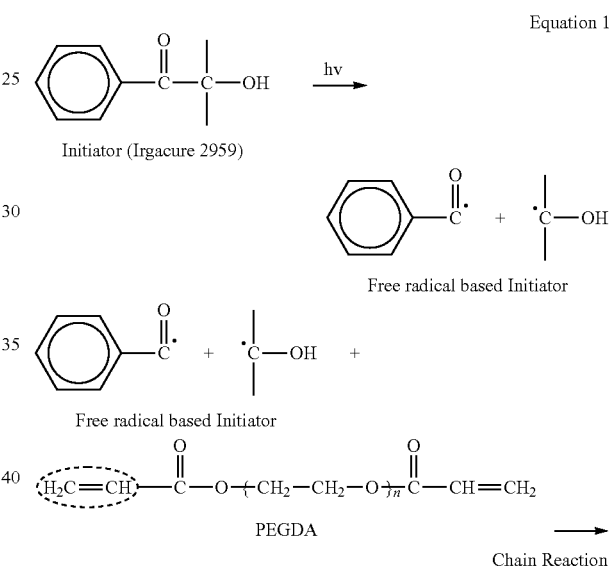

Equation 1

Other types of PEG that may be photopolymerized include PEG dimethylacrylate, and/or multiarm PEG (n-PEG) acrylate (n-PEG-Acr). Other polymer classes that may be used include poly vinyl alcohol (PVA), polylactic acid (PLA) polyacrylic acid (PAA), polyacrylamide (PAM), polyglycolic acid (PGA) or polycaprolactone (PCL).

The molecular weight range of the polymer may be varied as required for the performance of the disclosed in situ-generated capture structures. A wide range of molecular weights of the flowable polymer may be suitable, depending upon the structure of the polymer. A useful star type polymer may have Mw (weight average molecular weight) in a range from about 500 Da to about 20 kDa (e.g., four arm polymer), or up to about 5 kDa for each arm or for a linear polymer, or any value therebetween.

Various co-polymer classes may be used, including but not limited to: any of the above listed polymer, or biological polymers such as fibronectin, collagen or laminin. Polysaccharides such as dextran or modified collagens may be used. Biological polymers having photoactivatable functionalities for polymerization may also be used.

Crosslinking may be performed by radiation of linear or branched PEG polymers, free radical polymerization of PRG acrylates, and specifically tailored chemical reactions such as Michael addition, condensation, Click chemistry, native chemical ligation and/or enzymatic reactions.

The polymers may be selected to have a desired range of crosslinking based on the nature of the polymer (configuration of the flowable polymers such as star, multiarm or comb polymers, length of polymer segments between cross-linkable functionalities) and polymerization conditions (extent of temperature or photoinitiation, amount of photoactivatable initiator present, amount of radical terminator species present, and the like).

In some embodiments, the polymer of the solidified polymer network may be a modified PEG polymer. The polymer may be a star, 4-arm or 2-arm PEG diacrylate polymer.

Swellable Polymers.

PEG polymers may be swellable under various conditions and may be reversed by reverting back to the original media/temperature. Poly-N-isopropylacrylamide (PNIPAm) may be swelled by increasing temperature, and de-swelled by cooling.

Size Modification Motifs.

Some hydrogels, including poly-N-isopropylacrylamide (PNIPAm) or poly acrylamide (PAM), may also incorporate specific moieties such as azobenzene which changes cis/trans orientation upon exposure to light at the surface of the functionalized polymer. This shift can provide significant change in size of the portion of polymer such as an in situ-generated capture structure within a pen. These polymers may alternatively include cinnamic acid functionalities that cross link upon exposure to UV light, which is reversible upon removal of the light. The cross-linked polymer is elongated compared to the non-crosslinked state. Another moiety which may be introduced to these polymers includes triphenyl leucomethane, which forms ion pairs upon application of light, reversibly, upon exposure to light. The wavelength of activating light can be brought into the visible range if trisodium copper chlorophyllin is incorporated into the polymer.

Other Modifications for Functionalization.

A polymer (e.g., PEG) may be modified by incorporating functional groups at one or both of the termini of the (PEG) polymer, which may include thiol, maleimide, carboxyl, amine, methoxy, azide, vinyl sulfone, acetylenic, or acrylate functionalities. The functional groups introduced may be the same or different. Desired peptide motifs, antibodies, or other defined molecular functionalization by appropriate chemical elaboration may be introduced so that the moiety is capably of reacting specifically with a corresponding functionality on the polymer. Biotinylation may be introduced for later reaction with another species linked to streptavidin, or vice versa.

The polymer may include various motifs, including cleavage motifs, reactive terminal motifs, or cell recognition motifs. A cleavage motif may include a peptide sequence inserted into the polymer that is a substrate for one or more proteases, including but not limited to a matrix metalloproteinase, a collagenase, or a cysteine protease such as a caspase or cathepsin. Another category of cleavage motif may include a photocleavable motif such as a nitrobenzyl photocleavable linker which may be inserted into selected locations of the prepolymer. A cleavage motif may be utilized either to remove the solidified polymer network of an in situ-generated capture structure or may be used, as described, as the assay analyte itself when incorporated within an in situ-generated capture structure. The polymer may be modified to incorporate chemically reactive motifs such as, but not limited to, N-hydroxysuccinimidyl (NHS), biotin, alkynyl, or azido moieties, which may be used to introduce assay reagents or assay analytes to the solidified polymer network of the in situ-generated capture structure as described above. In other embodiments, the polymer may include cell recognition motifs including but not limited to a RGD peptide motif, which is recognized by integrins, or a furin substrate as described above, which may be used as assay analyte or assay reagents.

Reversing/Removing/Minimizing the In Situ-Generated Capture Structure.

A number of mechanisms may be used to remove or reduce the in situ-generated capture structure when there is no further purpose for it. For example, once an assay is completed and desirable biological cells have been identified, it may be useful to remove the in situ-generated capture structure in order to continue culturing and expanding the biological cell demonstrating desirable activities or properties.

Mechanical force. Increasing flow can be used if at least a portion of the in situ-generated capture structure is located within a flow region as opposed to an isolation region of a pen. For example, when the in situ-generated capture structure is located within a flow region of the enclosure, a rate of fluidic flow may be increased through the flow region which may detach the at least one capture structure from surfaces to which it is attached, including but not limited to the substrate, the walls of the flow region (which may be formed from microfluidic circuit material), or a cover. In some embodiments, the at least one in situ-generated capture structure may be located within an isolation region of a sequestration pen, and after the assay is complete, the sequestration pen or the isolation region therein may be modified to bring flow through the isolation region, similarly detaching the in situ-generated capture structure from surfaces it is attached.

Hydrolytic susceptibility: Porogens, which may include polymers incapable of being chemically linked to the photoinitiated polymer(s), may be included when forming the in situ-generated capture structure. The degree/size of openings within the formed hydrogel can customize the hydrolysis rate via accessibility within the in situ-generated capture structure). In other embodiments, the pores formed may be employed to permit secreted materials or chemical reagents to pass through the in situ-generated capture structure but prevent a cell from moving through the in situ-generated capture structure. In other embodiments, degradability of these polymers may be increased by introducing degradable segments such as polyester, acetal, fumarate, poly(propylene fumarate) or polyhydroxyacids into polymers (e.g., PEG polymers).

Reducing agents: PEG may be formed with disulfide linkages at intervals along the macromere, which may be random or predetermined. The disulfide bonds may be broken by Dithiothreitol (DTT), mercaptoethanol, or TCEP.

Thermal: poly N-isopropylacrylamide (PNIPAm) or other suitable LCST polymers may be used to introduce capture structures upon heating. They may be removed by decreasing the temperature of the formed polymer capture structure. The polymers may include ELPs or other motifs that also permit removal by other mechanisms such as hydrolysis or proteolysis. In particular, PNIPAm may be used to create a surface for adherent cells, but then switched to permit export. Other polymers may also demonstrate size change depending on temperature. For example, PEGDA hydrogel incorporated within an in situ-generated capture structure may swell by about 20% upon cooling from a temperature of about 40° C. to about 20° C. The size of a PEGDA hydrogel in situ-generated capture structure may be increased locally by using laser illumination directed at the substrate underlying the in situ-generated capture structure or at a transparent cover over the in situ-generated capture structure, which may be, for instance ITO.

Proteolytic susceptibility: Hydrogels may have any sort of peptide sequence engineered in, such that selective proteolysis upon a selected motif by a selected protease can remove/reverse/or minimize a hydrogel capture structure. Some classes of modified PEG include PEG having elastin like peptide (ELP) motifs and/or having peptide motifs for susceptibility to a variety of proteases (enzyme sensitive peptide ESP). A large number of these motifs are known. One useful motif is RGD which may be constrained to be cyclic.

Osmotic susceptibility: Calcium concentration/other osmotic strategies can be employed to degrade and remove an in situ-generated capture structure. As above, dimensionally swell or de-swell capture structures using media changes.

Light initiated photocleavage: As described above, a photocleavable motif such as a nitrobenzyl photocleavable linker may be incorporated within the solidified polymer network of an in situ-generated capture structure. An in situ-generated capture structure including a photocleavable motif may be susceptible to removal or reduction in size by exposure to light including at least some light having a suitable wavelength to initiate cleavage of the photocleavable motif.

In some applications, the in situ-generated capture structure may not be removed but may simply be swelled or de-swelled using light or media\solvent changes. Some types of hydrogels may incorporate moieties that respond reversibly to light (for example, change regiochemistry about a rigid bond; form reversible crosslinks within the polymer, or form/break ion pairs).

Microfluidic Device Assisted Heating.

The microfluidic device may further include a metal pad disposed on the substrate at a location of the in situ-generated capture structure. The metal pad may be created by deposing a contiguous metal shape or a pattern of metal shapes onto the substrate. The thermal pad can comprise any type of metal that can be excited by a light source to produce heat. Suitable metals include chromium, gold, silver, aluminum, indium tin oxide, or any combination thereof. Metals may be combined in a multi-layered thermal pad, e.g., a layer of chromium, a layer of titanium, a layer of gold. Other metals (and alloys) are known in the art. The thermal pad can comprise a continuous metal surface or can comprise a pattern of metal (e.g. metal shapes such as dots, squares, lines, cones, irregular forms). In some embodiments, a gold pad may be disposed on the substrate at a location where an in situ-generated capture structure will be/has been generated. The thermal pad may be used to generate heat to gel, swell, reduce, or remove an in situ-generated capture structure. Heat may be generated by directing light into the microfluidic device at the location where such gelling, swelling, reduction or removal is desired. In some embodiments, the solidified polymer network may include a thermosensitive polymer. When a solidified polymer network of an in situ-generated capture structure includes a thermosensitive polymer, the device may further include a thermal pad disposed on the substrate at a location beneath the at least one in situ-generated capture structure will be introduced.

Methods of Assaying a Micro-Object Using Functionalized Capture Structures.

A method is provided for assaying a micro-object (e.g., a biological cell or an embryo) or a biological product produced by the micro-object, in a microfluidic device having at least a first in situ-generated capture structure including steps of: disposing a micro-object within the microfluidic device in a region proximal to the first in situ-generated capture structure, where the in situ-generated capture structure includes a solidified polymer network, and further where the solidified polymer network includes an assay reagent or an assay analyte; contacting the assay reagent or assay analyte with the micro-object or a biological product of the micro-object; and detecting an interaction of the assay reagent or assay analyte with the micro-object or the biological product. In various embodiments, a method is provided for assaying a micro-object (e.g., a biological cell) in a microfluidic device having at least a first in situ-generated capture structure including steps of: disposing a micro-object within a microfluidic device in a region proximal to the first in situ-generated capture structure, where the in situ-generated capture structure includes a solidified polymer network, and further where the solidified polymer network includes an assay analyte; contacting the assay analyte with a biological product of the micro-object; and detecting an interaction of the assay analyte with the biological product.

In yet other embodiments, another method is provided for assaying a micro-object (e.g., a biological cell) in a microfluidic device having at least a first in situ-generated capture structure including steps of: disposing a micro-object within a microfluidic device in a region proximal to the first in situ-generated capture structure, where the in situ-generated capture structure includes a solidified polymer network, and further where the solidified polymer network includes an assay analyte; contacting the assay analyte with the micro-object; and detecting an interaction of the assay analyte with the micro-object. In yet other embodiments, a method is provided for assaying a micro-object (e.g., a biological cell) in a microfluidic device having at least a first in situ-generated capture structure including steps of: disposing a micro-object within a microfluidic device in a region proximal to the first in situ-generated capture structure, where the in situ-generated capture structure includes a solidified polymer network, and further where the solidified polymer network includes an assay reagent; contacting the assay reagent with the micro-object or a biological product of the micro-object; and detecting an interaction of the assay reagent with the micro-object or the biological product.

The assay reagent or assay analyte of any of the above methods may include any assay reagent or assay analyte described herein.

In various embodiments of any of the methods of assaying a micro-object, the assay reagent or assay analyte that is included within and/or on the in situ-generated capture structure may be covalently or non-covalently attached to the solidified polymer network of the in situ-generated capture structure, in any way described above. The assay reagent or assay analyte may include a protein, an oligonucleotide, an organic molecule, or a saccharide. The assay reagent or assay analyte may be, respectively, any assay reagent or assay analyte as described above.

In various embodiments of any of the methods of assaying a micro-object, the biological product of a micro-object may include a protein, an oligonucleotide, an organic molecule, or a saccharide. The biological product of the micro-object may be any biological product as described herein, and may function in the methods as the analyte measured by an assay reagent included within and/or on the in situ-generated capture structure. Alternatively, the biological product of the micro-object may bind to, react with, and/or cleave an assay analyte included within and/or on the in situ-generated capture object, whereby the biological product acts as a reagent in the assay method.

In various embodiments of any of the methods of assaying a micro-object (e.g., a biological cell or embryo), the microfluidic device may include an enclosure comprising: a substrate, microfluidic circuit materials and a flow region located within the enclosure, where the at least one in situ-generated capture structure is disposed within the enclosure. In some embodiments, the enclosure of the microfluidic device further includes at least one sequestration pen, where the at least one in situ-generated capture structure may be disposed within the at least one sequestration pen. The sequestration pen may include an isolation region and a connection region, where the connection region may have a proximal opening to the flow region and a distal opening to the isolation region. In some embodiments, the in situ-generated capture structure may be disposed within the isolation region of the sequestration pen. The flow region may include a channel. The at least one capture structure may be disposed at a first location adjacent to a first wall of the sequestration pen.

In various embodiments of any of the methods of assaying a micro-object, the enclosure may include a plurality of sequestration pens. The plurality of sequestration pens may be aligned in a row, and the proximal opening of each of the plurality of sequestration pens may open in a common direction within the flow region. In some embodiments, the flow region may include a channel and the proximal opening of each of the plurality of sequestration pens may open off one side of the microfluidic channel.

In various embodiments of any of the methods of assaying a micro-object, the substrate of the microfluidic device may be configured to generate a dielectrophoretic (DEP) force upon a micro-object in a fluidic medium within the enclosure. The step of disposing the micro-object(s), (e.g., biological cell(s)), within the microfluidic device to the region proximal to the at least first in situ-generated capture structure may include moving the micro-object(s) using dielectrophoretic force. The dielectrophoretic force may be optically actuated. Alternatively, the substrate of the microfluidic device may be configured to generate an electro-wetting force on a droplet within the enclosure. The step of disposing the micro-object(s) within the microfluidic device to the region proximal to the at least first in situ-generated capture structure may include moving the micro-object(s) using electrowetting force. The electrowetting force may be optically actuated. In some embodiments, the microfluidic device may include one or more substrates which may be configured to generate both dielectrophoretic forces and electrowetting forces within the enclosure of the microfluidic device, each of which may be light actuated. Alternatively, fluidic flow within the flow region (e.g., microfluidic channel) and/or gravity may be used to dispose the micro-object(s) within the microfluidic device. In some embodiments, a combination of dielectrophoretic forces, electrowetting forces, gravity and/or fluidic flow may be used to dispose the micro-object(s). In various embodiments, the microfluidic device may have at least one surface that includes a coating material. In some embodiments, the coating material may covalently modify the at least one surface to provide a conditioned surface which enhances cell growth, viability, portability and any combination thereof.

The conditioned surface may be selected to be any suitable conditioned surface described herein.

In various embodiments of any of the methods of assaying a micro-object, the assay reagent or assay analyte included within and/or on the in situ-generated capture structure is allowed to interact with the micro-object (e.g., biological cell or embryo) or biological product of the micro-object. In some embodiments, the interaction may be non-covalent, e.g., binding of a protein such as an antigen or a cytokine (e.g., an analyte), which is a biological product of the micro-object, with an antibody (e.g., an assay reagent) included within and/or on the in situ-generated capture structure. In another example of a noncovalent interaction, the in situ-generated capture structure may include a binding recognition motif for a protein expressed on the surface of a micro-object, where if the micro-object expresses the protein of interest, it may be bound to the in situ-generated capture structure. In other embodiments, chemical bonds may be cleaved by the interaction, for example when the in situ-generated capture structure includes a protease recognition motif, thereby providing an assay analyte bound to the in situ-generated capture structure. In this embodiment, the interaction may be the interaction of a protease either secreted by a micro-object or expressed on the surface of the micro-object, which interacts with the recognition motif to cleave the substrate incorporated within the in situ-generated capture structure. In yet other embodiments, the interaction may include a covalent interaction. For example, the in situ-generated capture structure may include an assay reagent such as an antibody configured to bind specifically with a biological product (e.g., antigen, cytokine, or any secreted biological product), where the in situ-generated capture structure or the antibody also includes a reactive moiety such as a crosslinking moiety (e.g., carboxylic acid, amino moiety, thiol moiety, or activated species thereof) which covalently binds the biological product that non-covalently binds to the antibody assay reagent.

In various embodiments of any of the methods of assaying a micro-object, the step of detecting comprises detecting a signal from the at least one capture structure. In various embodiments of the method, the detectable signal may be incorporated within an assay reagent or assay analyte included within and/or on the in situ-generated capture structure. The detectable signal may be concentrated to a surface of the at least one capture structure or may be detected in a region immediately adjacent to the in situ-generated capture structure within the enclosure or alternatively, within the sequestration pen. In yet other embodiments, the detectable signal may be concentrated to an interior portion of the in situ-generated capture structure, which may occur via diffusion throughout the solidified polymer network. The detectable signal may be fluorescent, luminescent or colorimetric. In some embodiments, the signal may be fluorescent. In some embodiments, the step of detecting the fluorescent signal may further include quantifying the fluorescent signal.

In some embodiments of any of the methods of assaying a micro-object, the step of detecting a signal from the at least one capture structure may include detecting loss of an initial fluorescent signal of the at least one capture structure. For example, an in situ-generated capture structure may include a solidified polymer network that comprises a protease substrate motif as an assay analyte, where the substrate motif includes a detectable signal such as a fluorescent label. Detecting the interaction between the assay analyte and a protease capable of cleaving it may include detecting the extent of loss of fluorescent signal from the in situ-generated capture structure incorporating the fluorescent protease substrate motif. In another embodiment, the method may include detecting a gain of fluorescent signal, when the in situ-generated capture structure incorporating a protease substrate motif as an assay analyte includes a quenched fluorescent pair (e.g., a FRET pair, which may have dual labels on suitably spaced different amino acids in the inserted substrate motif, or may include a molecular beacon or other FRET probe construct). In this embodiment, the interaction between the protease substrate motif of the in situ-generated capture structure and a protease produced by a micro-object (e.g., the biological product) may permit detection of an increase of signal when cleavage of the substrate by the protease increases the spatial separation between the quenched fluorescent pair. One or more fluorescent signals may be detected.

In other embodiments of any of the methods of assaying a micro-object, the fluorescent signal may be incorporated within the biological product or micro-object that interacts with the assay reagent or assay analyte included within and/or on the in situ-generated capture structure. For example, a protein of interest secreted by a micro-object (e.g., biological product) may also include a signal such as green fluorescent protein (GFP), and thus may be directly detectable when interacting with an antibody included within and/or on the in situ-generated capture structure that binds specifically to the protein of interest. In other embodiments, a micro-object expressing a protein of interest on its surface may also have a detectable signal that is contained within the micro-object (such as mCherry, an inserted protein having a sequence related to Discoma sp.), whereupon binding with the antibody included within and/or on the in situ-generated capture structure (e.g., assay reagent), fluorescence of the intracellular protein may be directly detected.

In yet other embodiments of any of the methods of assaying a micro-object, the step of detecting further includes introducing a detection reagent having a detectable label to the region proximal to the in situ-generated capture structure. Any suitable detection reagent described herein may be used. Introduction of the detection reagent may include flowing a solution containing the detection reagent through the flow region of the microfluidic device. In some embodiments, when the at least one in situ-generated capture structure is located within a sequestration pen, the detection reagent may enter the sequestration pen containing the in situ-generated capture structure substantially or only by diffusion, after being flowed into the enclosure of the microfluidic device. The introduction of the detection reagent may be performed after the step of disposing the micro-object into the enclosure or alternatively, into the sequestration pen, has been performed. In some embodiments, the detection reagent may be introduced before the micro-object has been introduced to the enclosure or the sequestration pen. In some embodiments, the step of introducing the detection reagent may be performed just prior to performing the step of detecting. In various embodiments, the detection reagent is configured to be concentrated to the in situ-generated capture structure when an assay reagent included within and/or on the in situ-generated capture structure interacts with the biological product or the micro-object itself (e.g., the analyte of the assay). The detection reagent may be concentrated to the in situ-generated capture structure (e.g., constrained to the immediate region of the in situ-generated capture structure) by any suitable mechanism such as forming a binding pair, hybridizing with a target oligonucleotide, intercalating or covalently reacting with the biological product or micro-object, which is itself constrained to the immediate region of the in situ generated capture structure by virtue of the interaction between the assay reagent or assay analyte/micro-object or biological product thereof. In some embodiments, the interaction between the detection reagent/micro-object or biological product thereof/assay reagent or assay analyte/solidified polymer network of the in situ-generated capture structure may form a complex, which may act to concentrate the detectable signal of the detection reagent. In some embodiments, the detectable label of the detection reagent may not be detectable until it is concentrated to the in situ-generated capture structure. For example, if the detection reagent is an intercalator dye or molecular beacon (Fret quenched hairpin probe), Scorpions (Fret quenched probe/primer combination) or any other FRET label of an oligonucleotide, detecting the signal may not be performed until after the detection reagent binds to the biological product of the micro-object or the micro-object itself, which in some embodiments, may be immobilized to the in situ-generated capture structure. In various embodiments, the detectable label of the detection reagent is non-covalently attached to the assay reagent or assay analyte.

In some embodiments of any of the methods of assaying a micro-object, the detection reagent comprises at least a first antibody. One or more antibodies may be used to detect the interaction between the assay reagent or assay analyte included within and/or on the in situ-generated capture structure and the biological product of the micro-object or the micro-object itself. In some embodiments, the method may include introducing a first detection antibody having specificity for the assay analyte/(biological product or micro-object) pair or the assay reagent/(biological product or micro-object) pair, followed by introducing a second antibody that is labeled and can bind to at least one portion of the assay analyte/(biological product or micro-object) pair or the assay reagent/(biological product or micro-object) pair. In some embodiments, the method may include introducing a second antibody having specificity for the first detection antibody. In other embodiments, the labeled second antibody may have specificity for a complex of the assay analyte/(biological product or micro-object) pair or a complex of the assay reagent/(biological product or micro-object) pair.

In various embodiments of any of the methods of assaying a micro-object, the method may further include a step of exporting the micro-object from the microfluidic device. The micro-object may be exported based on the results of the assay (e.g., demonstrating a desirable level of signal in the detection step). In various embodiments of the method, exporting the micro-object from the microfluidic device may further include moving the micro-object to another portion of the substrate of the microfluidic device. For example, the steps of assaying may be performed within a selection sector as described herein, and micro-objects demonstrating selected characteristics as identified by the method of assaying, may be moved by DEP forces, electro-wetting forces, gravity or fluidic flow to an isolation sector of the microfluidic device for further processing.

In various embodiments of any of the methods of assaying a micro-object, the method may further include a step of reducing or removing the in situ-generated capture structure by introducing a hydrolytic agent, introducing a proteolytic agent, introducing a fluidic medium that increases or decreases osmolality of the fluidic medium within the flow region and/or the sequestration pen, changing temperature of the in situ-generated capture structure, or optically illuminating the in situ-generated capture structure, thereby reducing or removing the at least one capture structure. The step of changing the temperature may further include optically illuminating a thermal pad on the substrate adjacent to or under the in situ-generated capture structure. In some embodiments, reducing (e.g., reducing the size or number of functionalized sites of the in-situ generated capture structure) or removing the in situ-generated capture structure may release a micro-object from its concentration/constraint to the in situ-generated capture structure.

In other embodiments, the step of exporting a micro-object may include introducing a competing binding partner for the assay reagent/assay analyte to which the micro-object has bound, as described above. The competing binding partner for the assay reagent/assay analyte may cause the micro-object to be released from its binding interaction with the array reagent/assay analyte and permit export of the micro-object.

FIGS. 5A-E shows one embodiment of the method of assaying a micro-object (e.g., a biological cell or an embryo) in a microfluidic device having at least a first in situ-generated capture structure within an enclosure. In this embodiment, the enclosure includes a sequestration pen including the at least a first capture structure disposed therein, where the in situ-generated capture structure acts as a pre-selected assay region. The in situ-generated capture structures may be functionalized with, for example an assay reagent, as shown in FIG. 5A. The method is not so limited, and the in situ-generated capture structure may be functionalized to contain an assay analyte instead.

In FIG. 5A, an in situ-generated capture structure 502 is shown, which has, for example, streptavidin introduced into the solidified polymer network. Prepolymer solutions of the structural polymer (e.g., a streptavidin modified reactive prepolymer) and soluble initiator may be flowed into the microfluidic device. Precise and selective solidification of the in situ-generated capture structure can be accomplished by illumination in one corner of the sequestration pen 530, similarly to the schematized process shown in FIG. 4C for the transformation of prepolymer 405 to in situ-generated capture structure 404. In this embodiment, the in situ-generated capture structure 502 is generated to be located near/at a wall formed of microfluidic circuit material 260 at a corner of the isolation region distal to the opening of the sequestration pen 530 into the microfluidic channel 264, where fluidic medium flows (278). After formation of the in situ-generated capture structure, excess polymer solution and initiator may be removed from the system by flushing the microfluidic channel 264, and permitting the unused reagents to diffuse out of the sequestration pen 530. The in situ-generated capture structure 502 may present streptavidin both on the surface of the in situ-generated capture structure, and throughout the solidified polymer network.

A functionalized antibody may be introduced to the isolation region of the sequestration pen 530. The functionalized antibody may have a biotin functionality, which may bind to the streptavidin sites on the surface of or within the in situ-generated capture structure 502, thereby providing antibody 504 included at the surface or within the in situ-generated capture structure 502, providing an in situ-generated capture structure (502 plus 504) equivalent to capture structure 406 of FIG. 4B (which is also equivalent to schematic in situ-generated capture structure 406B of FIG. 4C). The antibody 504 may be any antibody that is specific for a secreted biological product. In some embodiments, the antibody 504 may be a cytokine, such as IL-2, IFN alpha/beta, TNF alpha, and the like. The antibody 504 may be used to detect cells that secrete the cytokine of interest. All of the biotinylated antibody 504 does not need to be included within and/or on the at least one in situ-generated capture structure. Some portion of the biotinylated antibody 504 may also be free-floating in the solution. The reverse pairing may also be used, e.g., the in situ-generated capture structure 502 may have biotinylated sites incorporated by the photoinitiated solidification of the polymer network, and the antibody 504 may be modified to include streptavidin. The streptavidin functionality can bind to the biotin sites on the in situ-generated capture structure 502, thereby also providing antibody 504 included at the surface or within the in situ-generated capture structure 502.

While in FIGS. 5A-5E, the assay reagent is shown as an antibody for convenience and simplicity, the method is not so limited. The assay reagent may be any suitable assay reagent as described herein.

Biological cells 506 can be flowed into the microfluidic channel 264, and disposed by any suitable method described herein into isolation regions of the sequestration pen 530. Cell(s) 506 of interest may be introduced into the pen having a streptavidin functionalized capture structure, before or after the streptavidin functionalized antibody is introduced. There may be one or more cells 506 of interest. In some embodiments, there may be a single cell 506.

The cell(s) can be cultured, and may secrete a biological product. The biological product may be a protein. One non-limiting example of a proteinaceous biological product of a cell may be a cytokine. One non-limiting example of a cell that may produce a cytokine may be a T-cell.

Figure 5B:
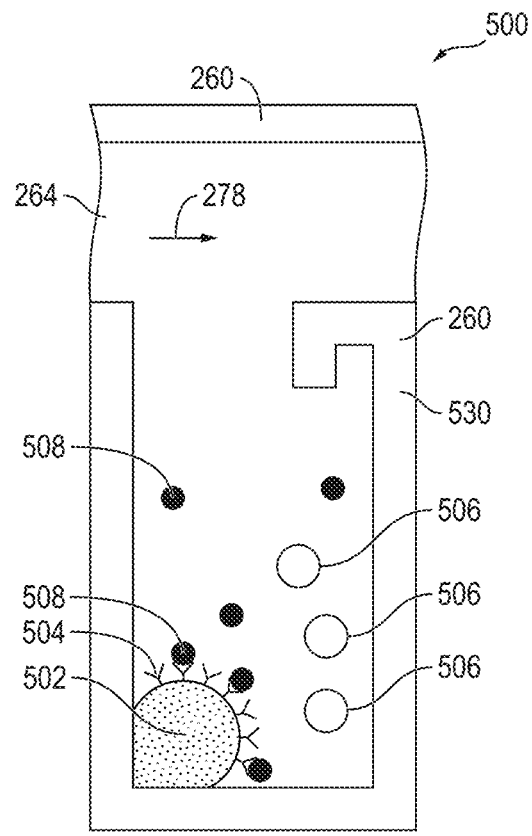
Figure 5C:
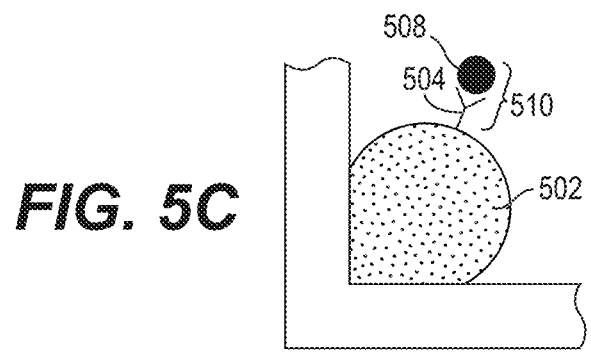

As shown in FIG. 5B, as cell culturing continues, the cell 506 may produce the biological product 508 that can bind to the antibody assay reagent 504. The biological product 508 will be captured by its interaction with the assay reagent 504 on the in situ-generated capture structure 502, e.g., captured by antibodies incorporated within or on the surface of the in-situ generated capture structure. FIG. 5C shows an expanded view of the in situ-generated capture structure 502 of FIG. 5B, showing the complex 510 that is formed by interaction (e.g., binding) of the biological product 508 with the assay reagent 504 (e.g., antibody) of the in situ-generated capture structure 502. The in situ-generated capture structure 502 can be located either near the proximal opening to the microfluidic channel within the pen or can be located within a more distal section of the connection region or within the isolation region of the pen.

Figure 5D:
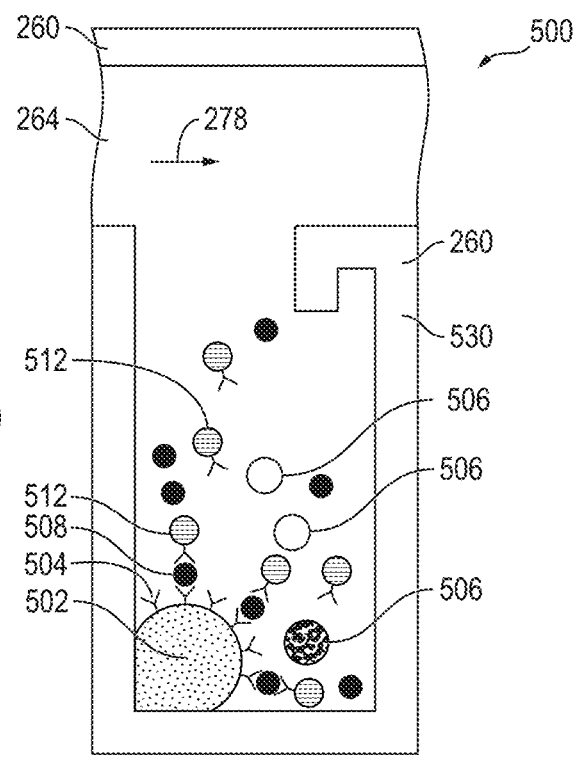
Figure 5E:
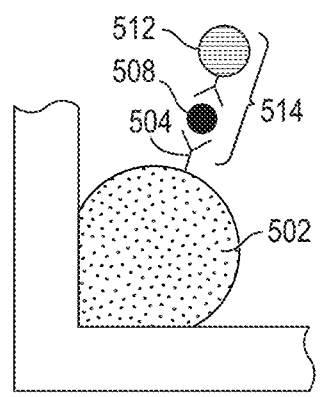

The antibodies, assay reagent 504, included at the surface or within the in situ-generated capture structure 502, capture and concentrate the biological product of interest 508 (e.g., analyte). The concentrated captured biological product 508/antibody 504 of complex 510 may be made detectable by introduction of the labeled antibody 512, which may be fluorescently labeled, as shown in FIG. 5D. Detection of the fluorescent signal of the immobilized antibody/cytokine/antibody complex 514, which is concentrated to the solidified polymer network of the in situ-generated capture structure 502/504 can permit detection and ranking of more/less actively secreting biological cells. FIG. 5E shows an expanded view of the region of the sequestration pen where the in situ-generated capture structure 502 is located. The complex 514 of the immobilized antibody 504/cytokine (e.g., biological product 508)/labeled antibody 512 is shown. While the detection reagent is shown here as an antibody for simplicity, the detection reagent is not so limited but may be any suitable detection reagent as described herein.

In some other embodiments, the biological product 508 may itself contain a detectable label, such as, but not limited to green fluorescent protein. When the biological product 508 includes a detectable label, additional labeling by a detection reagent may not be performed, but the amount of detectable label of the biological product 508 may be directly detected. Thus, in some embodiments of the method, an analyte (e.g., biological product 508) may be a detectable analyte and may interact and be captured by the assay reagent 504 to form a detectable complex 510' (not shown), which may be detected.

Multiplexed Assay Methods.

In various embodiments of methods of assaying one or more micro-objects (e.g., biological cell or embryo), a multiplexed assay may be performed. In one embodiment, the at least one capture structure located within the enclosure, or, optionally, within a sequestration pen, may contain more than one assay reagent or assay analyte. In other embodiments, the enclosure, or optionally, a sequestration pen therein, may include a first capture and a second capture structure. The first capture structure may be as described above and include a first assay reagent or first assay analyte. The second capture structure may include a second solidified polymer network, and the second solidified polymer network may include a second assay reagent or a second assay analyte. The second solidified polymer network and the second assay reagent or second assay analyte may include any feature as described above in any combination. In some embodiments, each of the first and second capture structures includes a different assay reagent or assay analyte. In some embodiments, the first and the second capture structures may include a first assay reagent and a second assay reagent that differ from each other. In other embodiments, the first and the second capture structure may contain a first assay analyte and a second assay analyte that differ from each other. In yet other embodiments, the first capture structure and the second capture structure may include an assay reagent on one capture structure and an assay analyte on the second capture structure. In some embodiments of the multiplexed assay, the first capture structure and the second capture structures may be disposed within the enclosure or, alternatively, the sequestration pen, at distinguishable locations. The distinguishable locations of the first and the second capture structure may be adjacent to the same wall of the enclosure or to the same wall of a sequestration pen therein, or adjacent to different walls of the enclosure or to different walls of a sequestration pen therein.

In various embodiments of the multiplexed assay, the step of detecting includes detecting a first analyte and a second analyte, wherein the first analyte is different from the second analyte. The first analyte and the second analyte may be a first biological product and a second biological product secreted by a micro-object. In other embodiments, the first analyte and the second analyte may be a biological product secreted from a micro-object and the second analyte may be a biological product present on the surface of the micro-object, and may be different from each other. In other embodiments, the step of detecting may include detecting a first biological product that interacts with a first assay analyte on the first capture structure and detecting a second biological product that interacts with a second assay analyte on the second capture structure. In yet other embodiments, the step of detecting may include detecting a first biological product that interacts with a first assay reagent and detecting a second biological product that interacts with a second assay reagent.

The step of detecting the interactions may further include introducing a first detection reagent and a second detection reagent to the region proximal to the first and second capture structures, wherein each of the first and second detection reagents includes a detectable label. The detectable labels of the first detection reagent and the second detection reagent may each independently be fluorescent, colorimetric, or luminescent. The step of detecting may further include detecting a first fluorescent signal of the first detectable label and a second fluorescent signal of the second detectable label. In some embodiments, the first fluorescent signal and the second fluorescent signal may be physically distinguishable, e.g., located at different positions within the enclosure, or alternatively at different positions within the sequestration pen therein. In other embodiments, the first fluorescent signal and the second fluorescent signal may be spectrally distinguishable. In other embodiments, one of the first or the second detectable signals may be fluorescent and the other of the first or the second detectable signals may be not fluorescent.

In various embodiments of the multiplexed method, each of the first and second detectable reagents may be non-covalently attached to the respective first or second assay reagent or assay analyte. In some embodiments, each of the first and second detection reagents may include an antibody. In some embodiments, each of the first and second detection reagents include a respective third and fourth antibody, each of which may have a detectable label, where the third antibody binds specifically to the first assay reagent or first assay analyte/(biological product or micro-object) pair and the fourth antibody binds specifically to the second assay reagent or assay analyte/(biological product or micro-object pair). In some embodiments, the third antibody may be a secondary antibody to the first assay reagent when the first assay reagent is an antibody. In some embodiments, the fourth antibody may be a secondary antibody to the second assay regent, when the second assay reagent is an antibody.

In various embodiments of the multiplexed assay, the first and/or the second fluorescent signals may be quantified.

In various embodiments of the method, a multiplex assay may be performed on three or more characteristics of the biological product or three or more different biological products of a micro-object or the micro-object itself, or any combination thereof. There may be a third or more capture structure in the enclosure or alternatively within the at least one sequestration pen therein. Each of the third or more capture structure may include a solidified polymer network, and the solidified polymer network of each of the third or more solidified polymer network may include an assay reagent or an assay analyte. The assay reagent or assay analyte of each of the third or more capture structure may be different from the first assay reagent or assay analyte of the first capture structure, and/or may be different from the second assay reagent or assay analyte of the second capture structure. Each of the assay reagent or assay analyte of the third or more capture structures may be different from each other. In other embodiments, one or both of the first and second capture structures may alternatively include more than one assay reagent or assay analyte, distinguishable from the first assay reagent or assay analyte of the first capture structure and distinguishable from the second assay regent or assay analyte of the second capture structure.

In various embodiments of a multiplexed method of assaying one or more micro-objects, the step of detecting further comprises detecting a first, a second, a third or more detectable signals that are distinct in location within the at least sequestration pen, detectably spectrally distinct, or a combination thereof.

The multiplexed method may include any of the steps described above for the singleplex method, including but not limited to disposing the one or more micro-objects within the microfluidic device where the microfluidic device includes at least one capture structure configured to assay for more than one characteristic within the enclosure or within a sequestration pen therein, or alternatively includes more than one capture structure within the enclosure or more than one capture structure within at least one sequestration pen, where each of the more than one capture structure is configured to assay for one characteristic; allowing a micro-object to release or produce one or more biological products (any combination of which may be used in any combination with an assay reagent or assay analyte of any of the multiplexed assay reagents and/or assay analytes as described above); allowing assay analyte(s) or assay reagent (s) to interact with the biological product(s) or the micro-object itself; and any aspect of detecting the interaction.

FIG. 7 illustrates a multiplexed assay according to the methods described herein, and displays a flow region (microfluidic channel 264) within the enclosure (not shown), and microfluidic circuit material 260, which forms walls defining the channel 264. One sequestration pen 730 within microfluidic device 700 is shown, and has walls enclosing the sequestration pen made of microfluidic circuit material 260. as described above. Sequestration pen 730 has three capture structures 702, 704, 708 disposed in three physically distinguishable locations within the pen 730. There are two micro-objects 706 loaded into the pen 730, which, in this embodiment, are producing biological products 716, 718, and 720. The biological products 716, 718, 720 may be all different or may be the same biological product which is assayed for three different characteristics by the assay reagents 710, 712, 714 which are included respectively within and/or on capture structures 702, 704, 708. The assay reagents 710, 712, 714 are each different from each other and test for either a different biological product or a different characteristic of a biological product. As shown in FIG. 7, the assay reagents 710, 712, 714 are shown as antibodies for ease of viewing, but the method is not limited to antibody assay reagents, but may be any suitable combination of assay reagents and/or assay analytes as described herein. The timepoint illustrated in FIG. 7 is the point in time after the micro-objects 706 have been allowed to produce biological product(s) 716, 718, 720; biological product(s) 716, 718, 720, have already interacted with the assay reagents 710, 712, 714, each of which is immobilized to respective capture structures 702, 704, 708; and after the time point where the detection reagents 722, 724, 726 have already been introduced to the sequestration pen 730 and have bound specifically to their targets 716, 718, 720. For ease of viewing, detection reagents 722, 724, 726 are represented as antibodies, but the method is not limited to antibody detection reagents as discussed above. Also, for ease of viewing detection reagents 722, 724, 726 each include a label (not shown), where the label may be a detectable label directly attached to detection reagents 722, 724, 726, or alternatively, the label may be attached to a second antibody (not shown), which binds specifically to the antibodies 722, 724, 726. Each detectable label directly attached to detection reagents 722, 724, 726 may be detectably distinguishable from each of the other detectable labels by being spectrally distinguishable or may be detectably distinguishable by location of the in situ-generated capture structure to which the detectable label of the detection reagent binds. Each of the assay complexes, which may include a combination of capture structure, assay reagent or assay analyte (e.g., depending on the assay being performed), micro-object or biological product (e.g., whether the assay reagent or assay analyte interacts with the micro-object or a biological product of the micro-object), and detection reagent, and shown in FIG. 7 as (702/710/716/722); (704/712/718/724); and/or (708/714/720/726), may be detected independently or may be detected at the same time. The detectable signals from each complex may be quantified, by comparison to an in situ standardized signal, by normalization to each other, and/or any suitable method of quantification.

Methods of Loading.

Loading of biological micro-objects (e.g., biological cells) or micro-objects (including but not limited to beads) into the enclosure or alternatively to the sequestration pen, can involve the use of fluid flow, gravity, a dielectrophoresis (DEP) force, electrowetting, a magnetic force, or any combination thereof as described herein. The DEP force can be generated optically, such as by an optoelectronic tweezers (OET) configuration and/or electrically, such as by activation of electrodes/electrode regions in a temporal/spatial pattern. Similarly, electrowetting force may be provided optically, such as by an opto-electro wetting (OEW) configuration and/or electrically, such as by activation of electrodes/electrode regions in a temporal spatial pattern.

Method of Preparation.

A method is provided for preparing at least one capture structure within a microfluidic device. In situ-generated capture structures, may be introduced either before or after introduction of cells to the microfluidic (or nanofluidic) device. The in situ-generated capture structures may be designed to be temporary or may be kept in place until the conclusion of the experiment/assay/sorting/culturing process.

The in situ-generated capture structures may be introduced by photoactivation, temperature change, or osmotic change which can cause a polymer solution present within the microfluidic to form an in situ-generated capture structure capable of preventing a biological cell or a bead from crossing the in situ-generated capture structure. Depending on the mesh size of the in situ-generated capture structure, different categories of chemical species may be permitted to pass through the in situ-generated capture structure. If the mesh size is chosen to be about 2 nm, only small molecule components may be permitted to pass, but proteins, etc. may sequestered by the in situ-generated capture structure. The in situ-generated capture structure may include a crosslinked polymer having a larger mesh size that may not prevent smaller substances such as proteins, nucleic acids, organelles, or signaling molecules from crossing the in situ-generated capture structure. The in situ-generated capture structure may permit media to pass through while not permitting a cell or a bead to cross the in situ-generated capture structure.

The process of introducing light activated polymerization can be performed within the microfluidic device. Diffusion competes with the polymerization process, so the ability to quickly create free radicals may be useful. Additionally, free radicals can quickly combine with free oxygen. While photopolymerization is very efficient and quick in the absence of oxygen in the media, when biological cells are present (thus requiring the presence of oxygen), adjustments to the number of initiating radicals may be made to compensate. In fact, the limiting effect of oxygen is helpful as chain termination happens more quickly and limits the amount of extraneous polymer formed, particularly when introducing small limited amounts of polymer to form small capture structures that do not entirely block entrance to or egress from a pen or a channel.

In some embodiments, the step of initiating solidification of the flowable polymer may include optically illuminating the at least one selected area of the flow region, and further where the step of solidification of the flowable polymer may include polymerizing polymers of the flowable polymer to form a solidified polymer network. The step of introducing a flowable polymer may further include introducing a photoactivatable polymerization initiator.

In some other embodiments, the step of initiating solidification of the flowable polymer may include changing a temperature at the at least one selected area of the substrate. The step of solidification of the polymer may further include gelling the polymer to form a polymer network. The step of changing the temperature at the selected area of substrate may further include optically illuminating a thermal pad on the substrate.

The in situ-generated capture structure can be formed by copolymerizing two polymers, one having, for example, an RGD peptide motif. In other embodiments, a precursor pre-polymer (like prepolymer 401' of FIG. 4D) may be modified to have such motif, and in situ-polymerization provides an in-situ generated capture structure including an assay analyte (e.g., forming an in situ-generated capture structure 406C of FIG. 4D). Another alternative is to incorporate antibodies within a pre-polymer (like 407B of FIG. 4C), and solidifying the polymer network in situ to provide in situ-generated capture structures already including antibody assay reagents (like 406B of FIG. 4C). Yet another alternative is to introduce the antibodies after the in situ-generated capture structure has been formed (as in the conversion of in situ-generated capture structure 404 to in situ-generated capture structure 406B of FIG. 4C). In one example, biotinylated or streptavidin sites can be introduced either throughout the solidified polymer network of the in situ-generated capture structure or just on the surface, and streptavidin or biotin labeled antibodies may associate with respective binding pairs. Alternatively, a modified antibody may be devised, containing a photoactivatable functionality, such as benzophenone, which may be subjected to photoinitiated insertion into the surface of the solidified polymer network of the in situ-generated capture structure at the same time, or after formation of the in situ-generated capture structure, which would provide a process similar to the conversion of in situ-generated structure 403, including a solidified polymer network, directly to in situ-generated capture structure 406B, where the solidified polymer network of the capture structure includes an assay reagent attached to a functionalized site, of FIG. 4C (process not shown). The same types of conversion strategies can be performed to equivalently introduce an in situ-generated capture structure including an assay analyte.

In one example of a process to introduce a polymer capture structure within a microfluidic device, a solution containing 10% w/v PEGDA (6 Kd) and 1% photoinitiator (IRGACURE 2959, 200 Da) may be flowed into the microfluidic device. After allowing equilibration for less than 10 min, the desired region may be illuminated with UV light at approximately 340 nm (+/−20 nm), having a power of 400 mW/cm$^2$, for 1 second, to initiate polymerization creating an in situ-generated capture structure such as that shown in the FIGS. 4-7.

A method is provided for preparing a microfluidic device including at least a first in situ-generated capture structure, including: providing the microfluidic device, where the microfluidic device comprises an enclosure including a substrate and microfluidic circuit materials, where the enclosure defines a flow region; introducing a first flowable functionalized pre-polymer into the flow region; and activating solidification of the first flowable functionalized pre-polymer at at least one selected area of the enclosure, thereby forming the at least a first in situ-generated capture structure therein. The step of introducing a first flowable functionalized pre-polymer may further include introducing a photoactivatable polymerization initiator into the flow region, where the step of introducing the photoactivatable polymerization initiator may be performed before, concomitantly or after the step of introducing the first flowable pre-polymer. In some embodiments, the enclosure of the microfluidic device further includes at least one sequestration pen fluidically connected to the flow region, and the step of activating solidification includes activating solidification of the first flowable functionalized pre-polymer at at least one selected area of the at least one sequestration pen. The at least first in-situ generated capture structure may include a solidified polymer network including one or more functionalized sites. The one or more functionalized sites may include a biotin, avidin, or streptavidin moiety. The one or more functionalized sites may be covalently bound to at least one component of the first flowable functionalized pre-polymer. Unsolidified flowable functionalized pre-polymer may be flowed out of the microfluidic device. In embodiments, where flowable functionalized pre-polymer has been introduced to the least one sequestration pen, the unsolidified flowable functionalized pre-polymer may diffuse out of the pen, and then it may be flowed out of the microfluidic device The method may further include flowing a first volume of a first fluidic medium through the flow region of the microfluidic device, thereby diffusing unsolidified first flowable functionalized pre-polymer out of the at least one sequestration pen. The method may further include introducing a first functionalized assay reagent or assay analyte to the at least first capture structure within the enclosure, or alternatively within the at least one sequestration pen; and associating the first functionalized assay reagent or assay analyte to the functionalized sites of the solidified polymer network of the at least first capture structure. The first functionalized assay reagent or assay analyte may include an antibody, antigen, organic molecule, or an oligonucleotide. The organic molecule of the first functionalized assay reagent or assay analyte may include a substrate to an enzyme, an antigen, a cell surface marker, a cytokine, or any suitable assay reagent or assay analyte described herein. The first functionalized assay reagent or assay analyte may further include a moiety configured to associate the first functionalized assay reagent or assay analyte with the functionalized site of the solidified polymer network of the at least first capture structure. In various embodiments, the moiety configured to associate the first functionalized assay reagent or assay analyte may include a biotin, avidin or streptavidin binding partner to the functionalized site of the solidified polymer network of the at least first capture structure. In various embodiments, the first functionalized assay reagent or assay analyte may be a first assay reagent. The method may further include flowing a second volume of the first fluidic medium through the microfluidic device, thereby diffusing unassociated first functionalized assay reagent or assay analyte out of the at least one sequestration pen. Once the unassociated functionalized assay reagent or assay analyte has diffused out of the pen, it may be flowed out of the microfluidic device.

The method may further include a step of introducing a second or more functionalized assay reagent or assay analyte. The second or more functionalized assay reagent or assay analyte may associate with a second or more functionalized sites of the solidified polymer network of the at least first capture structure. The second or more functionalized assay reagent or assay analyte may be different from the first functionalized assay reagent or assay analyte and/or detectably differentiable from the first functionalized assay reagent or assay analyte. The second or more functionalized assay reagent or assay analyte may be configured to be detected with a detection reagent that is differentiable from the detection reagent that is used with the first functionalized assay reagent or assay analyte. The second or more functionalized assay reagent or assay analyte may associate with a second or more functionalized site on a second or more capture structure in the enclosure or, alternatively within the at least one sequestration pen.

The method may further include a step of introducing a second or more capture structure in the enclosure, or alternatively within the at least one sequestration pen, where introducing the second or more capture structure may include the steps of: introducing a further volume of the first fluidic medium into the flow region of the microfluidic device; introducing a second flowable functionalized pre-polymer into the flow region; and activating solidification of the second flowable functionalized pre-polymer at at least a second selected area of the enclosure, or alternatively within the at least one sequestration pen, thereby forming the second in situ-generated capture structure therein; and flowing yet another volume of the first fluidic medium intro the flow region of the microfluidic device. The step of introducing the second flowable functionalized pre-polymer may further include introducing a photoactivatable polymerization initiator into the flow region, where the step of introducing the photoactivatable polymerization initiator may be performed before, concomitantly or after the step of introducing the second flowable pre-polymer. After the second capture structure is formed, the second functionalized assay reagent or assay analyte may be flowed in, similarly to the first functionalized assay reagent or assay analyte and allowed to associate with the second capture structure. After association of the second functionalized assay reagent and assay analyte is complete, excess unassociated functionalized assay reagent or assay analyte may be diffused out of the sequestration pen and, optionally, flowed out of the microfluidic device.

The method may further include a step of introducing a third or more capture structure into the at least one sequestration pen, where introducing the third or more capture structure may include: introducing a further volume of the first fluidic medium into the flow region of the microfluidic device; introducing a third flowable functionalized pre-polymer into the flow region; and activating solidification of the third flowable functionalized pre-polymer at at least a third selected area of the enclosure or, alternatively, within the at least one sequestration pen, thereby forming the third in situ-generated capture structure therein; and flowing yet another volume of the first fluidic medium intro the flow region of the microfluidic device. The step of introducing a third flowable functionalized pre-polymer may further include introducing a photoactivatable polymerization initiator into the flow region, where the step of introducing the photoactivatable polymerization initiator may be performed before, concomitantly or after the step of introducing the third flowable pre-polymer. The third functionalized assay reagent or assay analyte may be introduced in a similar manner to the third capture structure, as described above for the first and/or the second functionalized assay reagent or assay analyte. The third functionalized assay reagent or assay analyte may be different from the first or second functionalized assay reagent, and/or may be detectably distinguishable from the first or the second functionalized assay reagent or assay analyte.

In some embodiments, the first flowable functionalized pre-polymer may be different from the second flowable functionalized pre-polymer. In other embodiments, the first flowable functionalized pre-polymer may be the same as the second flowable functionalized pre-polymer. In various embodiments, each of the first, second, and third flowable functionalized pre-polymer may be different from each other. In other embodiments, each of the first, second, and third flowable functionalized pre-polymer may be the same functionalized pre-polymer. In various embodiments of the methods, the solidified polymer network of any of the first, second or third in situ-generated capture structures may include a synthetic polymer, a modified synthetic polymer, or a biological polymer. In some embodiments, the synthetic polymer modifications comprise size modification motifs, cleavage motifs, reactive terminal moieties, and/or cell recognition motifs. The solidified polymer network may include at least one of a polyethylene glycol (PEG), modified polyethylene glycol, polylactic acid (PLA), modified polylactic acid, polyglycolic acid (PGA), modified polyglycolic acid, polyacrylamide (PAM), modified polyacrylamide, poly-N-isopropylacrylamide (PNIPAm), modified poly-N-isopropylacrylamide, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, laminin, modified laminin, polysaccharide, modified polysaccharide, or a co-polymer in any combination. In yet other embodiments, the solidified polymer network may include at least one of a polyethylene glycol, modified polyethylene glycol, polylactic acid (PLA), modified polylactic acid, polyglycolic acid (PGA), modified polyglycolic acid, polyvinyl alcohol (PVA), modified polyvinyl alcohol, polyacrylic acid (PAA), modified polyacrylic acid, fibronectin, modified fibronectin, collagen, modified collagen, laminin, modified laminin, or a co-polymer in any combination. In some embodiments, the polymer of the solidified polymer network may be a modified PEG polymer. The polymer may be a star, 4-arm or 2-arm PEG diacrylate polymer.

Kits.

In yet another aspect, a kit is provided, including: a microfluidic device having an enclosure including a substrate, microfluidic circuit material, and, optionally, a cover, where the enclosure defines a flow region; and a functionalized pre-polymer that can be controllably activated to form a solidified polymer network. The kit can further include an assay reagent or an assay analyte, which may be part of the functionalized pre-polymer, mixed with the functionalized pre-polymer, or provided separately from the functionalized pre-polymer (e.g., in a separate vial, tube, etc.). Alternatively, a kit is provided including: a microfluidic device having an enclosure including a substrate, microfluidic circuit material, and, optionally, a cover, where the enclosure defines a flow region; and at least one in situ-generated capture structure disposed within the enclosure, wherein the at least one in situ-generated capture structure includes a solidified polymer network (e.g., microfluidic device 400, 700). The kit can further include an assay reagent, which may be integral to or associated with the in situ-generated capture structure or which may be provided separately (e.g., in a vial, tube, etc.). The microfluidic device in either kit can include at least one sequestration pen within the enclosure. For kits in which the in situ-generated capture structure is already disposed within the microfluidic device, the in situ-generated capture structure can be located within the flow region, a sequestration pen of the microfluidic device (e.g., an isolation region within the sequestration pen), or both The solidified polymer network may further include one or more functionalized sites. The functionalized sites of the solidified polymer network may be any functionalized sites as described herein, and may include biotin, avidin, streptavidin, or any combination thereof.

In various embodiments of the kit including a microfluidic device including at least one in situ-generated capture structure, the solidified polymer network may include a synthetic polymer, a modified synthetic polymer, or a biological polymer. In embodiments of the kits wherein a functionalized pre-polymer is provided, the functionalized pre-polymer may include a synthetic polymer, a modified synthetic polymer, or a biological polymer. In some embodiments, the synthetic polymer modifications comprise size modification motifs, cleavage motifs, reactive terminal moieties, and/or cell recognition motifs. The solidified polymer network or functionalized pre-polymer may include at least one of a polyethylene glycol (PEG), modified polyethylene glycol, polylactic acid (PLA), modified polylactic acid, polyglycolic acid (PGA), modified polyglycolic acid, polyacrylamide (PAM), modified polyacrylamide, poly-N-isopropylacrylamide (PNIPAm), modified poly-N-isopropylacrylamide, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, laminin, modified laminin, polysaccharide, modified polysaccharide, or a co-polymer in any combination. In yet other embodiments, the solidified polymer network or the functionalized pre-polymer may include at least one of a polyethylene glycol, modified polyethylene glycol, polylactic acid (PLA), modified polylactic acid, polyglycolic acid (PGA), modified polyglycolic acid, polyvinyl alcohol (PVA), modified polyvinyl alcohol, polyacrylic acid (PAA), modified polyacrylic acid, fibronectin, modified fibronectin, collagen, modified collagen, laminin, modified laminin, or a co-polymer in any combination. In some embodiments, the polymer of the solidified polymer network or of the functionalized pre-polymer may be a modified PEG polymer. The polymer may be a star, 4-arm or 2-arm PEG diacrylate polymer. In various embodiments, wherein the enclosure or at least one sequestration pen includes more than one in situ-generated capture structure, each of the capture structures include the same polymer, or may alternatively include polymers that are different for each of the first in situ-generated capture structure, the second in situ-generated capture structure, the third in situ-generated capture structure, and so on. In kits providing a functionalized pre-polymer, more than one functionalized prepolymer may be provided. The kit may include more than one polymer, which can be combined together with the at least first functionalized polymer to form a flowable polymer solution configured to be solidified to form a solidified polymer network. The at least first functionalized polymer may be provided as a flowable polymer solution or may be provided as a gel, dehydrated, or lyophilized form, any of which may be configured to be formulated by the end user as a flowable polymer solution by dilution with a fluidic medium. Other polymers provided in the kit, which may be used to form the in situ-generated capture structure, may be provided in one or more separate containers from the at least first functionalized polymer.

The assay reagent or assay analyte of the kit may be any assay reagent or assay analyte described herein. The assay reagent or assay analyte may include a functional moiety configured to associate with the functionalized sites of the solidified polymer network of the at least one capture structure. The assay reagent or assay analyte may be provided in a formulation configured to be ready to introduce into the flow region of the microfluidic device. Alternatively, the assay reagent or assay analyte may be provided in a solid or lyophilized form, with instructions for dissolution into an appropriate medium for introduction into the microfluidic device and subsequent association with the functionalized sites of the solidified polymer network of the in situ-generated capture structure. In some embodiments of the kits, more than one assay reagent or more than one assay analyte, in any suitable combination, may be provided for multiplex experiments, and may any of the assay reagents or analytes as described in the following paragraphs.

In various embodiments of the kits including a microfluidic device including at least one in situ-generated capture structure, the solidified polymer network of the in situ-generated capture structure may already include an assay reagent or assay analyte (e.g., microfluidic device 450, where the assay reagent or assay analyte is already present within/on the solidified polymer network of the at least one capture structure of the microfluidic device as supplied). The assay reagent or assay analyte may be covalently or non-covalently bound to the one or more functionalized sites of the solidified polymer network. In some embodiments, the assay reagent or assay analyte may be non-covalently bound to the one or more functionalized sites of the solidified polymer network via a biotin/streptavidin or biotin/avidin complex.

Whether the assay reagent or assay analyte is provided already incorporated as part of the solidified polymer network of the in situ-generated capture structure or as a component of a kit to prepare an in situ-generated capture structure having such assay reagent or assay analyte, the assay reagent or assay analyte may be any suitable moiety as described herein. The assay reagent or assay analyte, incorporated or to be incorporated within an in situ-generated capture structure, may be a protein, a nucleic acid, an organic molecule, or a saccharide. In some embodiments of the kit including a microfluidic device including at least one in situ-generated capture structure, the assay reagent or assay analyte may be an antibody, and may be any kind of antibody as described herein. In other embodiments, the assay reagent or assay analyte, incorporated or to be incorporated within an in situ-generated capture structures may be an antigen. The assay reagent or assay analyte that is an antigen may be any suitable antigen as described herein. In yet other embodiments, the assay reagent, incorporated or to be incorporated within an in situ-generated capture structure may be is an oligonucleotide. The oligonucleotide assay reagent may be any suitable oligonucleotide as described herein.

In some embodiments of the kits, the assay reagent or assay analyte may include a detectable label. The detectable label of the assay reagent or assay analyte may be a fluorescent, colorimetric, or luminescent label. In some embodiments, when the assay reagent or assay analyte includes a detectable label, the label is not detectable until the assay process is underway, and the detectable label is generated or liberated from the assay reagent or assay analyte.

In other embodiments of the kits, the kit may further include a detection reagent. The detection reagent may include a detectable label. The detectable label of the detection reagent may include a fluorescent, colorimetric, or luminescent label. In some embodiments, the detectable label of the detection reagent may be fluorescent. In some embodiments, the detection reagent includes at least a first antibody. In some embodiments, the detection reagent may include a second antibody, where the second antibody is a secondary antibody to the assay process and incorporates the detectable label for the combination of the first and second antibody that comprises the detection reagent. In other embodiments, the detection reagent may include an intercalating dye. In yet other embodiments, the detection reagent may include a FRET labeled oligonucleotide, which may be any FRET labeled oligonucleotide as described herein.

In various embodiments of the kits, the more than one detection reagent may be provided. A first detection reagent of the more than one detection reagent may be spectrally distinct from a second detection reagent, and so on for each different assay reagent or assay analyte.

In other embodiments of the kits, the microfluidic device may include two or more capture structures disposed within the enclosure, or, alternatively, within a sequestration pen therein, where a first solidified polymer network of a first capture structure already includes/is designed to incorporate a first assay reagent or assay analyte and a second solidified polymer network of a second capture structure already includes/or is designed to incorporate a second assay reagent or assay analyte, and so on for each additional capture structure in the enclosure or, alternatively, the at least one sequestration pen. The first assay reagent or assay analyte may be different from the second assay reagent or assay analyte, and so on for each additional assay reagent or assay analyte incorporated or designed to be incorporated within each additional capture structure in the at least one sequestration pen. The first capture structure and the second capture structure may be disposed in different locations within the enclosure, or at least one sequestration pen therein, of the microfluidic device.

When a first capture structure incorporates or is designed to incorporate a first assay reagent or assay analyte, and a second capture structure incorporates or is designed to incorporate a second assay reagent or assay analyte, the kit may further include a respective first detection reagent and a second detection reagent, where the first detection reagent may be different from the second detection reagent. The first detection reagent and the second detection reagent, and so on, for any additional assay reagents or analytes incorporated or configured to be incorporated on capture structures, may include any detection reagent as described herein, and may be selected independently. In some embodiments, the first detection reagent may include at least a first primary antibody and the second detection reagent comprises at least a second primary antibody directed to the respective biological targets of each assay. Each detection reagent including a primary antibody may further include a secondary antibody, which itself may include the detectable label for each assay being performed. When more than one capture structure is provided in the enclosure, or alternatively in the at least one sequestration pen therein, either each of the labels of the respective detection reagents are spectrally distinct or the labels of the respective detection reagents are spatially distinct. In some embodiments, the labels are both spectrally and spatially distinct.

In various embodiments of the kit including a microfluidic device including at least one in situ-generated capture structure, the microfluidic device may further include a plurality of sequestration pens. In some embodiments, each of the plurality of sequestration pens may include at least one capture structure comprising a solidified polymer network. The plurality of sequestration pens may be configured as described for any sequestration pen described herein and in any combination. The microfluidic device of the kit may further include any component or feature of any of microfluidic devices 100, 200, 23, 250, 280, 290, 320, 400, 450, 500, 700 as described herein, in any combination.

In some embodiments of the kits, one or more fluidic media may be included, and may further include one or more additives described herein to provide enhanced growth, viability or portability, including additives for a dynamic coating within the microfluidic device. In other embodiments of the kit, one or more of the surfaces of the enclosure may include a coating. The coating may be any coating as described herein. In some embodiments, the coating is a covalent coating that provides a conditioned surface. The covalent coating may be present on all the interior surfaces of the enclosure of the microfluidic device. In some embodiments, the covalent coating providing a conditioned surface may be hydrophilic.

In various embodiments of the kits, the kit may further include a photoactivatable polymerization initiator. The photoactivatable polymerization initiator may be provided in a separate container from the fluidic medium and/or functionalized pre-polymer(s).

Example 1. Hydrogel Cytokine Assay

T Cells.
CD3+ cells from AllCells Inc. and mixed with anti-CD3/anti-CD28 magnetic beads (Dynabeads®, ThermoFisher Scientific, Cat. No. 11453D) at a ratio of 1 bead/1 cell. The mixture was incubated in the same medium as the culturing experiment itself, for 48 hours in a 5% $CO_2$ incubator at 37° C. Following the incubation, the T cell/bead mixture was resuspended for use.

Culture Medium.
RPMI-1640 (GIBCO®, ThermoFisher Scientific, Cat. No. 11875-127), 10% FBS, 2% Human AB serum (50 U/ml IL2; R&D Systems).

Priming Procedure:
250 microliters of 100% carbon dioxide was flowed in at a rate of 12 microliters/sec. This was followed by 250 microliters of PBS containing 0.1% Pluronic® F27 (Life Technologies® Cat # P6866), flowed in at 12 microliters/sec. The final step of priming included 250 microliters of PBS, flowed in at 12 microliters/sec. Introduction of the culture medium follows.

Perfusion Regime (During Cell Culturing on Chip:
The perfusion method was either of the following two methods:
1. Perfuse at 0.01 microliters/sec for 2 h; perfuse at 2 microliters/sec for 64 sec; and repeat.
2. Perfuse at 0.02 microliters/sec for 100 sec; stop flow 500 sec; perfuse at 2 microliters/sec for 64 sec; and repeat.

System and Microfluidic Device:
Manufactured by Berkeley Lights, Inc. The system included at least a flow controller, temperature controller, fluidic medium conditioning and pump component, light source for light activated DEP configurations, microfluidic device, mounting stage, and a camera. The sequestration pens have a volume of about 7×10$^5$ cubic microns.

Hydrogel Preparation.

Streptavidin amine (Nanocs) in N-morpholino ethanesulfonic acid (MES) was diluted in 0.1M carbonate-bicarbonate (CBB buffer at pH 9.0) and reacted with Ac-PEG-hydroxysuccinimide in a ratio calculated to provide a 5% wt percentage for a final concentration of 10 mg/200 microliter. The reaction was continued at least overnight at 4° C.

A solution of Igracure photoinitiator at 0.606 wt % solution in deionized ultra filtered water (DIUF) was made.

The prepolymer for the functional hydrogel was made by solubilizing a 5 wt % solution of Ac PEG star solid (4 arm PEG acrylate (10 k MW) from Laysan Bio (#4arm-PEG-ACRYL-10 k-1 g)) in the 0.606% photoinitiator solution.

A 160 microliter prepolymer lot was made by combining 28 microliter of the NHS-PEG-streptavidin conjugate and 132 microliters of the Ac PEG star acrylate/photoinitiator solution.

A primed microfluidic device was loaded with the prepolymer solution at 0.5 microliter/sec, and incubated for at least 1 hour prior to photoinitiation to allow diffusion of prepolymer into pens of the microfluidic device. After incubation was complete, a 10 sec exposure to light was used to initiate polymer solidification at the bottom corner of pens.

After solidification was initiated, a set of rinses were used to remove excess soluble polymers and initiator, including 2×250 microliters PBS at 8 microliters/sec; 250 microliters PBS at 0.2 microliters/sec; and an overnight rinse in PBS (250 microliters at 0.005 microliters/sec).

Hydrogel Functionalization.

The hydrogel prepared microfluidic device was loaded with 1 microgram/mL capture antibody (Biotinylated goat anti-human TNF alpha from R&D Systems (# BAF210) where the in situ-generated capture antibody solution was flowed in within 250 microliters at 5 microliters/sec, followed by a second flow period of 250 microliters of the in situ-generated capture antibody solution at 0.075 microliters/sec. After completing the introduction of the in situ-generated capture antibody, the microfluidic device was flushed with PBS (250 microliters at 5 microliters/sec)×5.

T-Cell Introduction and Detection of TNF Alpha.

T-cells were introduced and cultured for overnight at 37° C. A first detection antibody was introduced after the end of the incubation period, by flowing a solution of Rabbit anti-human TNF alpha from Abcam (# ab9635), within 250 microliters at 5 microliters/sec, followed by a second flow period of 250 microliters of the first detection antibody solution at 0.075 microliters/sec. After completing the introduction of the first detection antibody, the microfluidic device was flushed with PBS (250 microliters at 5 microliters/sec)×5.

A secondary detection antibody (Alexa 488 goat anti-rabbit IgG from Life Technologies (# A11053)) was then introduced at a concentration of 2 micrograms/ml by flowing 250 microliters of the solution at 5 microliters/sec; followed by a second 250 microliter flow of the 2 microgram/ml solution at 0.075 microliter/sec.

Figure 6A:
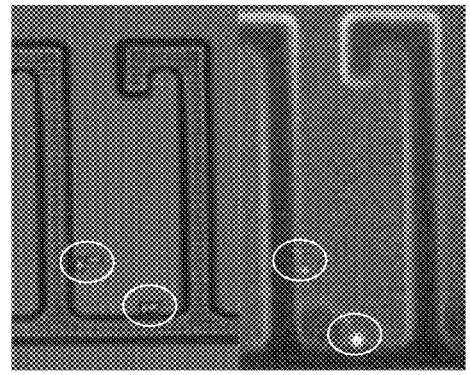
FIGS. 6A-6C are photographic representations of in-situ generated assay structures detecting low, medium and high secreted amounts of cytokine secreted by a biological micro-object.
Figure 6B:
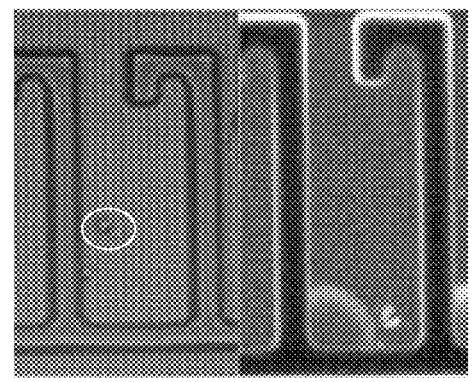
Figure 6C:
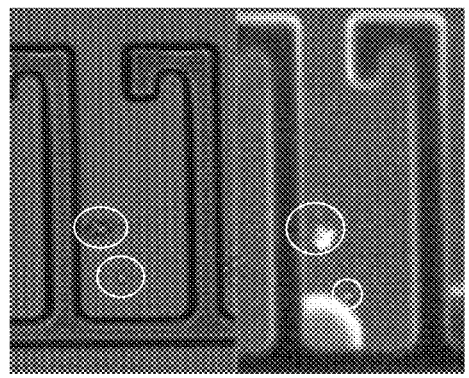

FIGS. 6A-C showed the ability to differentiate between highly secreting T cells, moderately secreting T cell and poorly secreting T cells. In FIG. 6A, fluorescence is just detectable for this pen containing poorly secreting T cell(s). The left hand image is brightfield, and four cells may be seen, while the right hand image shows the fluorescence image of the same pen, where the functionalized hydrogel is faintly visible at the lower left corner of the pen.

FIG. 6B shows a moderately secreting set of T cells. The left hand image is that of one to three T cells in a different pen, and the right hand fluorescence image of that same pen clearly shows significant fluorescence concentrated at the surface of the functionalized hydrogel in the lower left corner of the pen.

FIG. 6C shows a highly secreting set of T cells in a third pen. The left hand image in FIG. 6C is brightfield and shows a group of about 4-5 T cells in a clump as well as one solo cell. The right hand image shows the same third pen under fluorescent detection where both the functionalized hydrogel is well illuminated as well as the clump of cells in the pen.

This example clearly demonstrated that differing levels of TNF alpha cytokine production can be detected and ranked within the microfluidic pens.

Microfluidic Devices and Systems for Operating and Observing Such Devices.

FIG. 1A illustrates an example of a microfluidic device 100 and a system 150 which can be used for generation of embryos in vitro, including selecting and evaluating ova and/or oocytes and/or sperm. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device 194 (incorporated within imaging module 164, where device 194 is not illustrated in FIG. 1A, per se), and a tilting device 190 (part of tilting module 166, where device 190 is not illustrated in FIG. 1A).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 (part of imaging module 164, discussed below) can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 02°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful in producing an embryo, such as isolating one ovum from an adjacent ovum. Testing, stimulating and fertilizing may all be performed on an individual basis and, in some embodiments, may be performed on an individual time scale. In some embodiments, the microfluidic circuit 120 comprises a plurality of identical microfluidic sequestration pens.

In some embodiments, the microfluidic circuit 120 comprises a plurality of microfluidic sequestration pens, wherein two or more of the sequestration pens comprise differing structures and/or features which provide differing benefits in producing embryos. One non-limiting example may include maintaining ova in one type of pen while maintaining sperm in a different type of pen. In another embodiment, at least one of the sequestration pens is configured to have electrical contacts suitable for providing electrical activation for an ovum. In yet another embodiment, differing types of cells (such as, for example, uterine cells, endometrial cells, PEG (intercalary) cells derived from the uterine tube (e.g., oviduct or Fallopian tube), cumulus cells, or a combination thereof) may be disposed in sequestration pens adjacent to a sequestration pen containing an ovum, such that secretions from the surrounding sequestration pens may diffuse out of each respective pen and into the pen containing an ovum, which is not possible with macroscale in-vitro culturing and fertilization. Microfluidic devices useful for producing an embryo may include any of the sequestration pens 124, 126, 128, and 130 or variations thereof, and/or may include pens configured like those shown in FIGS. 2B, 2C, 2D, 2E and 2F, as discussed below.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
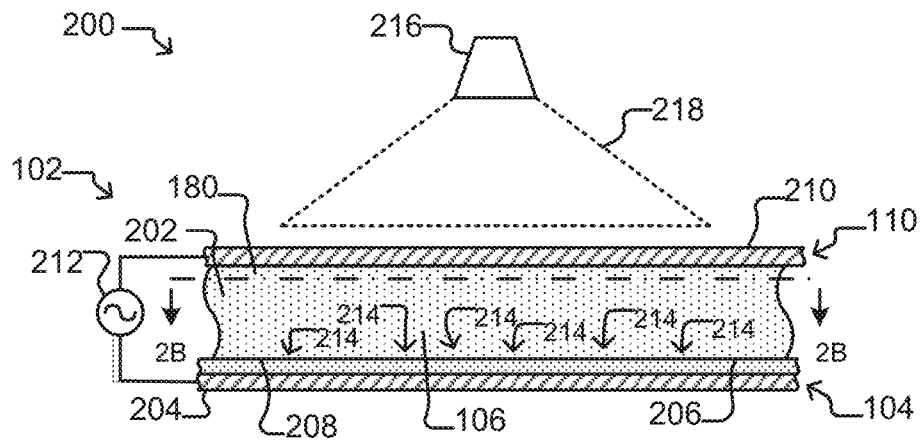
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which oocytes, ova, or embryos can be placed, cultured, and/or monitored have been described, for example, in US 2014/0116881 (application Ser. No. 14/060,117, filed Oct. 22, 2013), US 2015/0151298 (application no. Ser. No. 14/520,568, filed Oct. 22, 2014), and US 2015/0165436 (application no. Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic Device Motive Configurations.

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
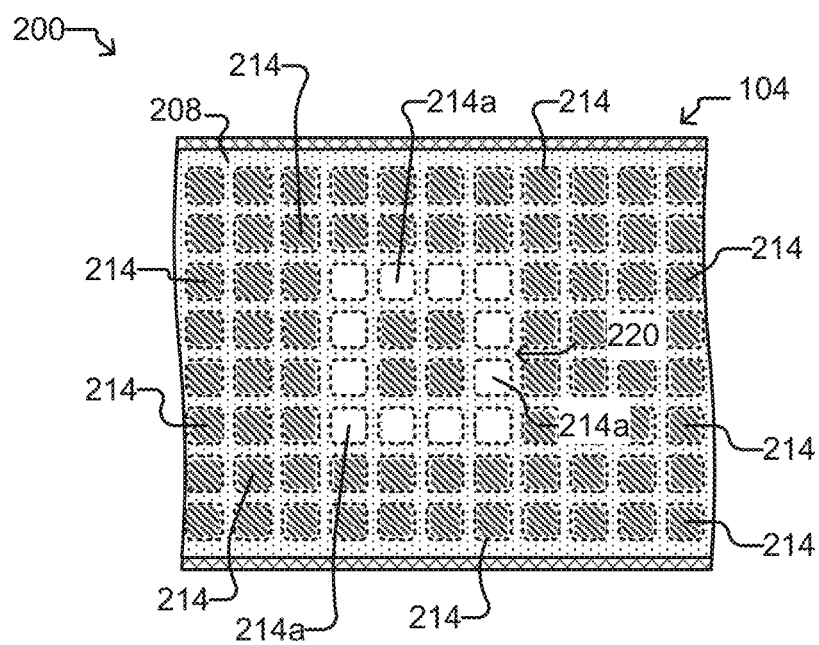

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 μm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 204, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration Pens.

Figure 2A:
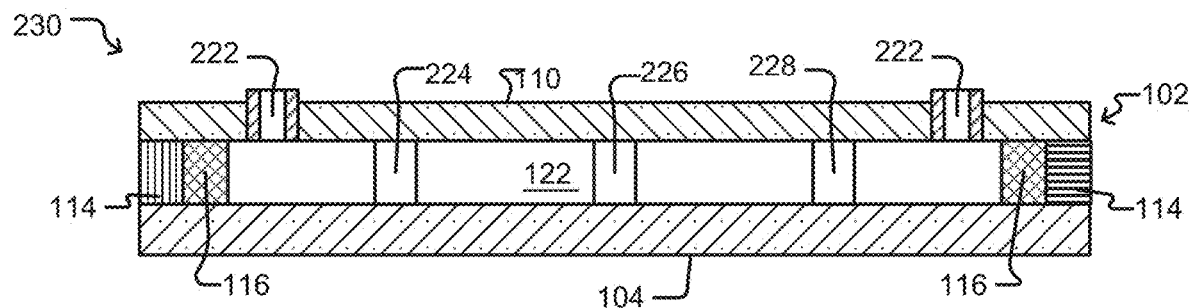
FIGS. 2A and 2B illustrate isolation pens according to some embodiments of the disclosure.
Figure 2B:
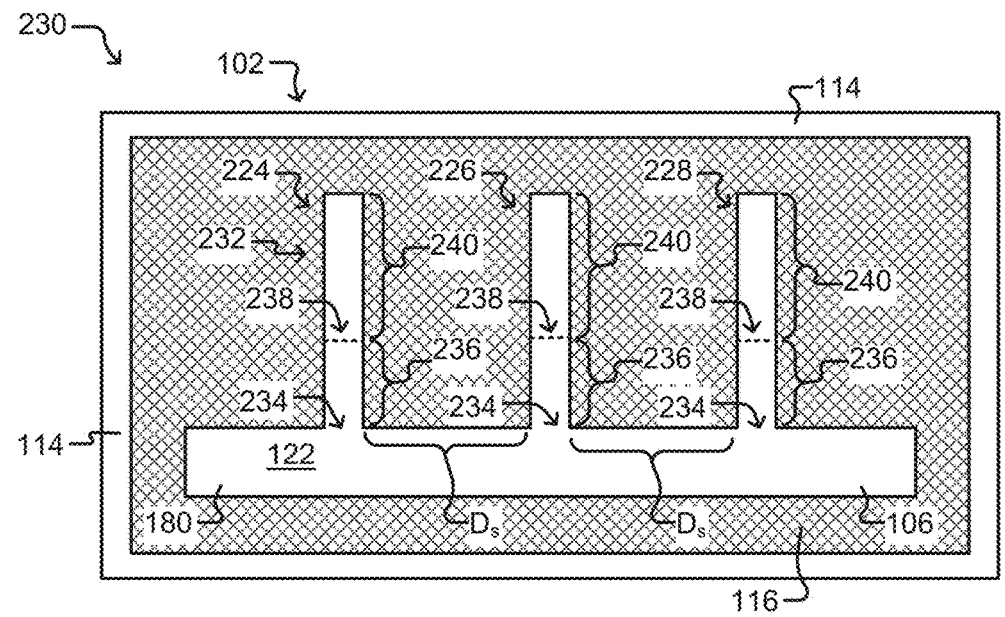
Figure 2C:
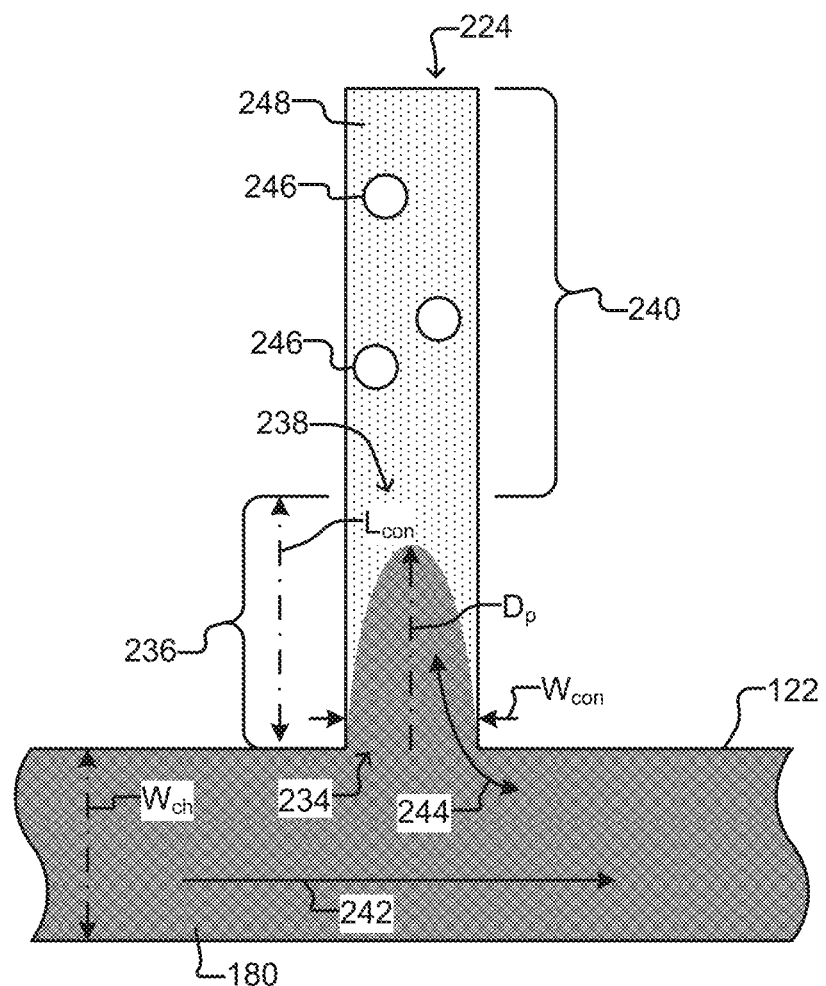
FIG. 2C illustrates a detailed sequestration pen according to some embodiments of the disclosure.

Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290, 320, 400, 450, 500, 700 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length Lon of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be in any of the ranges identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be in any of the ranges identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
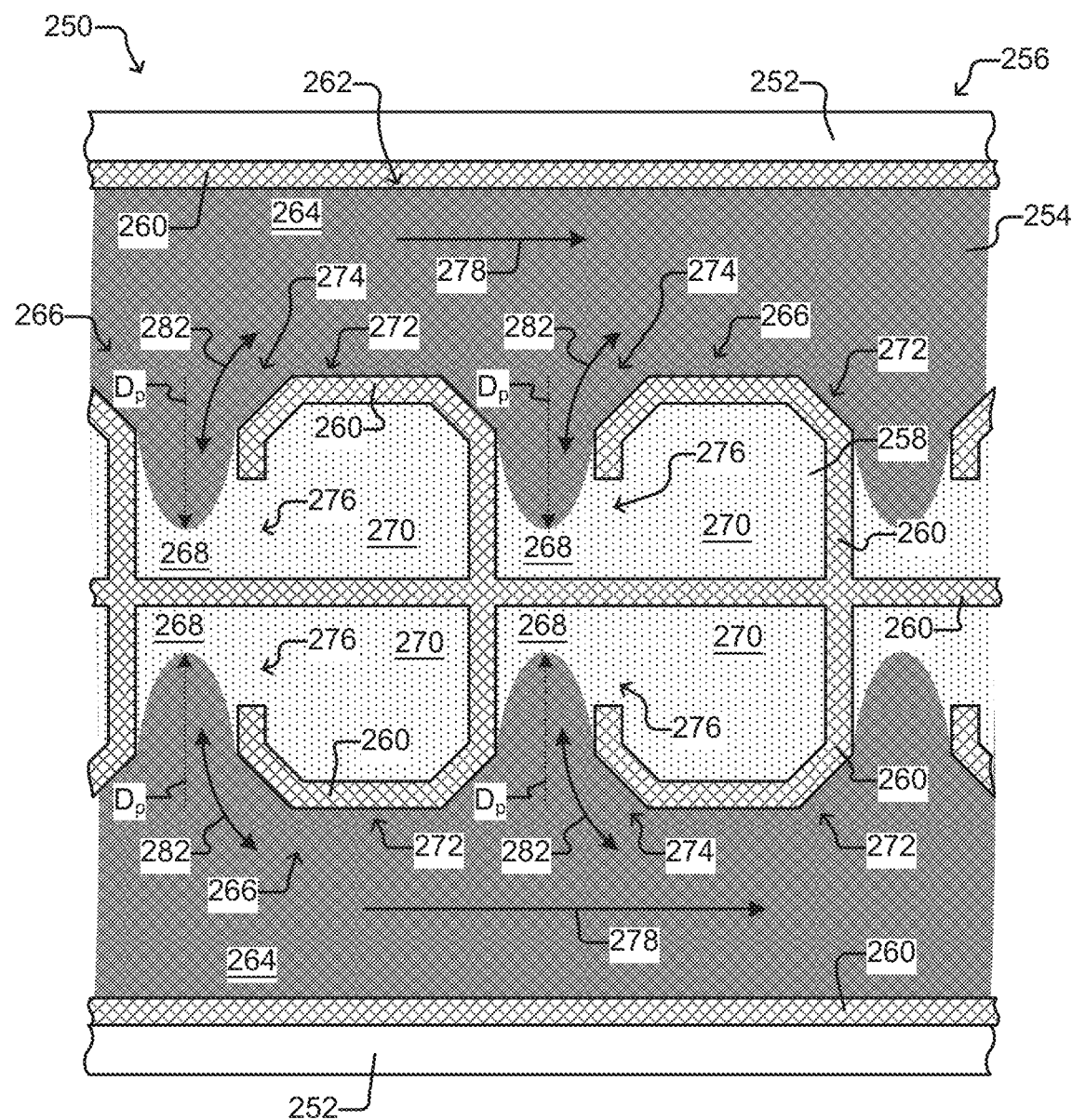
FIGS. 2D-F illustrate sequestration pens according to some other embodiments of the disclosure.
Figure 2E:
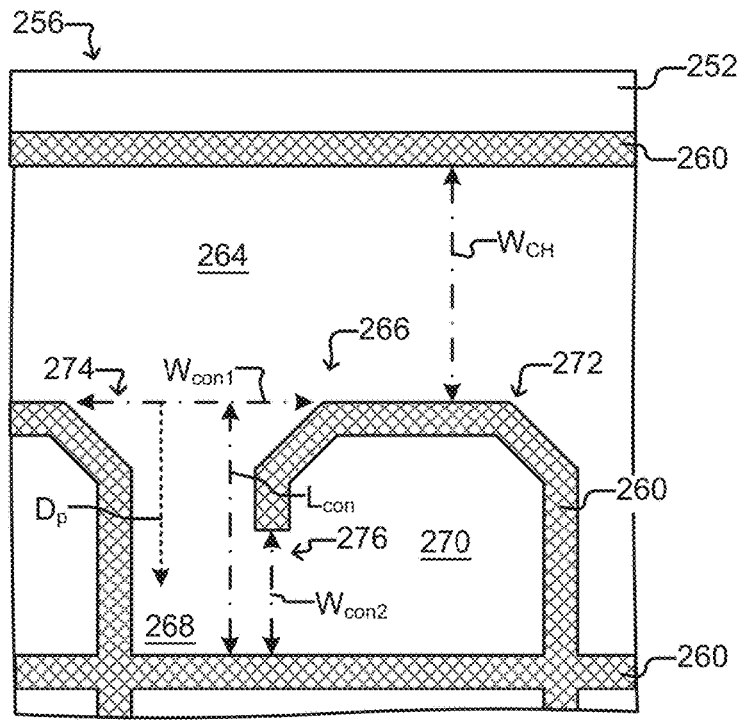
Figure 2F:
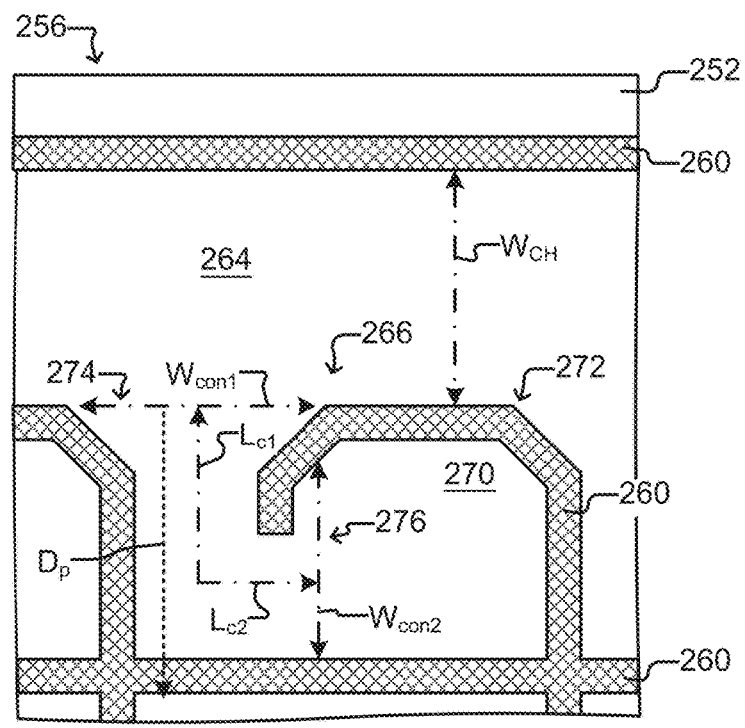

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290, 320, 400, 450, 500, 700. Likewise, the microfluidic device 250 is another variant of the microfluidic device 100, and may also have the same or a different DEP configuration as the above-described microfluidic device 100, 200, 230, 280, 290, 320, 400, 450, 500, 700 as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles in any of the following ranges: from about 30° to about 90°, from about 45° to about 90°, from about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the microfluidic channel (e.g., 122) at a proximal opening (e.g. 234) can be within any of the following ranges: about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. In some other embodiments, the width $W_{ch}$ of the microfluidic channel (e.g., 122) at a proximal opening (e.g. 234) can be in a range of about 200-800 microns, 200-700 microns, or 200-600 microns. The foregoing are examples only, and the width $W_{ch}$ of the microfluidic channel 122 can be in other ranges (e.g., a range defined by any of the endpoints listed above). Moreover, the $W_{ch}$ of the microfluidic channel 122 can be selected to be in any of these ranges in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1 \times 10^4$-$3 \times 10^6$ square microns, $2 \times 10^4$-$2 \times 10^6$ square microns, $4 \times 10^4$-$1 \times 10^6$ square microns, $2 \times 10^4$-$5 \times 10^5$ square microns, $2 \times 10^4$-$1 \times 10^5$ square microns or about $2 \times 10^5$-$2 \times 10^6$ square microns.

In various embodiments of sequestration pens, the height $H_{ch}$ of the microfluidic channel (e.g., 122) at a proximal opening (e.g., 234) can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be in other ranges (e.g., a range defined by any of the endpoints listed above). The height $H_{ch}$ of the microfluidic channel 122 can be selected to be in any of these ranges in regions of the microfluidic channel other than at a proximal opening of an sequestration pen.

In various embodiments of sequestration pens a cross-sectional area of the microfluidic channel (e.g., 122) at a proximal opening (e.g., 234) can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be in other ranges (e.g., a range defined by any of the endpoints listed above).

In various embodiments of sequestration pens, the length $L_{con}$ of the connection region (e.g., 236) can be in any of the following ranges: about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in a different range than the foregoing examples (e.g., a range defined by any of the endpoints listed above).

In various embodiments of sequestration pens the width $W_{con}$ of a connection region (e.g., 236) at a proximal opening (e.g., 234) can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{con}$ of a connection region (e.g., 236) at a proximal opening (e.g., 234) can be at least as large as the largest dimension of a micro-object (e.g., biological cell which may be a T cell, B cell, or an ovum or embryo) that the sequestration pen is intended for. For example, the width $W_{con}$ of a connection region 236 at a proximal opening 234 of an sequestration pen that an oocyte, ovum, or embryo will be placed into can be in any of the following ranges: about 100 microns, about 110 microns, about 120 microns, about 130 microns, about 140 microns, about 150 microns, about 160 microns, about 170 microns, about 180 microns, about 190 microns, about 200 microns, about 225 microns, about 250 microns, about 300 microns or about 100-400 microns, about 120-350 microns, about 140-300 microns, or about 140-200 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{pr}$ of a proximal opening of a connection region may be at least as large as the largest dimension of a micro-object (e.g., a biological micro-object such as a cell) that the sequestration pen is intended for. For example, the width $W_{pr}$ may be about 50 microns, about 60 microns, about 100 microns, about 200 microns, about 300 microns or may be in a range of about 50-300 microns, about 50-200 microns, about 50-100 microns, about 75-150 microns, about 75-100 microns, or about 200-300 microns In various embodiments of sequestration pens, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length Lon of a connection region 236 to a width $W_{con}$, of the connection region 236 at the proximal opening 234 can be different than the foregoing examples.

In various embodiments of microfluidic devices 100, 200, 23, 250, 280, 290, 320, 400, 450, 500, 700, $V_{max}$ can be set around 0.2, 0.3, 0.4, 0.5, 0.6, 0.7, 0.8, 0.9, 1.0, 1.1, 1.2, 1.3, 1.4, or 1.5 microliters/sec.

In various embodiments of microfluidic devices having sequestration pens, the volume of an isolation region (e.g., 240) of a sequestration pen can be, for example, at least $5 \times 10^5$, $8 \times 10^5$, $1 \times 10^6$, $2 \times 10^6$, $4 \times 10^6$, $6 \times 10^6$, $8 \times 10^6$, $1 \times 10^7$, $5 \times 10^7$, $1 \times 10^8$, $5 \times 10^8$, or $8 \times 10^8$ cubic microns, or more. In various embodiments of microfluidic devices having sequestration pens, the volume of a sequestration pen may be about $5 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, or about 1000 to about 3500 sequestration pens. The sequestration pens need not all be the same size and may include a variety of configurations (e.g., different widths, different features within the sequestration pen).

Figure 2G:
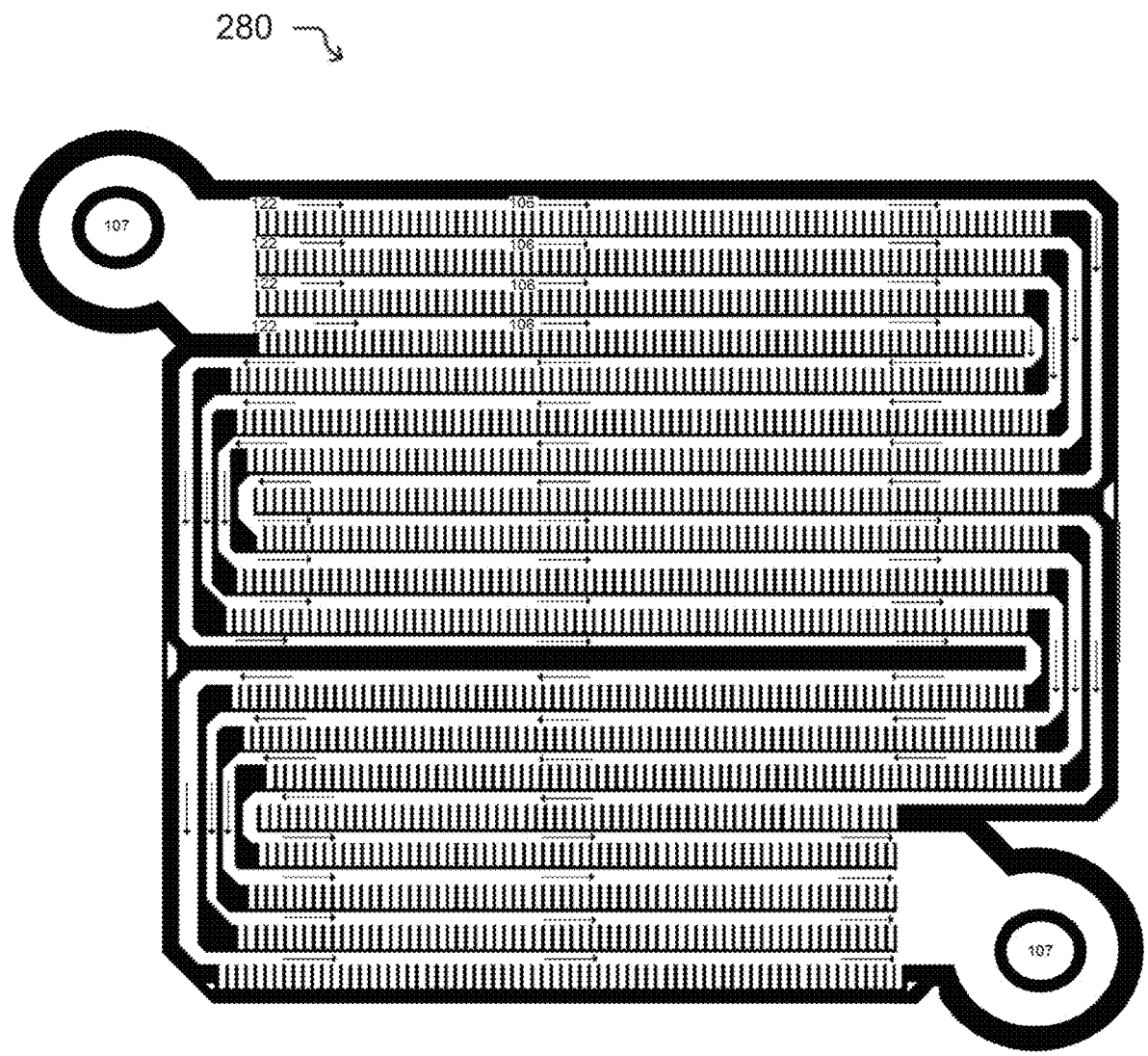
FIG. 2G illustrates a microfluidic device according to an embodiment of the disclosure.

FIG. 2G illustrates a microfluidic device 280 according to one embodiment. The microfluidic device 280 illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
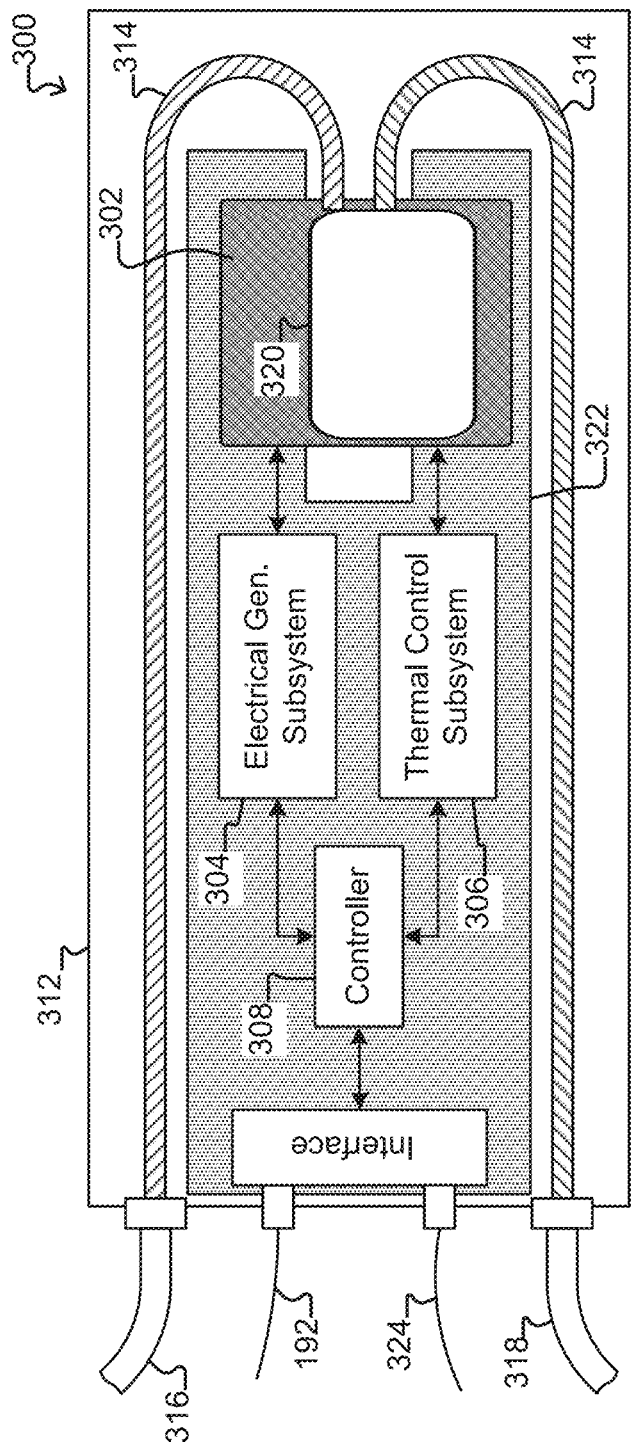
FIG. 3A illustrates a specific example of a system for use with a microfluidic device and associated control equipment according to some embodiments of the disclosure.
Figure 3B:
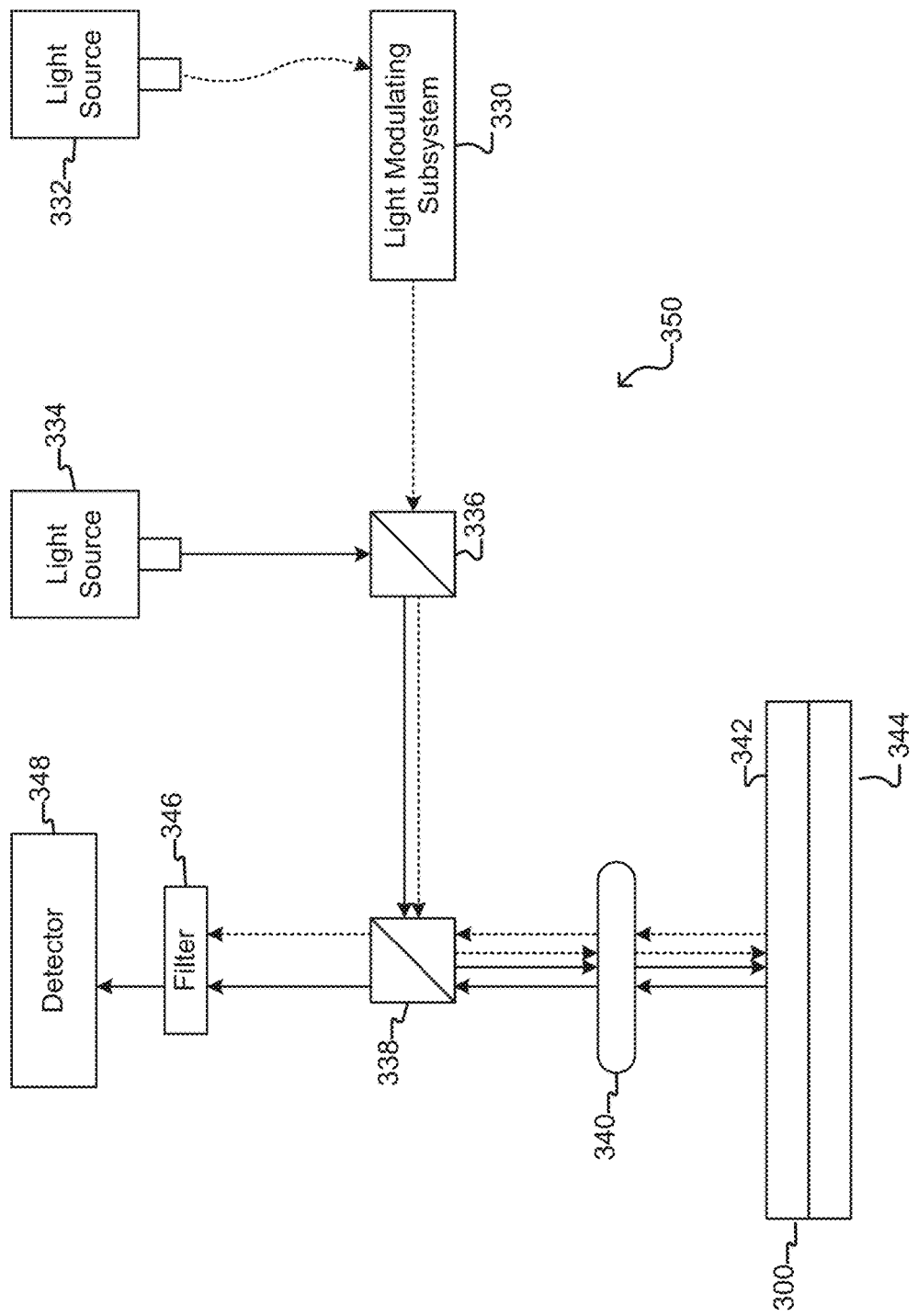
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290, 320, 400, 450, 500, 700) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient +/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. One example of a suitable light modulating subsystem 330 is the Mosaic™ system from Andor Technologies™. In certain embodiments, imaging module 164 and/or motive module 162 of system 150 can control the light modulating subsystem 330.

In certain embodiments, the imaging device 194 further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Coating Solutions and Coating Agents.

Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating Agent/Solution.

Any convenient coating agent/coating solution can be used, including but not limited to: serum or serum factors, bovine serum albumin (BSA), polymers, detergents, enzymes, and any combination thereof.

Polymer-Based Coating Materials.

The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a range of form about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a range of from about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently Linked Coating Materials.

In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may comprises carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned Surface Properties.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface has a thickness in the range of about 1 nm to about 10 nm; about 1 nm to about 7 nm; about 1 nm to about 5 nm; or any individual value therebetween. In other embodiments, the conditioned surface formed by the covalently linked moieties may have a thickness of about 10 nm to about 50 nm. In various embodiments, the conditioned surface prepared as described herein has a thickness of less than 10 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). These values are in contrast to that of a CYTOP® (Asahi Glass Co., Ltd. JP) fluoropolymer spin coating, which has a thickness in the range of about 30 nm. In some embodiments, the conditioned surface does not require a perfectly formed monolayer to be suitably functional for operation within a DEP-configured microfluidic device.

In various embodiments, the coating material providing a conditioned surface of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-Part Conditioned Surface.

The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of Preparing a Covalently Linked Coating Material.

In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

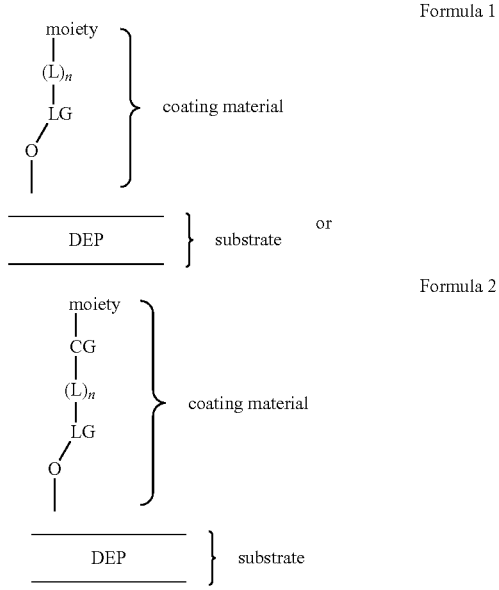

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group consisting of ether, amino, carbonyl, amido, or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide in a range from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
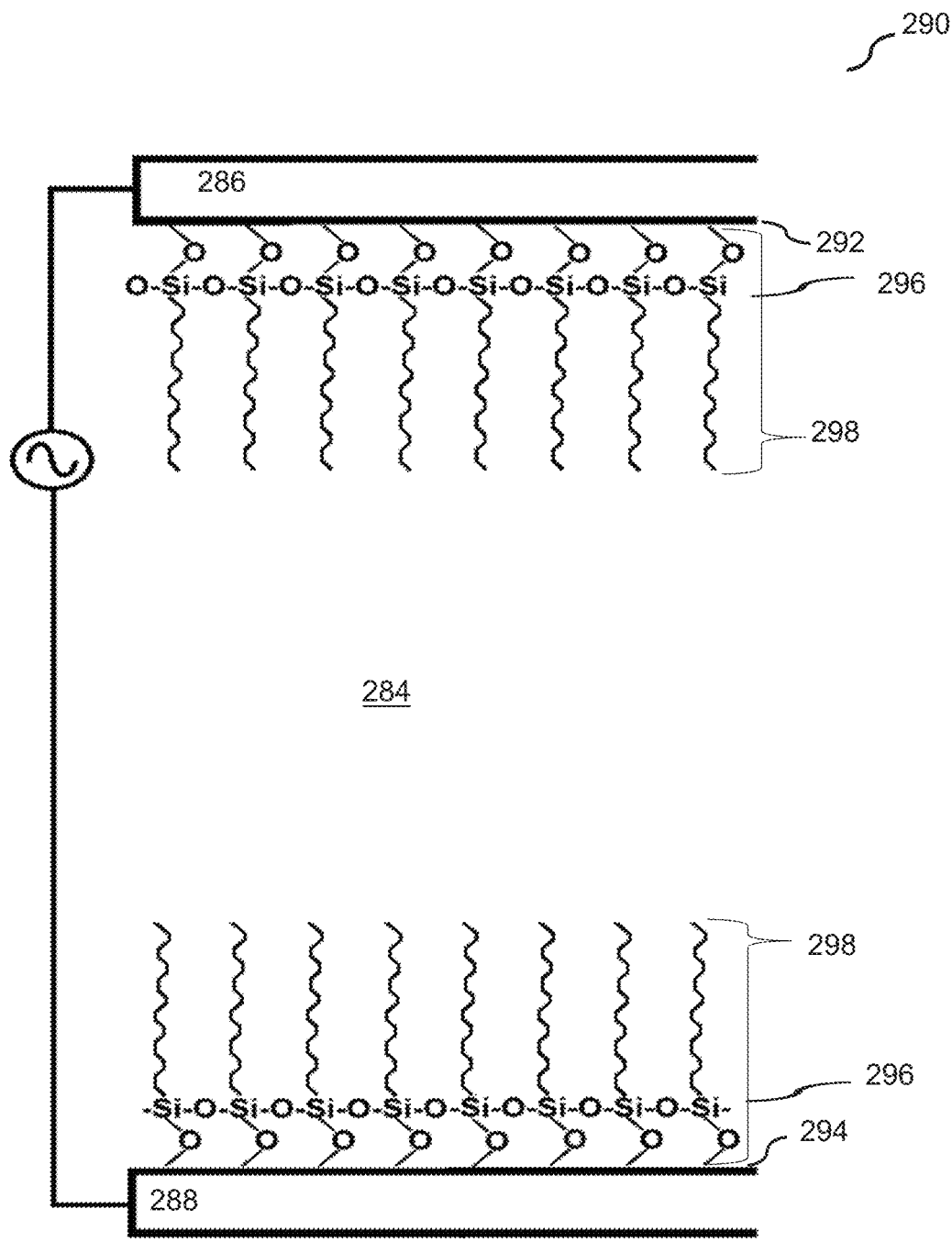
FIG. 2H illustrates a coated surface of the microfluidic device according to an embodiment of the disclosure.

FIG. 2H depicts a cross-sectional views of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated, a fluoroalkyl terminated moiety, a PEG-terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate).

Further details of appropriate coating treatments and modifications may be found at U.S. application Ser. No. 15/135,707, filed on Apr. 22, 2016, and is incorporated by reference in its entirety.

Additional System Components for Maintenance of Viability of Cells within the Sequestration Pens of the Microfluidic Device.

In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

Recitation of Some Embodiments of the Microfluidic Devices, Methods and Kits

1. A microfluidic device including: an enclosure including a substrate and a microfluidic circuit material, the enclosure defining a flow region; and at least one in situ-generated capture structure disposed within the enclosure, and optionally within the flow region, where the at least one in situ-generated capture structure comprises a solidified polymer network.

2. The microfluidic device of embodiment 1, where the solidified polymer network may include one or more functionalized sites.

3. The microfluidic device of embodiment 1 or 2, where the solidified polymer network may include an assay reagent or assay analyte.

4. The microfluidic device of any one of embodiments 1-3, where the enclosure of the microfluidic device may include at least one sequestration pen, and optionally a proximal opening of the sequestration pen to the flow region may be oriented substantially parallel to an average direction of flow of fluidic medium in the flow region.

5. The microfluidic device of embodiment 4, where the at least one sequestration pen may include an isolation region and a connection region, the connection region having a proximal opening to the flow region and a distal opening to the isolation region.

6. The microfluidic device of embodiment 4 or 5, where the one or more in situ-generated capture structures may be disposed within the sequestration pen, and optionally within the isolation region of the sequestration pen.

7. The microfluidic device of any one of embodiments 3-6, where the assay reagent may be covalently attached to the solidified polymer network.

8. The microfluidic device of any one of embodiments 3-6, where the assay reagent may be non-covalently attached to the solidified polymer network.

9. The microfluidic device of embodiment 8, where the assay reagent may be non-covalently attached to the solidified polymer network via a biotin/streptavidin complex.

10. The microfluidic device of any one of embodiments 3-9, where the assay reagent may be a protein, a nucleic acid, an organic molecule, and/or a saccharide.

11. The microfluidic device of embodiment 10, where the assay reagent may include an antibody.

12. The microfluidic device of embodiment 10, where the assay reagent may include an antigen.

13. The microfluidic device of embodiment 10, where the assay reagent may include a capture oligonucleotide.

14. The microfluidic device of any one of embodiments 3-6, where the assay analyte may be non-covalently bound to the solidified polymer network of the at least one in situ-generated capture structure.

15. The microfluidic device of any one of embodiments 3-6 or 14, where the assay analyte may include a protein.

16. The microfluidic device of any one of embodiments 3-6 or 14, where the assay analyte may include an oligonucleotide.

17. The microfluidic device of any one of embodiments 3-6 or 14, where the assay analyte may include an antibody or a cytokine.

18. The microfluidic device of any one of embodiments 3-6 or 14, where the assay analyte may include an organic molecule.

19. The microfluidic device of any one of embodiments 1-18, where two or more in situ-generated capture structures may be disposed in the flow region and/or the at least one sequestration pen.

20. The microfluidic device of embodiment 19, where a first capture structure of the two or more in situ-generated capture structures may bind to a first assay reagent or a first assay analyte, and a second capture structure of the two or more in situ-generated capture structures may bind to a second assay reagent or a second assay analyte, where the first assay reagent or first assay analyte is different from the second assay reagent or second assay analyte.

21. The microfluidic device of embodiment 19 or 20, where each of the two or more in situ-generated capture structures may be disposed at a different location in the at least one sequestration pen.

22. The microfluidic device of any one of embodiments 1-21, where a cover of the microfluidic device may be substantially transparent to a fluorescent, colorimetric, or luminescent signal from the one or more capture structures.

23. The microfluidic device of any one of embodiments 1-22, where the solidified polymer network may include a photoinitiated polymer.

24. The microfluidic device of any one of embodiments 1-23, where the solidified polymer network may include a synthetic polymer, a modified synthetic polymer, a biological polymer, or any combination thereof.

25. The microfluidic device of embodiment 24, where the modified synthetic polymer may include cleavage motifs, reactive terminal moieties, and/or cell recognition motifs.

26. The microfluidic device of any one of embodiments 1-25, where the solidified polymer network may include at least one of a polyethylene glycol, modified polyethylene glycol, polylactic acid (PLA), modified polylactic acid, polyglycolic acid (PGA), modified polyglycolic acid, polyacrylamide (PAM), modified polyacrylamide, poly-N-isopropylacrylamide (PNIPAm), modified poly-N-isopropylacrylamide, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, laminin, modified laminin, polysaccharide, modified polysaccharide, or any co-polymer combination thereof.

27. The microfluidic device of any one of embodiments 1-26, wherein the solidified polymer network comprises a modified polyethylene glycol polymer.

28. The microfluidic device of any one of embodiments 1-27, where the microfluidic device may include a plurality of sequestration pens.

29. The microfluidic device of any one of embodiments 4-28, where the at least one in situ-generated capture structure may be configured to permit exit of a micro-object from the sequestration pen.

30. The microfluidic device of any one of embodiments 1-29, where the substrate may be configured to generate dielectrophoresis (DEP) forces within the enclosure.

31. The microfluidic device of embodiment 30, where the DEP forces may be optically actuated.

32. The microfluidic device of any one of embodiments 1-31, where at least one inner surface of the microfluidic device may further include a conditioned surface.

33. A method of assaying a micro-object in a microfluidic device including at least a first in situ-generated capture structure, the method including: disposing a micro-object within a microfluidic device in a region proximal to the at least first in situ-generated capture structure, the in situ-generated capture structure including a solidified polymer network, where the solidified polymer network comprises an assay reagent or assay analyte; contacting the assay reagent or assay analyte with the micro-object or a biological product of the micro-object; and detecting an interaction of the assay reagent or assay analyte with the micro-object or the biological product.

34. The method of embodiment 33, where the microfluidic device may include an enclosure including: a substrate; a flow region; and, optionally, at least one sequestration pen, where the first in situ-generated capture structure is disposed within the flow region or the at least one sequestration pen.

35. The method of embodiments 33 or 34, where the at least one sequestration pen may include an isolation region and a connection region, the connection region having a proximal opening to the flow region and a distal opening to the isolation region.

36. The method of embodiment 35, where the at least first in situ-generated capture structure may be disposed within the isolation region of the sequestration pen.

37. The method of any one of embodiments 33-36, where the assay reagent or assay analyte may be non-covalently attached to the solidified polymer network.

38. The method of any one of embodiments 33-37, where the assay reagent or assay analyte may include a protein, an oligonucleotide, an organic molecule, or a saccharide.

39. The method of any one of embodiments 33-38, where the assay reagent may include an antibody.

40. The method of any one of embodiments 33-39, where the biological product may include a protein, an oligonucleotide, an organic molecule, or a saccharide.

41. The method of embodiment 40, where the protein biological product may include an antibody or an antigen.

42. The method of any one of embodiments 33-41, where the micro-object may include a biological micro-object.

43. The method of any one of embodiments 33-42, where the micro-object may include a hybridoma cell, a B cell or a T cell.

44. The method of any one of embodiments 33-43, where the first in situ-generated capture structure may be disposed at a first location adjacent to a first wall of the sequestration pen.

45. The method of any one of embodiments 33-44, where the step of contacting the assay reagent or assay analyte with the biological product or the micro-object may further include forming a non-covalent complex.

46. The method of any one of embodiments 33-45, where the step of detecting the interaction may further include introducing a detection reagent having a detectable label to the region proximal to the at least first in situ-generated capture structure.

47. The method of embodiment 46, where the detectable label may be configured to be concentrated to the at least first in situ-generated capture structure when the assay reagent or assay analyte interacts with the biological product or the micro-object.

48. The method of embodiment 46 or 47, where the detectable label of the detection reagent is fluorescent, colorimetric, or luminescent.

49. The method of any one of embodiments 46-48, where the detection reagent may include at least a first antibody.

50. The method of embodiment 49, where the antibody detection reagent may further include a secondary antibody.

51. The method of any one of embodiments 46-48, where the detection reagent may include an intercalating dye.

52. The method of any one of embodiments 46-48, where the detection reagent may include an oligonucleotide.

53. The method of embodiment 46-53, where the step of detecting an interaction of the assay reagent or assay analyte with the micro-object or the biological product may further include quantifying the amount of detectable label attached to the at least one in situ-generated capture structure.

54. The method of any one of embodiments 33-53, where the step of detecting may include detecting a fluorescent signal from the at least one in situ-generated capture structure.

55. The method of any one of embodiments 34-54, where the microfluidic device may further include a second in situ-generated capture structure disposed within the flow region or the at least one sequestration pen, where the in situ-generated second capture structure may include a second solidified polymer network, and further where the in situ-generated second solidified polymer network may include a second assay reagent or assay analyte.

56. The method of embodiment 55, where each of the first and second in situ-generated capture structures may include a different assay reagent or assay analyte.

57. The method of embodiment 55 or 56, where the first and the second in situ-generated capture structures may be disposed within the flow region or the sequestration pen at distinguishable locations.

58. The method of any one of embodiments 55-57, where the step of detecting may include detecting a first biological product of the micro-object and a second biological product of the micro-object, where the first biological product is different from the second biological product.

59. The method of any one of embodiments 55-58, where the step of detecting the interaction may further include introducing a first detection reagent and a second detection reagent to the region proximal to the first and second in situ-generated capture structures, where each of the first and second detection reagents may include a detectable label.

60. The method of embodiment 59, where the detecting step may include allowing each of the first and second detectable labels to become non-covalently attached to the respective first assay reagent or assay analyte and the second assay reagent or assay analyte.

61. The method of embodiment 59 or 60, where the step of detecting the interaction may further include detecting a first fluorescent signal from the first detectable label and a second fluorescent signal from the second detectable label.

62. The method of embodiment 61, where the first and the second fluorescent signals may be spectrally distinct.

63. The method of embodiment 61 or 62, where the first and second fluorescent signals may be distinguishable by position.

64. The method of any one of embodiments 61-63, further comprising the step of quantifying the first and/or the second fluorescent signals.

65. The method of any one of embodiments 55-64, further including a third or more in situ-generated capture structure disposed within the flow region or the at least one sequestration pen, where each of the third or more in situ-generated capture structures may include a solidified polymer network, and further where the solidified polymer network of each of the third or more solidified polymer networks may include an assay reagent or assay agent.

66. The method of embodiment 65, where the step of detecting may further include detecting a first, a second, a third or more detectable signals that are distinct in location within the flow region or the at least one sequestration pen, detectably spectrally distinct from each other, or a combination thereof.

67. The method of any one of embodiments 33-66, where the step of disposing the micro-object within the microfluidic device in the region proximal to the at least first in situ-generated capture structure may include moving the micro-object using dielectrophoresis force.

68. The method of embodiment 67, where the dielectrophoresis force may be optically actuated.

69. The method of any one of embodiments 33-68, where at least one inner surface of the microfluidic device may further include a conditioned surface.

70. A kit including: a microfluidic device having an enclosure including a substrate, microfluidic circuit material, and, optionally, a cover, the enclosure defining a flow region; and a functionalized pre-polymer that can be controllably activated to form a solidified polymer network.

71. A kit including: a microfluidic device having an enclosure including a substrate, microfluidic circuit material, and, optionally, a cover, the enclosure defining a flow region; and at least one in situ-generated capture structure disposed within enclosure, where the at least one in situ-generated capture structure includes a solidified polymer network.

72. The kit of embodiment 70 or 71, wherein the enclosure of the microfluidic device further comprises at least one sequestration pen fluidically connected to the flow region.

73. The kit of any one of embodiments 70-72, where the solidified polymer network may include one or more functionalized sites.

74. The kit of any one of embodiments 70-73, further including an assay reagent or assay analyte.

75. The kit of embodiment 74, where the assay reagent or assay analyte may further include a functionalized assay reagent or assay analyte.

76. The kit of embodiment 75, where the functionalized assay reagent or assay analyte may include a moiety configured to associate or bind to the one or more functionalized sites of the solidified polymer network.

77. The kit of any one of embodiments 74-76, where the solidified polymer network may include the assay reagent or assay analyte.

78. The kit of embodiment 77, where the assay reagent or assay analyte may be covalently attached to the solidified polymer network.

79. The kit of embodiment 77, where the assay reagent or assay analyte may be non-covalently attached to the solidified polymer network.

80. The kit of embodiment 79, where the assay reagent or assay analyte may be non-covalently attached to the solidified polymer network via a biotin/streptavidin complex.

81. The kit of any one of embodiments 70-80, where the solidified polymer network may include a synthetic polymer, a modified synthetic polymer, or a biological polymer.

82. The kit of embodiment 81, where the synthetic polymer modifications may include size modification motifs, cleavage motifs, reactive terminal moieties, and/or cell recognition motifs.

83. The kit of any one of embodiments 70-82, where the solidified polymer network may include at least one of a polyethylene glycol, modified polyethylene glycol, polylactic acid (PLA), modified polylactic acid, polyglycolic acid (PGA), modified polyglycolic acid, polyacrylamide (PAM), modified polyacrylamide, poly-N-isopropylacrylamide (PNIPAm), modified poly-N-isopropylacrylamide, polyvinyl alcohol (PVA), modified polyvinyl alcohol, polyacrylic acid (PAA), modified polyacrylic acid, polycaprolactone (PCL), modified polycaprolactone, fibronectin, modified fibronectin, collagen, modified collagen, laminin, modified laminin, polysaccharide, modified polysaccharide, or a co-polymer in any combination.

84. The kit of any one of embodiments, 70-83, wherein the solidified polymer network includes a modified polyethylene glycol.

85. The kit of any one of embodiments 74-84, where the assay reagent or assay analyte may include a protein, a nucleic acid, an organic molecule, or a saccharide.

86. The kit of any one of embodiments 74-85, where the assay reagent or assay analyte may include an antibody.

87. The kit of any one of embodiments 74-85, where the assay reagent or assay analyte may include an antigen.

88. The kit of any one of embodiments 74-85, where the assay reagent may include a capture oligonucleotide.

89. The kit of any one of embodiments 70-88, further including a detection reagent.

90. The kit of embodiment 89, where the detection reagent may include a detectable label.

91. The kit of embodiment 90, where the detectable label of the detection reagent may include a fluorescent, colorimetric, or luminescent label.

92. The kit of any one of embodiments 89-91, where the detection reagent may include at least a first antibody.

93. The kit of any one of embodiments 89-91, where the detection reagent may include an intercalating dye.

94. The kit of any one of embodiments 89-91, where the detection reagent may include a FRET labeled oligonucleotide.

95. The kit of any one of embodiments 71-94, where the enclosure may include at least first and second in situ-generated capture structures disposed therein, where the first in situ-generated capture structure includes a first solidified polymer network, and where the second in situ-generated capture structure includes a second solidified polymer network.

96. The kit of embodiment 95, where the first and second situ-generated capture structures are disposed within the flow region.

97. The kit of embodiment 95, where the first and second in situ-generated capture structures are disposed within the at least one sequestration pen.

98. The kit of any one of embodiments 95-97, where a first in situ-generated capture structure and a second in situ-generated capture structure may be disposed in different locations within the flow region or sequestration pen.

99. The kit of embodiment 70, further comprising a second functionalized pre-polymer that can be controllably activated to form a second solidified polymer network.

100. The kit of any one of embodiments 95-99, which further includes a first assay reagent and second assay reagent, and further where the first assay reagent may be different from the second assay reagent.

101. The kit of embodiment 100, where the first solidified polymer network includes the first assay reagent and the second solidified polymer network includes the second assay reagent.

102. The kit of any one of embodiments 95-101, further including a first detection reagent and a second detection reagent, where the first detection reagent may be different from the second detection reagent.

103. The kit of embodiment 102, where the first detection reagent includes a first detectable label and the second detection reagent includes a second detectable label, where the first detectable label and the second detectable label may be spectrally distinct.

104. The kit of any one of embodiments 70-103, where the enclosure of the microfluidic device may further include a plurality of sequestration pens.

105. The kit of embodiment 104, where each of the plurality of sequestration pens may include at least one capture structure including a solidified polymer network.

106. The kit of any one of embodiments 70-105, where at least one inner surface of the microfluidic device may further include a conditioned surface.

107. A method of preparing a microfluidic device including at least a first in situ-generated capture structure, including: providing the microfluidic device, where the microfluidic device comprises an enclosure including a substrate and a microfluidic circuit material, the enclosure defining a flow region; introducing a first flowable functionalized pre-polymer into the flow region; and activating solidification of the first flowable functionalized pre-polymer at at least one selected area of the enclosure, thereby forming the at least a first in situ-generated capture structure therein.

108. The method of embodiment 107, where the enclosure further defines at least one sequestration pen.

109. The method of embodiment 107 or 108, where the first in situ-generated capture structure is formed in the flow region.

110. The method of embodiment 108, where the first in situ-generated capture structure is formed in the sequestration pen.

111. The method of any one of embodiments 107-110, where the at least first in-situ generated capture structure may include a solidified polymer network including one or more functionalized sites.

112. The method of embodiment 110, where the one or more functionalized sites may include a biotin, avidin, or streptavidin moiety.

113. The method of embodiment 111 or 112, where the one or more functionalized sites may be covalently bound to at least one component of the first flowable functionalized pre-polymer.

114. The method of any one of embodiments 107-113, further including a step of flowing a first volume of a first fluidic medium through the flow region of the microfluidic device, thereby diffusing unsolidified first flowable functionalized pre-polymer out of the flow region and, optionally, the at least one sequestration pen.

115. The method of any one of embodiments 107-114, further including introducing a first functionalized assay reagent or assay analyte to the at least first capture structure; and associating the first functionalized assay reagent or assay analyte to the functionalized sites of the solidified polymer network of the at least first capture structure.

116. The method of embodiment 115, further including flowing a second volume of the first fluidic medium through the microfluidic device, thereby diffusing unassociated first functionalized assay reagent or assay analyte out of the flow region and, optionally, the at least one sequestration pen.

117. The method of embodiment 115 or 116, where the first functionalized assay reagent or assay analyte may include an antibody, antigen, organic molecule, or an oligonucleotide.

118. The method of embodiment 117, where the organic molecule of the first functionalized assay reagent or assay analyte may include a substrate to an enzyme, an antigen, a cell surface marker, or a cytokine.

119. The method of any one of embodiments 115-118, where the first functionalized assay reagent or assay analyte may further include a moiety configured to associate the first functionalized assay reagent or assay analyte with the functionalized site of the solidified polymer network of the at least first capture structure.

120. The method of embodiment 119, where the moiety configured to associate the first functionalized assay reagent or assay analyte may include a biotin, avidin or streptavidin binding partner to the functionalized site of the solidified polymer network of the at least first capture structure.

121. The method of any one of embodiments 115-120, where the first functionalized assay reagent or assay analyte may be a first assay reagent.

122. The method of any one of embodiments 107-121, further including the step of introducing a second functionalized assay reagent or assay analyte.

123. The method of embodiment 122, where the second functionalized assay reagent or assay analyte may associate with second functionalized sites of the solidified polymer network of the at least first capture structure.

124. The method of embodiment 123, where the second functionalized assay reagent or assay analyte may be detectably differentiable from the first functionalized assay reagent or assay analyte.

125. The method of embodiment 123, where the second functionalized assay reagent or assay analyte may associate with first functionalized sites on a second capture structure in the at least one sequestration pen.

126. The method of embodiment 125, further including introducing the second capture structure in the flow region or the at least one sequestration pen, where introducing the second capture structure may include the steps of: introducing a second flowable functionalized pre-polymer into the flow region; and activating solidification of the second flowable functionalized pre-polymer at at least a second selected area of the enclosure, thereby forming the second in situ-generated capture structure therein; and flowing yet another volume of the first fluidic medium into the flow region of the microfluidic device.

127. The method of embodiment 126, further including introducing a third capture structure into the flow region or the at least one sequestration pen, where introducing the third capture structure may include: introducing a third flowable functionalized pre-polymer into the flow region; and activating solidification of the third flowable functionalized pre-polymer at at least a third selected area of the enclosure, thereby forming the third in situ-generated capture structure therein; and flowing yet another volume of the first fluidic medium into the flow region of the microfluidic device.

128. The method of any one of embodiments 122-127, where the second functionalized assay reagent or assay analyte may be different from the first functionalized assay reagent or assay analyte.

129. The method of any one of embodiments 126-128, where the first flowable functionalized pre-polymer is different from the second flowable functionalized pre-polymer.

130. The method of any one of embodiments 127-129, where each of the first, second, and third flowable functionalized pre-polymer may be different from each other.

131. The method of any one of embodiments 127-130, further including the step of introducing a third functionalized assay reagent or assay analyte.

132. The method of embodiment 131, where the third functionalized assay reagent or assay analyte may associate with a first functionalized site on the third capture structure in the at least one sequestration pen.

133. The method of embodiment 131 or 132, where the third functionalized assay reagent or assay analyte may be different from the first functionalized assay reagent or assay analyte and from the second functionalized assay reagent or assay analyte.

134. The method of any one of embodiments 107-133, where at least one inner surface of the microfluidic device may further include a conditioned surface.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner. Furthermore, where reference is made herein to a list of elements (e.g., elements a, b, c), such reference is intended to include any one of the listed elements by itself, any combination of less than all of the listed elements, and/or a combination of all of the listed elements. As used herein, the terms a, an, and one may each be interchangeable with the terms at least one and one or more. It should also be noted, that while the term step is used herein, that term may be used to simply draw attention to different portions of the described methods and is not meant to delineate a starting point or a stopping point for any portion of the methods, or to be limiting in any other way.

What is claimed:

1. A microfluidic device comprising:
   an enclosure comprising a substrate and microfluidic circuit material, the enclosure defining a flow region and at least one sequestration pen, each located within the enclosure; and
   at least one in situ-generated capture structure disposed within the at least one sequestration pen, wherein the at least one in situ-generated capture structure comprises a solidified polymer network, and wherein the solidified polymer network comprises one or more functionalized sites.

2. The microfluidic device of claim 1, wherein the solidified polymer network comprises an assay reagent or assay analyte.

3. The microfluidic device of claim 1, wherein the at least one sequestration pen comprises an isolation region and a connection region, the connection region having a proximal opening to the flow region and a distal opening to the isolation region.

4. The microfluidic device of claim 3, wherein the at least one in situ-generated capture structure is disposed within the isolation region of the sequestration pen.

5. The microfluidic device of claim 1, wherein the solidified polymer network comprises an assay reagent that is non-covalently attached to the solidified polymer network.

6. The microfluidic device of claim 1, wherein the solidified polymer network comprises an assay reagent that comprises a protein, a nucleic acid, an organic molecule, and/or a saccharide.

7. The microfluidic device of claim 6, wherein the assay reagent comprises an antibody or an antigen.

8. The microfluidic device of claim 1, wherein two or more in situ-generated capture structures are disposed in the at least one sequestration pen.

9. The microfluidic device of claim 1, wherein the solidified polymer network comprises a photoinitiated polymer.

10. The microfluidic device of claim 1, wherein the solidified polymer network comprises a synthetic polymer, a modified synthetic polymer, a biological polymer, or any combination thereof.

11. The microfluidic device of claim 1, wherein the substrate is configured to generate dielectrophoresis (DEP) forces within the enclosure.

12. A method of assaying a micro-object in a microfluidic device comprising at least a first in situ-generated capture structure comprising:
    disposing a micro-object within the microfluidic device in a region proximal to the at least first in situ-generated capture structure comprising a solidified polymer network, wherein the solidified polymer network comprises an assay reagent or assay analyte;
    contacting the assay reagent or assay analyte with the micro-object or a biological product of the micro-object; and
    detecting an interaction of the assay reagent or assay analyte with the micro-object or the biological product.

13. The method of claim 12, wherein the microfluidic device comprises: an enclosure comprising a substrate and microfluidic circuit material, the enclosure defining a flow region and at least one sequestration pen; and wherein the at least first in situ-generated capture structure is disposed within the at least one sequestration pen.

14. The method of claim 13, wherein the at least one sequestration pen comprises an isolation region and a connection region, the connection region having a proximal opening to the flow region and a distal opening to the isolation region, and further wherein the at least first in-situ generated capture structure is disposed within the isolation region of the sequestration pen.

15. The method of claim 12, wherein the assay reagent or assay analyte is non-covalently attached to the solidified polymer network.

16. The method of claim 12, wherein the solidified polymer network comprises an assay reagent, and wherein the assay reagent comprises a protein.

17. The method of claim 16, wherein the assay reagent comprises an antigen or an antibody.

18. The method of claim 12, wherein the biological product comprises a protein, an oligonucleotide, an organic molecule, or a saccharide.

19. The method of claim 12, wherein the biological product of the micro-object is an antibody or an antigen.

20. The method of claim 12, wherein the step of contacting the assay reagent or assay analyte with the biological product or the micro-object further comprises forming a non-covalent complex.

21. The method of claim 12, wherein the step of detecting the interaction further comprises introducing a detection reagent having a detectable label to the region proximal to the at least first in situ-generated capture structure.

22. The method of claim 21, wherein the detectable label is configured to be concentrated to the at least first in situ-generated capture structure when the assay reagent or assay analyte interacts with the biological product or the micro-object.

23. The method of claim 12, wherein the step of detecting comprises detecting a fluorescent signal from the at least first in situ-generated capture structure.

24. The method of claim 13, wherein the microfluidic device further comprises a second in situ-generated capture structure disposed within the at least one sequestration pen, wherein the second in situ-generated capture structure comprises a second solidified polymer network and further wherein the second solidified polymer network comprises a second assay reagent or assay analyte, wherein each of the first and second in situ-generated capture structures comprises a different assay reagent or assay analyte, and wherein the step of detecting comprises detecting a first biological product of the micro-object and a second biological product of the micro-object, wherein the first biological product is different from the second biological product.

25. The method of claim 12, wherein the step of disposing the micro-object within the microfluidic device in the region proximal to the at least first in situ-generated capture structure comprises moving the micro-object using dielectrophoresis force.

26. A method of preparing a microfluidic device comprising at least a first in situ-generated capture structure, the method comprising:
    providing the microfluidic device, wherein the microfluidic device comprises an enclosure comprising a substrate and microfluidic circuit material, the enclosure defining a flow region and at least one sequestration pen fluidically connected to the flow region;
    introducing a first flowable functionalized pre-polymer into the flow region; and
    activating solidification of the first flowable functionalized pre-polymer at at least one selected area of the at least one sequestration pen, thereby forming the at least a first in situ-generated capture structure therein.

27. The microfluidic device of claim 1, wherein the in situ-generated capture structure is affixed to a portion of the microfluidic device.

28. The microfluidic device of claim 1, wherein the in situ-generated capture structure is affixed to a portion of the at least one sequestration pen.

29. The microfluidic device of claim 1, wherein at least one of the one or more functionalized sites comprises a reactive moiety for binding of an assay reagent or an assay analyte.

\* \* \* \* \*